United States Patent
Palmer et al.

(10) Patent No.: US 10,888,567 B2
(45) Date of Patent: Jan. 12, 2021

(54) INHIBITORS OF TRYPTOPHAN DIOXYGENASES (IDO1 AND TDO) AND THEIR USE IN THERAPY

(71) Applicant: AUCKLAND UNISERVICES LIMITED, Auckland (NZ)

(72) Inventors: Brian Desmond Palmer, Auckland (NZ); Lai Ming Ching, Auckland (NZ); Swarnalatha Akuratiya Gamage, Auckland (NZ)

(73) Assignee: Auckland UniServices Limited, Auckland (NZ)

( * ) Notice: Subject to any disclaimer, the term of this patent is extended or adjusted under 35 U.S.C. 154(b) by 0 days.

(21) Appl. No.: 15/503,210

(22) PCT Filed: Aug. 12, 2015

(86) PCT No.: PCT/IB2015/056129
§ 371 (c)(1),
(2) Date: Feb. 10, 2017

(87) PCT Pub. No.: WO2016/024233
PCT Pub. Date: Feb. 18, 2016

(65) Prior Publication Data
US 2017/0224701 A1    Aug. 10, 2017

(30) Foreign Application Priority Data
Aug. 13, 2014  (NZ) ........................................ 628688

(51) Int. Cl.
| | | |
|---|---|---|
| *A61K 31/5377* | (2006.01) | |
| *A61K 45/06* | (2006.01) | |
| *A61K 31/444* | (2006.01) | |
| *A61K 31/519* | (2006.01) | |
| *A61K 31/437* | (2006.01) | |
| *C07D 498/04* | (2006.01) | |
| *A61K 31/4745* | (2006.01) | |
| *A61K 31/423* | (2006.01) | |

(52) U.S. Cl.
CPC ........ *A61K 31/5377* (2013.01); *A61K 31/423* (2013.01); *A61K 31/437* (2013.01); *A61K 31/444* (2013.01); *A61K 31/4745* (2013.01); *A61K 31/519* (2013.01); *A61K 45/06* (2013.01); *C07D 498/04* (2013.01)

(58) Field of Classification Search
CPC .................................................. A61K 31/5377
See application file for complete search history.

(56) References Cited

U.S. PATENT DOCUMENTS

| | | |
|---|---|---|
| 8,598,356 B2 | 12/2013 | Breitenbucher et al. |
| 2008/0176915 A1 | 7/2008 | Merla et al. |
| 2008/0312301 A1 | 12/2008 | Merla et al. |
| 2010/0234419 A1 | 9/2010 | Kuhnert et al. |
| 2013/0289083 A1 | 10/2013 | Mautino et al. |

FOREIGN PATENT DOCUMENTS

| | | | |
|---|---|---|---|
| EP | 1813606 A1 | | 8/2007 |
| PL | 402290 A1 | * | 7/2014 |
| PL | 220630 B1 | * | 11/2015 |
| RU | 2619120 C1 | | 5/2017 |
| WO | 01/79193 A2 | | 10/2001 |
| WO | WO 2005/089753 A2 | | 9/2005 |
| WO | WO 2010/068453 A1 | | 6/2010 |
| WO | WO 2010/102778 A2 | | 9/2010 |
| WO | WO 2011/100614 | | 8/2011 |
| WO | WO 2012/010633 A1 | | 1/2012 |
| WO | WO 2013/104561 A1 | | 7/2013 |
| WO | 2014186035 A1 | | 11/2014 |
| WO | WO 2015/082499 A2 | | 6/2015 |

OTHER PUBLICATIONS

STN Chemical Database entry for 6-chloro-Isoxazolo[5,4-b]pyridin-3-amine, RN 1502034-41-4, SR Chemical Catalog Supplier: Aurora Fine Chemicals ED Entered STN: Dec. 24, 2013.*
"http://web.archive.org/web/20070406205858/http://www.aurorafinechemicals.com/english/order.html" dated Apr. 6, 2007, accessed Feb. 19, 2015.*
Online: "http://web.archive.org/web/20070630171813/http://www.enamine.net/index.php?option=com_content&task=view&id=22&menuid=51&PHPSESSID=64a4f248f69d671a413f487bb62c4d90" dated Jun. 30, 2007, accessed Apr. 1, 2015.*
Online "http://web.archive.org/web/20051204015543/http://www.chemblock.com/screening.php" Dec. 4, 2005.*

(Continued)

*Primary Examiner* — David K O'Dell
(74) *Attorney, Agent, or Firm* — McDonnell Boehnen Hulbert & Berghoff LLP

(57) ABSTRACT

Pharmaceutical compositions comprising 3-aminoisoxazolopyridine compounds of the Formula I having IDO1 and/or TDO inhibitory activity are described, where W is $CR^1$, N or N-oxide; X is $CR^2$, N or N-oxide; Y is $CR^3$, N or N-oxide; Z is $CR^4$, N or N-oxide; and at least one of W, X, Y, and Z is N or N-oxide; and $R^9$ and $R^{10}$ are as defined. Also described are methods of using such compounds in the treatment of various conditions, such as cancer.

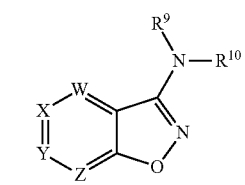

I

4 Claims, 3 Drawing Sheets

(56) References Cited

OTHER PUBLICATIONS

Zadbuke "Recent trends and future of pharmaceutical packaging technology" J Pharm Bioallied Sci. Apr.-Jun. 2013; 5(2): 98-110.*
STN-Chemical database registry # RN 893767-99-2, 5-chloro-4,6-dimethyl-Isoxazolo[5,4-b]pyridin-3-amine, Jul. 17, 2006.*
Wakefield "Fluorinated Pharmaceuticals" Innovations in Pharmaceutical Technology 2003, 74, 76-78.*
Schönherr "Profound Methyl Effects in Drug Discovery and a Call for New C—H Methylation Reactions" Angew. Chem. Int. Ed. 2013, 52, 12256-12267.*
Uyttenhove et al., "Evidence for a tumoral immune resistance mechanism based on tryptophan degradation by indoleamine 2,3-dioxygenase," Nature Medicine, 2003, 9, No. 10, 1269. 8 pages.
Zheng et al., "Reinstalling Antitumor Immunity by Inhibiting Tumor-Derived Immunosuppressive Molecule IDO through RNA Interference," J. Immunol. 2006, 177, 5639, 9 pages.
Matutino et al., "Abstract 5023: Synergistinc Antitumor effects of combinatorial immune checkpoint inhibition with anti-PD-1/PD-L antibodies and the IDO pathway inhibitors NLG-919 and indoximod in the context of active immunotherapy," Proceedings of the AACR Annual Meeting, 2014, Poster 5023, 2 pages.
Cady and Sono, "1-Methyl-DL-tryptophan, β-(3-Benzofuranyl)-DL-alanine (the Oxygen Analog of Tryptophan), and β-[3-Benzo9b)thienyl]-DL-alanine (the Sulfur Analog of Tryptophan) are Competitive Inhibitors for Indoleamine 2, 3-Dioxygenase," Arch. Biochem. Biophys.1991, 291, 326, 8 pages.
Hou et al., "Inhibition of Indoleamine 2,3-Dioxygenase in Dendritic Cells by Stereoisomers of 1-Methyl-Tryptophan Correlates with Antitumor Responses," Cancer Res. 2007, 67, 792, 11 pages.
Brasstianos et al., "Exiguamine A, an Indoleamine-2,3-dioxygenase (IDO) Inhibitor Isolated from the Marine Sponge *Neopetrosia exigua*," J. Am. Chem. Soc., 2006, 128, 16046, 2 pages.
Pereira et al., "Indoleamine 2,3-Dioxygenase Inhibitors from the Northeastern Pacific Marine Hydroid Garveia annulata," J. Nat. Prod. 2006, 69, 1496, 4 pages.
Kumar et al., "Indoleamine 2,3-Dioxyganase is the Anticancer Target for a Novel Series of Potent Naphthoquinone-Based Inhibitores," J. Med. Chem. 2008, 51, 1706, 13 pages.
Yue et al., "Discovery of Potent Competitive Inhibitors of Indoleamine 2,3-Dioxygenase with in Vivo Pharmacodynamic Activity and Efficacy in a Mouse Melanoma Model," J. Med. Chem., 2009, 52, 7364, 4 pages.
Newton et al., "Pharmacodynamic assessment of INCB024360, an inhibitor of indoleamine 2,3-dioxygenase 1 (IDO1), in advanced cancer patients," J. Clin Oncol., 29012, 30, (Suppl; abstract 2500), 4 pages.
Mautino et al., "Abstract 491: NLG919, a nevel idoleamine-2,3-dixygenase (IDO)-pathway inhibitor drug candidtae for cancer therapy," Proceedings of teh AACR Annual Meeting, 2013, 2 pages.
Srivastava et al., "Synthetic Applications of 2-Chloro-3-Formylquinoline," Journal of Heterocyclic Chemistry, 1987, 24(1), 219-222, 4 pages.
Tichenor et al., "Heteroaryl urea inhibitors of fatty acid amide hydrolase: Structure-mutagenicity relationships for arylamine metabolites," Bioorganic & Medicinal Chemistry Letters, 2012, 22, 7357-7362, 6 pages.
Witherington et al., "5-Aryl-pyrazolo[3,4-b]pyridines: Potent Inhibitors of Glycogen Synthase Kinase-3 (GSK-3)," Bioorganic & Medicinal Chemistry Letters, 2003, 13(9), 1577-80, 4 pages.
Taha et al., "Pharmacophore Modeling, Quantitative Structure-Activity Relationship Analysis, and in Silico Screening Reveal Potent Glycogen Synthase Kinase-3β Inhibitory Activities for Cimetidine, Hydroxychloroquine, and Gemifloxacin," J. Med. Chem., 2008, 51, 2062-2077, 16 pages.
Poreba et al., "Synthesis and Antibacterial Activity fo New Sulfonamide Isoxazolo[5,4-b]Pyridine Derivatives," Acta Poloniae Pharmaceutica—Drug Research, 2015, vol. 72, No. 4, pp. 727,735, 9 pages.
Poreba et al., "Synthesis and Antiproliferative Activity In Vitro of New 3-Substituted Aminoisoxazolo[5,4-b]Pyridines," Acta Poloniae Pharmaceutica—Drug Reserach, 2003, vol. 60, No. 4, pp. 293,301, 9 pages.
Shing et al., "A novel class of inhibitors of the immunosuppressive enzyme indoleamine 2,3-dioxygenase 1 (IDO1) for the treatment of cancer," Poster 4469, AACR 106th Annual Meeting 2015; Apr. 18-22, 2015; Philadelphia, PA.
Cheng et al., "Discovery and structure-activity relationships of phenyl benzyenesulfonylhydrazides as novel indoleamine-2,3-dioxygenase inhibitors," Bioorganic & Medicinal Chemcistry Letters, 2014, 24(15) (accepted manuscript).
Wardakhan, Wagnat W. et al., "Utility of 2-Aminothiophene-3-carboxamide in the synthesis of Biologically Active, Fused Heterocyclic Derivatives," Phosphorus, Sulfur and Silicon and the Related Elements, vol. 18, No. 1, Jan. 1, 2005, pp. 125-140.
European Search Report for 16839685.1, 11 pages, dated Jan. 3, 2019.
Srivastava et al., "Synthetic applications of 2-chloro-3-formylquinoline" J. Heterocyclic Chem., 24, 219-222 (1987).
Elnagdi et al., "Pyrimidine derivatives and related compounds. A novel synthesis of pyrimidines, pyrazolo[4,3-d] pyrimidines and isoxazolo[4,3-d] pyrimidine" J. Heterocyclic Chem., 16, 1109-1111 (1979).
Al-Mousawi et al., "On the Reaction of Phenacylmalononitrile with Hydrazines: a new route to pyrazolo[3,4-c] pyridazine, isoxazolo[5,4-c]pyridazine and pyrimido[4,5-c]pyridazine" J. Saudi Chem. Soc., 15, 309-312 (2011).
Tichenor et al., "Heteroaryl urea inhibitors of fatty acid amide hydrolase: Structure-mutagenicity relationships for arylamine metabolites" Bioorg. Med. Chem. Lett., 22, 7357-7362 (2012).
Mascal et al., "The G—C DNA base hybrid: Synthesis, self-organization and structural analysis" J. Org. Chem., 64, 8479-8484 (1999).
Kocevar et al., "New synthetic approach for pyrazolo[3,4-b] pyrazines and isoxazolo[4,5-b] pyrazines" Heterocycles, 19:2, 339-342 (1982).
Shen et al., "A strategy of employing aminoheterocycles as amide mimics to identify novel, potent and bioavailable soluble epoxide hydrolase inhibitors," Bioorganic & Medicinal Chemistry Letters, 2009, 19(19), 5716-21.
Witherington et al., "5-"Aryl-pyrazolo[3,4-b]pyridines: Potent Inhibitors of Glycogen Synthase Kinase-3 (GSK-3)", Bioorganic & Medicinal Chemisry Letters, 2003, 13(9), 1577-80.

* cited by examiner

INHIBITORS OF TRYPTOPHAN DIOXYGENASES (IDO1 AND TDO) AND THEIR USE IN THERAPY

CROSS-REFERENCE TO RELATED APPLICATIONS

This application is a national stage application under 35 U.S.C. 371 of International Patent Application no. PCT/IB2015/056129, filed Aug. 12, 2015, which claims the benefit of priority of New Zealand patent application no. 628688, filed Aug. 13, 2014.

TECHNICAL FIELD

The present invention relates to 3-aminoisoxazolopyridines, to pharmaceutical compositions containing them and their use as medicaments, and more particularly to their use in cancer therapy, either alone or in combination with other agents, such as anti-cancer vaccines, other types of immunomodulatory therapies, radiation and other chemotherapeutic agents.

BACKGROUND TO THE INVENTION

Indoleamine 2,3-dioxygenase 1 (IDO1) catalyses the first and rate limiting step of tryptophan conversion to kynurenine, and is expressed in a broad range of cancers to suppress the immune system (Uyttenhove et al., *J. Nat. Med.* 2003, 9, 1269). High IDO1 expression in clinical tumours has been shown to correlate with poor patient prognosis in a wide range of cancers including lung, colorectal, breast, melanoma and gynecologic cancers. Silencing of the IDO1 gene in a murine melanoma cell line resulted in reduced capacity of the cells to form tumours when implanted into mice (Zheng et al., *J. Immunol.* 2006, 177, 5639), validating IDO1 as a target for cancer intervention. A number of groups have pursued the development of small molecule inhibitors of IDO1 as an approach for restoring tumour immunity in cancer patients. Such inhibitors should have potential to exhibit antitumour activity on their own, or in combination with other standard chemotherapies. Blocking downstream signalling of the IDO1 enzyme with small molecule inhibitors also has the potential to synergise with other immunomodulatory approaches, such as anti-cancer vaccine administration, modulation of immune checkpoint proteins (such as CTLA4 and the PD1-4s) and the use of adoptive T-cell therapies (such as CART cells) (Mautina et al., Proceedings of the AACR Annual Meeting, 2014, Poster 5023). Early studies used derivatives of tryptophan such as 1-methyltryptophan (1-MT) as competitive inhibitors of IDO1 (Cady and Sono, *Arch. Biochem. Biophys.* 1991, 291, 326) and provided proof of concept that IDO1 would be an attractive target for pharmacological intervention of cancer (Hou et al., *Cancer Res.* 2007, 614). Natural products, isolated from marine invertebrates, inhibit IDO1 at considerably higher potencies than tryptophan derivatives. One of the most potent IDO1 inhibitors that has been described to date, with activity at nM concentrations, is an exiguamine isolated from a marine sponge (Brastianos et al., *J. Am. Chem. Soc.,* 2006, 128, 16046). Two annulins isolated from marine hydroids exhibited activity at nM concentrations, and stimulated a medicinal chemistry program that generated a series of IDO1 inhibitory pyranonaphthoquinones with low nM potency (Pereira et al., *J. Nat. Prod.* 2006, 69, 1496; Kumar et al., *J. Med. Chem.* 2008, 51, 1706). High throughput screening of a compound library led to the discovery and optimisation of a structural class of hydroxyamidine inhibitors of IDO1 (Yue et al., *J. Med. Chem.* 2009, 52, 7364). An optimised hydroxyamidine candidate with nM potency against the enzyme in cells and with oral bioavailability is currently in clinical trials (Newton et al., *J Clin Oncol.* 2012, 30, (Suppl; abstract 2500)). Another potent IDO inhibitor of the imidazoisoindole class is also currently in early stage clinical trials (Mautina et al., Proceedings of the AACR Annual Meeting, 2013).

Tryptophan 2,3-dioxygenase (TDO) is another key enzyme in the tryptophan degradation pathway. TDO inhibitors may also have wide ranging therapeutic efficacy in the treatment of cancer and other conditions.

It is an object of the present invention to provide 3-aminoisoxazolopyridine compounds and their use in medicine, for example in cancer therapy, or at least to provide the public with a useful choice.

SUMMARY OF THE INVENTION

In a first aspect, the present invention provides a pharmaceutical composition comprising:
a compound of Formula I or a pharmaceutically acceptable salt thereof, wherein:

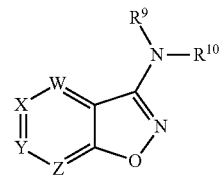

I

W is $CR^1$, N or N-oxide;
X is $CR^2$, N or N-oxide;
Y is $CR^3$, N or N-oxide;
Z is $CR^4$, N or N-oxide;
and where at least one of W, X, Y, and Z is N or N-oxide;
$R^1$, $R^2$, $R^3$ and $R^4$ are each independently selected from the following groups: H, halo, R, —OH, —OR, —OC(O)H, —OC(O)R, —OC(O)NH$_2$, —OC(O)NHR, —OC(O)NRR, —OP(O)(OH)$_2$, —OP(O)(OR)$_2$, —NO$_2$, —NH$_2$, —NHR, —NRR, —NHC(O)H, —NHC(O)R, —NRC(O)R, —NHC(O)NH$_2$, —NHC(O)NRR, —NRC(O)NHR, —SH, —SR, —S(O)H, —S(O)R, —SO$_2$R, —SO$_2$NH$_2$, —SO$_2$NHR, —SO$_2$NRR, —CF$_3$, —CHF$_2$, —CH$_2$F, —OCF$_3$, —OCHF$_2$, —CN, —C≡CH, —C≡CR, —CH=CHR, —CH=CRR, —CR=CHR, —CR=CRR, —CO$_2$H, —CO$_2$R, —CHO, —C(O)R, —C(O)NH$_2$, —C(O)NHR, —C(O)NRR, —CONHSO$_2$H, —CONHSO$_2$R, —CONRSO$_2$R, cyclic C$_3$-C$_7$ alkylamino, imidazolyl, C$_1$-C$_6$ alkylpiperazinyl, morpholinyl and thiomorpholinyl;
or $R^1$ and $R^2$ taken together, or $R^2$ and $R^3$ taken together, or $R^3$ and $R^4$ taken together can form a saturated or a partially saturated or a fully unsaturated 5- or 6-membered ring of carbon atoms optionally including 1 to 3 heteroatoms selected from O, N and S, and the ring is optionally substituted independently with 1 to 4 substituents selected from R;
each R is independently selected from any of the groups defined in paragraphs (a) and (b) below:
(a) an optionally substituted C$_{1-6}$ alkyl group, an optionally substituted C$_{2-6}$ alkenyl group, an optionally substituted C$_{2-6}$ alkynyl group and an optionally substituted C$_{3-7}$ cyclic alkyl group; wherein the one or more optional substituents for each of said alkyl, alkenyl, alkynyl and cyclic alkyl groups are each independently selected from the following groups: halo, —OH, —OR$^5$, —OC(O)R$^5$, —OC(O)NH$_2$, —OC(O)NHR$^5$, —OC(O)NR$^5$R$^5$, —OP(O)(OH)$_2$, —OP(O)(OR$^5$)$_2$, —NO$_2$, —NH$_2$, —NHR$^5$, —NR$^5$R$^5$, —N$^+$(O$^-$) R$^5$R$^5$, —NHC(O)H, —NHC(O)R$^5$, —NR$^5$C(O)R$^5$, —NHC(O)NH$_2$, —NHC(O)NR$^5$R$^5$, —NR$^5$C(O)NHR$^5$, —SH, —SR$^5$, —S(O)H, —S(O)R$^5$, —SO$_2$R$^5$, —SO$_2$NH$_2$, —SO$_2$NHR$^5$, —SO$_2$NR$^5$R$^5$, —CF$_3$, —CHF$_2$, —CH$_2$F, —OCF$_3$, —OCHF$_2$, —CN, —CO$_2$H, —CO$_2$R$^5$, —CHO, —C(O)R$^5$, —C(O)NH$_2$, —C(O)NHR$^5$, —C(O)NR$^5$R$^5$, —CONHSO$_2$H, —C(O)NHSO$_2$R$^5$, —C(O)NR$^5$SO$_2$R$^5$, cyclic C$_3$-C$_7$ alkylamino, imidazolyl, piperazinyl, morpholinyl, thiomorpholinyl, piperidinyl, azepanyl, pyrrolidinyl and azetidinyl; wherein each of the groups imidazolyl, piperazinyl, morpholinyl, thiomorpholinyl, piperidinyl, azepanyl, pyrrolidinyl and azetidinyl are optionally substituted by one or more of the following groups: C$_{1-6}$ alkyl, C$_{2-6}$ alkenyl, C$_{2-6}$ alkynyl, C$_{3-7}$ cyclic alkyl, halo, —OH, —OR$^7$, —OC(O)R$^7$, —OC(O)NH$_2$—OC(O)NHR$^7$, —OC(O)NR$^7$R$^7$, —OP(O)(OH)$_2$, —OP(O)(OR$^7$)$_2$, —NO$_2$, —NH$_2$, —NHR$^7$, —NR$^7$R$^7$, —N$^+$(O$^-$)R$^7$R$^7$, —NHC(O)H, —NHC(O)R$^7$, —NR$^7$C(O)R$^7$, —NHC(O)NH$_2$, —NHC(O)NR$^7$R$^7$, —NR$^7$C(O)NHR$^7$, —SH, —SR$^7$, —S(O)H, —S(O)R$^7$, —SO$_2$R$^7$, —SO$_2$NH$_2$, —SO$_2$NHR$^7$, —SO$_2$NR$^7$R$^7$, —CF$_3$, —CHF$_2$, —CH$_2$F, —OCF$_3$, —OCHF$_2$, —CN, —CO$_2$H, —CO$_2$R$^7$, —CHO, —C(O)R$^7$, —C(O)NH$_2$, —C(O)NHR$^7$, —C(O)NR$^7$R$^7$, —CONHSO$_2$H, —C(O)NHSO$_2$R$^7$, —C(O)NR$^7$SO$_2$R$^7$, an optionally substituted aryl, and an optionally substituted heteroaryl group having up to 12 carbon atoms and having one or more heteroatoms in its ring system which are each independently selected from O, N and S; and wherein the one or more optional substituents for each of said aryl and heteroaryl groups are each independently selected from the following groups: C$_{1-6}$ alkyl, C$_{2-6}$ alkenyl, C$_{2-6}$ alkynyl or C$_{3-7}$ cyclic alkyl, halo, —OH, —OR$^8$, —OC(O)R$^8$, —OC(O)NH$_2$, —OC(O)NHR$^8$, —OC(O)NR$^8$R$^8$, —OP(O)(OH)$_2$, —OP(O)(OR$^8$)$_2$, —NO$_2$, —NH$_2$, —NHR$^8$, —NR$^8$R$^8$, —N$^+$(O)R$^8$R$^8$, —NHC(O)H, —NHC(O)R$^8$, —NR$^8$C(O)R$^8$, —NHC(O)NH$_2$, —NHC(O)NR$^8$R$^8$, —NR$^8$C(O)NHR$^8$, —SH, —SR$^8$, —S(O)H, —S(O)R$^8$, —SO$_2$R$^8$, —SO$_2$NH$_2$, —SO$_2$NHR$^8$, —SO$_2$NR$^8$R$^8$, —CF$_3$, —CHF$_2$, —CH$_2$F, —OCF$_3$, —OCHF$_2$, —CN, —CO$_2$H, —CO$_2$R$^8$, —CHO, —C(O)R$^8$, —C(O)NH$_2$, —C(O)NHR$^8$, —C(O)NR$^8$R$^8$, —CONHSO$_2$H, —C(O)NHSO$_2$R$^8$, and —C(O)NR$^8$SO$_2$R$^8$; wherein each R$^5$, R$^7$ and R$^8$ is independently selected from a C$_{1-6}$ alkyl group, a C$_{2-6}$ alkenyl group, a C$_{2-6}$ alkynyl group and a C$_{3-7}$ cyclic alkyl group; and (b) an optionally substituted aryl, and an optionally substituted heteroaryl group having up to 12 carbon atoms and having one or more heteroatoms in its ring system which are each independently selected from O, N and S; and wherein the one or more optional substituents are each independently selected from the same optional substituents as those defined in (a) above for R;

R$^9$ and R$^{10}$ are each independently selected from any of the groups defined in paragraphs (a) and (b) below:

(a) H, an optionally substituted C$_{1-6}$ alkyl group, an optionally substituted C$_{2-6}$ alkenyl group, an optionally substituted C$_{2-6}$ alkynyl group, and an optionally substituted C$_{3-7}$ cyclic alkyl group; wherein the one or more optional substituents for each of said alkyl, alkenyl, alkynyl and cyclic alkyl are each independently selected from the following groups: halo, —OH, —OR$^{11}$, —OC(O)R$^{11}$, —OC(O)NH$_2$, —OC(O)NHR$^{11}$, —OC(O)NR$^{11}$R$^{11}$, —OP(O)(OH)$_2$, —OP(O)(OR$^{11}$)$_2$, —NO$_2$, —NH$_2$, —NHR$^{11}$, —NR$^{11}$R$^{11}$, —N$^+$(O$^-$)R$^{11}$R$^{11}$, —NHC(O)H, —NHC(O)R$^{11}$, —NR$^{11}$C(O)R$^{11}$, —NHC(O)NH$_2$, —NHC(O)NR$^{11}$R$^{11}$, —NR$^{11}$C(O)NHR, —SH, —SR$^{11}$, —S(O)H, —S(O)R$^{11}$, —SO$_2$R$^{11}$, —SO$_2$NH$_2$, —SO$_2$NHR$^{11}$, —SO$_2$NR$^{11}$R$^{11}$, —CF$_3$, —CHF$_2$, —CH$_2$F, —OCF$_3$, —OCHF$_2$, —CN, —CO$_2$H, —CO$_2$R$^{11}$, —CHO, —C(O)R$^{11}$, —C(O)NH$_2$, —C(O)NHR$^{11}$, —C(O)NR$^{11}$R$^{11}$, —CONHSO$_2$H, —C(O)NHSO$_2$R$^{11}$, —C(O)NR$^{11}$SO$_2$R$^{11}$, cyclic C$_3$-C$_7$ alkylamino, imidazolyl, piperazinyl, morpholinyl, thiomorpholinyl, piperidinyl, azepanyl, pyrrolidinyl and azetidinyl; wherein each of the groups cyclic C$_3$-C$_7$ alkylamino, imidazolyl, piperazinyl, morpholinyl, thiomorpholinyl, piperidinyl, azepanyl, pyrrolidinyl and azetidinyl are optionally substituted by one or more of the following groups: C$_{1-6}$ alkyl, C$_{2-6}$ alkenyl, C$_{2-6}$ alkynyl, C$_{3-7}$ cyclic alkyl, halo, —OH, —OR$^{13}$, —OC(O)R$^{13}$, —OC(O)NH$_2$, —OC(O)NHR$^{13}$, —OC(O)NR$^{13}$R$^{13}$, —OP(O)(OH)$_2$, —OP(O)(OR$^{13}$)$_2$, —NO$_2$, —NH$_2$, —NHR$^{13}$, —NR$^{13}$R$^{13}$—N$^+$(O)R$^{13}$R$^{13}$, —NHC(O)H, —NHC(O)R$^{13}$, —NR$^{13}$C(O)R$^{13}$, —NHC(O)NH$_2$, —NHC(O)NR$^{13}$R$^{13}$, —NR$^{13}$C(O)NHR$^{13}$, —SH, —SR$^{13}$, —S(O)H, —S(O)R$^{13}$, —SO$_2$R$^{13}$, —SO$_2$NH$_2$, —SO$_2$NHR$^{13}$, —SO$_2$NR$^{13}$R$^{13}$, —CF$_3$, —CHF$_2$, —CH$_2$F, —OCF$_3$, —OCHF$_2$, —CN, —CO$_2$H, —CO$_2$R$^{13}$, —CHO, —C(O)R$^{13}$, —C(O)NH$_2$, —C(O)NHR$^{13}$, —C(O)NR$^{13}$R$^{13}$, —CONHSO$_2$H, —C(O)NHSO$_2$R$^{13}$, and —C(O)NR$^{13}$SO$_2$R$^{13}$; wherein each R$^{11}$ and R$^{13}$ is independently selected from a C$_{1-6}$ alkyl group, a C$_{2-6}$ alkenyl group, a C$_{2-6}$ alkynyl group and a C$_{3-7}$ cyclic alkyl group; and (b) an optionally substituted aryl, and an optionally substituted heteroaryl group having up to 12 carbon atoms and having one or more heteroatoms in its ring system which are each independently selected from O, N and S; and wherein the one or more optional substituents for each of said aryl and heteroaryl are each independently selected from the same optional substituents as those defined in (a) above for R$^9$ and R$^{10}$;

or (c) R$^9$ and R$^{10}$ taken together can form a partially saturated or a fully unsaturated 5- or 6-membered ring of carbon atoms optionally including 1 to 3 heteroatoms selected from O, N and S, and the ring can be optionally substituted independently with 1 to 5 substituents selected from the same optional substituents as those defined in (a) above for R$^9$ and R$^{10}$;

and a pharmaceutically acceptable carrier.

In another aspect, the invention provides a compound of Formula I, or a pharmaceutically acceptable salt thereof, for use as a medicament.

In another aspect, the invention provides a compound of Formula I, or a pharmaceutically acceptable salt thereof, for use in medicine.

In a further aspect, the invention provides a compound of Formula I, or a pharmaceutically acceptable salt thereof, for use as a therapeutically active substance.

In a further aspect, the invention provides a compound of Formula I, or a pharmaceutically acceptable salt thereof, for use in treating cancer in a warm blooded animal, including a human.

In a further aspect, the invention provides the use of a compound of Formula I, or a pharmaceutically acceptable salt thereof, in the manufacture of a medicament.

In a further aspect, the invention provides the use of a compound of Formula I, or a pharmaceutically acceptable salt thereof, in the manufacture of a medicament for treating cancer in a warm blooded animal, including a human.

In a further aspect, the invention provides the use of a compound of Formula I, or a pharmaceutically acceptable salt thereof, in the manufacture of a medicament for treating cancer in a warm blooded animal, including a human, wherein the treatment comprises administration of the compound of Formula I and one or more additional agents selected from the group consisting of chemotherapeutic agents, immune-modulating agents such as anti-cancer vaccines, modulators of immune checkpoint proteins, adoptive T cell immunotherapies (for example chimeric antigen receptor T cells (CART cells)), and radiotherapy, and wherein the additional agent is administered either before, during or after administration of the compound of Formula I. In certain embodiments, the additional agent comprises an immune-modulating agent.

In a further aspect, the invention provides a method of treating cancer in a warm blooded animal, including a human, comprising administering to the animal a therapeutically effective amount of a compound of Formula I or a pharmaceutically acceptable salt thereof.

In a further aspect, the invention provides a method of treating cancer in a warm blooded animal, including a human, wherein the method comprises administering to the animal a therapeutically effective amount of a compound of Formula I or a pharmaceutically acceptable salt thereof, and wherein the method further includes the step of administering one or more additional agents selected from the group consisting of chemotherapeutic agents, immune-modulating agents such as anti-cancer vaccines, modulators of immune checkpoint proteins, adoptive T cell immunotherapies (for example chimeric antigen receptor T cells (CART cells)), and radiotherapy, and wherein the additional agent is administered either before, during or after administration of the compound of Formula I. In certain embodiments, the additional agent comprises an immune-modulating agent.

In a further aspect, the invention provides a method of inhibiting indoleamine 2,3-dioxygenase 1 (IDO1) in a warm blooded animal in need thereof, including a human, comprising administering to the animal a compound of Formula I or a pharmaceutically acceptable salt thereof having IDO1 inhibitory activity, in an amount effective to inhibit IDO1.

In a further aspect, the invention provides a method of inhibiting tryptophan 2,3-dioxygenase (TDO) in a warm blooded animal in need thereof, including a human, comprising administering to the animal a compound of Formula I or a pharmaceutically acceptable salt thereof, having TDO inhibitory activity, in an amount effective to inhibit TDO.

In a further aspect, the invention provides a method of inhibiting IDO1 and TDO in a warm blooded animal in need thereof, including a human, comprising administering to the animal a compound of Formula I or a pharmaceutically acceptable salt thereof having both IDO1 and TDO inhibitory activity, in an amount effective to inhibit IDO1 and TDO.

In a further aspect, the invention provides a pharmaceutical combination or kit, comprising
(a) a compound of Formula I or a pharmaceutically acceptable salt thereof, and
(b) one or more additional agents selected from the group consisting of chemotherapeutic agents, and immune-modulating agents such as anti-cancer vaccines, modulators of immune checkpoint proteins and adoptive T cell immunotherapies (for example chimeric antigen receptor T cells (CART cells)).

In a further aspect, the invention provides a pharmaceutical combination or kit, for use in treating cancer, comprising
(a) a compound of Formula I or a pharmaceutically acceptable salt thereof, and
(b) one or more additional agents selected from the group consisting of chemotherapeutic agents, and immune-modulating agents such as anti-cancer vaccines, modulators of immune checkpoint proteins and adoptive T cell immunotherapies (for example chimeric antigen receptor T cells (CART cells)).

In a further aspect, the invention provides a compound of Formula I, or a pharmaceutically acceptable salt thereof, for use in treating a condition or disorder selected from the group consisting of: an inflammatory condition, an infectious disease, a central nervous system disease or disorder, coronary heart disease, chronic renal failure, post anaesthesia cognitive dysfunction, a condition or disorder relating to female reproductive health, and cataracts.

In a further aspect, the invention provides the use of a compound of Formula I, or a pharmaceutically acceptable salt thereof, in the manufacture of a medicament for treating a condition or disorder selected from the group consisting of: an inflammatory condition, an infectious disease, a central nervous system disease or disorder, coronary heart disease, chronic renal failure, post anaesthesia cognitive dysfunction, a condition or disorder relating to female reproductive health, and cataracts.

In a further aspect, the invention provides a method of treating a condition or disorder selected from the group consisting of: an inflammatory condition, an infectious disease, a central nervous system disease or disorder, coronary heart disease, chronic renal failure, post anaesthesia cognitive dysfunction, a condition or disorder relating to female reproductive health, and cataracts, in a warm blooded animal, including a human, wherein the method comprises administering to the animal a therapeutically effective amount of a compound of Formula I or a pharmaceutically acceptable salt thereof.

Certain embodiments of compounds of Formula I, that may be used in any of the compositions, methods, uses and other aspects of the invention as defined above, are described in the numbered paragraphs (1) to (30) below.

(1). A compound of Formula I or a pharmaceutically acceptable salt thereof, as defined above in the first aspect of the invention.

(2). A compound of Formula I or a pharmaceutically acceptable salt thereof, wherein W, X, Y, and Z are all as defined above in the first aspect of the invention, and wherein:

$R^1$, $R^2$, $R^3$ and $R^4$ are each independently selected from the following groups: H, halo, R, —OH, —OR, —OC(O)H, —OC(O)R, —OC(O)NH$_2$, —OC(O)NHR, —OC(O)NRR, —OP(O)(OH)$_2$, —OP(O)(OR)$_2$, —NO$_2$, —NH$_2$, —NHR, —NRR, —NHC(O)H, —NHC(O)R, —NRC(O)R, —NHC(O)NH$_2$, —NHC(O)NRR, —NRC(O)NHR, —SH, —SR, —S(O)H, —S(O)R, —SO$_2$R, —SO$_2$NH$_2$, —SO$_2$NHR, —SO$_2$NRR, —CF$_3$, —OCF$_3$, —OCHF$_2$, —CN, —C≡CH, —C≡CR, —CH═CHR, —CH═CRR, —CR═CHR, —CR═CRR, —CO$_2$H, —CO$_2$R, —CHO, —C(O)R, —C(O)NH$_2$, —C(O)NHR, —C(O)NRR, —CONHSO$_2$H, —CONHSO$_2$R, —CONRSO$_2$R, cyclic C$_3$-C$_7$ alkylamino, imidazolyl, C$_1$-C$_6$ alkylpiperazinyl, morpholinyl and thiomorpholinyl;

or $R^1$ and $R^2$ taken together, or $R^2$ and $R^3$ taken together, or $R^3$ and $R^4$ taken together can form a saturated or a partially saturated or a fully unsaturated 5- or 6-membered ring of carbon atoms optionally including 1 to 3 heteroatoms selected from O, N and S, and the ring is optionally substituted independently with 1 to 4 substituents selected from R;

each R is independently selected from the following groups defined in paragraphs (a) and (b) below:
(a) an optionally substituted $C_{1-6}$ alkyl group, an optionally substituted $C_{2-6}$ alkenyl group, an optionally substituted $C_{2-6}$ alkynyl group and an optionally substituted $C_{3-7}$ cyclic alkyl group; wherein the one or more optional substituents for each of said alkyl, alkenyl, alkynyl and cyclic alkyl groups are each independently selected from the following groups: halo, —OH, —OR$^5$, —OC(O)R$^5$, —OC(O)NH$_2$, —OC(O)NHR$^5$, —OC(O)NR$^5$R$^5$, —OP(O)(OH)$_2$, —OP(O)(OR$^5$)$_2$, —NO$_2$, —NH$_2$, —NHR$^5$, —NR$^5$R$^5$, —N$^+$(O$^-$)R$^5$R$^5$, —NHC(O)H, —NHC(O)R$^5$, —NR$^5$C(O)R$^5$, —NHC(O)NH$_2$, —NHC(O)NR$^5$R$^5$, —NR$^5$C(O)NHR$^5$, —SH, —SR$^5$, —S(O)H, —S(O)R$^5$, —SO$_2$R$^5$, —SO$_2$NH$_2$, —SO$_2$NHR$^5$, —SO$_2$NR$^5$R$^5$, —CF$_3$, —OCF$_3$, —OCHF$_2$, —CN, —CO$_2$H, —CO$_2$R$^5$, —CHO, —C(O)R$^5$, —C(O)NH$_2$, —C(O)NHR$^5$, —C(O)NR$^5$R$^5$, —CONHSO$_2$H, —C(O)NHSO$_2$R$^5$, —C(O)NR$^5$SO$_2$R$^5$, cyclic $C_3$-$C_7$ alkylamino, imidazolyl, piperazinyl, morpholinyl, thiomorpholinyl, piperidinyl, azepanyl, pyrrolidinyl and azetidinyl; wherein each of the groups imidazolyl, piperazinyl, morpholinyl, thiomorpholinyl, piperidinyl, azepanyl, pyrrolidinyl and azetidinyl are optionally substituted by one or more of the following groups: $C_{1-6}$ alkyl, $C_{2-6}$ alkenyl, $C_{2-6}$ alkynyl, $C_{3-7}$ cyclic alkyl, halo, —OH, —OR$^7$, —OC(O)R$^7$, —OC(O)NH$_2$—OC(O)NHR$^7$, —OC(O)NR$^7$R$^7$, —OP(O)(OH)$_2$, —OP(O)(OR$^7$)$_2$, —NO$_2$, —NH$_2$, —NHR$^7$, —NR$^7$R$^7$, —N$^+$(O$^-$)R$^7$R$^7$, —NHC(O)H, —NHC(O)R$^7$, —NR$^7$C(O)R$^7$, —NHC(O)NH$_2$, —NHC(O)NR$^7$R$^7$, —NR$^7$C(O)NHR$^7$, —SH, —SR$^7$, —S(O)H, —S(O)R$^7$, —SO$_2$R$^7$, —SO$_2$NH$_2$, —SO$_2$NHR$^7$, —SO$_2$NR$^7$R$^7$, —CF$_3$, —OCF$_3$, —OCHF$_2$, —CN, —CO$_2$H, —CO$_2$R$^7$, —CHO, —C(O)R$^7$, —C(O)NH$_2$, —C(O)NHR$^7$, —C(O)NR$^7$R$^7$, —CONHSO$_2$H, —C(O)NHSO$_2$R$^7$, —C(O)NR$^7$SO$_2$R$^7$ an optionally substituted aryl, and an optionally substituted heteroaryl group having up to 12 carbon atoms and having one or more heteroatoms in its ring system which are each independently selected from O, N and S; and wherein the one or more optional substituents for each of said aryl and heteroaryl groups are each independently selected from the following groups: $C_{1-6}$ alkyl, $C_{2-6}$ alkenyl, $C_{2-6}$ alkynyl, $C_{3-7}$ cyclic alkyl, halo, —OH, —OR$^8$, —OC(O)R$^8$, —OC(O)NH$_2$, —OC(O)NHR$^8$, —OC(O)NR$^8$R$^8$, —OP(O)(OH)$_2$, —OP(O)(OR$^8$)$_2$, —NO$_2$, —NH$_2$, —NHR$^8$, —NR$^8$R$^8$, —N$^+$(O$^-$)R$^8$R$^8$, —NHC(O)H, —NHC(O)R$^8$, —NR$^8$C(O)R$^8$, —NHC(O)NH$_2$, —NHC(O)NR$^8$R$^8$, —NR$^8$C(O)NHR$^8$, —SH, —SR$^8$, —S(O)H, —S(O)R$^8$, —SO$_2$R$^8$, —SO$_2$NH$_2$, —SO$_2$NHR$^8$, —SO$_2$NR$^8$R$^8$, —CF$_3$, —OCF$_3$, —OCHF$_2$, —CN, —CO$_2$H, —CO$_2$R$^8$, —CHO, —C(O)R$^8$, —C(O)NH$_2$, —C(O)NHR$^8$, —C(O)NR$^8$R$^8$, —CONHSO$_2$H, —C(O)NHSO$_2$R$^8$, and —C(O)NR$^8$SO$_2$R$^8$; wherein each R$^5$, R$^7$ and R$^8$ is independently selected from a $C_{1-6}$ alkyl group, a $C_{2-6}$ alkenyl group, a $C_{2-6}$ alkynyl group and a $C_{3-7}$ cyclic alkyl group; and
(b) an optionally substituted aryl, and an optionally substituted heteroaryl group having up to 12 carbon atoms and having one or more heteroatoms in its ring system which are each independently selected from O, N and S; and wherein the one or more optional substituents for each aryl and heteroaryl are each independently selected from the same optional substituents as those defined in (a) above for R;

R$^9$ and R$^{10}$ are each independently selected from the following groups defined in paragraphs (a) and (b) below:
(a) H, an optionally substituted $C_{1-6}$ alkyl group, an optionally substituted $C_{2-6}$ alkenyl group, an optionally substituted $C_{2-6}$ alkynyl group, and an optionally substituted $C_{3-7}$ cyclic alkyl group; wherein the one or more optional substituents for each of said alkyl, alkenyl, alkynyl and cyclic alkyl are each independently selected from the following groups: halo, —OH, —OR$^{11}$, —OC(O)R$^1$, —OC(O)NH$_2$, —OC(O)NHR$^{11}$, —OC(O)NR$^{11}$R$^{11}$, —OP(O)(OH)$_2$, —OP(O)(OR$^{11}$)$_2$, —NO$_2$, —NH$_2$, —NHR$^{11}$, —NR$^{11}$R$^{11}$, —N$^+$(O)R$^{11}$R$^{11}$, —NHC(O)H, —NHC(O)R$^{11}$, —NR$^{11}$C(O)R$^{11}$, —NHC(O)NH$_2$, —NHC(O)NR$^{11}$R$^{11}$, —NR$^{11}$C(O)NHR, —SH, —SR$^{11}$, —S(O)H, —S(O)R$^{11}$, —SO$_2$R$^{11}$, —SO$_2$NH$_2$, —SO$_2$NHR$^{11}$, —SO$_2$NR$^{11}$R$^{11}$, —CF$_3$, —OCF$_3$, —OCHF$_2$, —CN, —CO$_2$H, —CO$_2$R$^{11}$, —CHO, —C(O)R$^{11}$, —C(O)NH$_2$, —C(O)NHR$^{11}$, —C(O)NR$^{11}$R$^{11}$, —CONHSO$_2$H, —C(O)NHSO$_2$R$^{11}$, —C(O)NR$^{11}$SO$_2$R$^{11}$, cyclic $C_3$-$C_7$ alkylamino, imidazolyl, piperazinyl, morpholinyl, thiomorpholinyl, piperidinyl, azepanyl, pyrrolidinyl and azetidinyl; wherein each of the groups cyclic $C_3$-$C_7$ alkylamino, imidazolyl, piperazinyl, morpholinyl, thiomorpholinyl, piperidinyl, azepanyl, pyrrolidinyl and azetidinyl are optionally substituted by one or more of the following groups: $C_{1-6}$ alkyl, $C_{2-6}$ alkenyl, $C_{2-6}$ alkynyl, $C_{3-7}$ cyclic alkyl, halo, —OH, —OR$^{13}$, —OC(O)R$^{13}$, —OC(O)NH$_2$, —OC(O)NHR$^{13}$, —OC(O)NR$^{13}$R$^{13}$, —OP(O)(OH)$_2$, —OP(O)(OR$^{13}$)$_2$, —NO$_2$, —NH$_2$, —NHR$^{13}$, —NR$^{13}$R$^{13}$—N$^+$(O)R$^{13}$R$^{13}$, —NHC(O)H, —NHC(O)R$^{13}$, —NR$^{13}$C(O)R$^{13}$, —NHC(O)NH$_2$, —NHC(O)NR$^{13}$R$^{13}$, —NR$^{13}$C(O)NHR$^{13}$, —SH, —SR$^{13}$, —S(O)H, —S(O)R$^{13}$, —SO$_2$R$^{13}$, —SO$_2$NH$_2$, —SO$_2$NHR$^{13}$, —SO$_2$NR$^{13}$R$^{13}$, —CF$_3$, —OCF$_3$, —OCHF$_2$, —CN, —CO$_2$H, —CO$_2$R$^{13}$, —CHO, —C(O)R$^{13}$, —C(O)NH$_2$, —C(O)NHR$^{13}$, —C(O)NR$^{13}$R$^{13}$, —CONHSO$_2$H, —C(O)NHSO$_2$R$^{13}$, and —C(O)NR$^{13}$SO$_2$R$^{13}$; wherein each R$^{11}$ and R$^{13}$ is independently selected from a $C_{1-6}$ alkyl group, a $C_{2-6}$ alkenyl group, a $C_{2-6}$ alkynyl group and a $C_{3-7}$ cyclic alkyl group; and
(b) an optionally substituted aryl, and an optionally substituted heteroaryl group having up to 12 carbon atoms and having one or more heteroatoms in its ring system which are each independently selected from O, N and S; and wherein the one or more optional substituents for each of said aryl and heteroaryl are each independently selected from the same optional substituents as those defined in (a) above for R$^9$ and R$^{10}$; or
(c) R$^9$ and R$^{10}$ taken together can form a partially saturated or a fully unsaturated 5- or 6-membered ring of carbon atoms optionally including 1 to 3 heteroatoms selected from O, N and S, and the ring can be optionally substituted independently with 1 to 5 substituents selected from the same optional substituents as those defined in (a) above for R$^9$ and R$^{10}$.

(3). A compound as defined in paragraph (1) or (2), wherein when $R^9$ and $R^{10}$ are each independently selected from the following groups: an optionally substituted $C_{1-6}$ alkyl group, an optionally substituted $C_{2-6}$ alkenyl group, an optionally substituted $C_{2-6}$ alkynyl group, and an optionally substituted $C_{3-7}$ cyclic alkyl group; then the one or more optional substituents for each of said alkyl, alkenyl, alkynyl and cyclic alkyl are each independently selected from the following groups: halo, —OH, —$OR^{11}$, —$OC(O)R^{11}$, —$OC(O)NH_2$, —$OC(O)NHR^{11}$, —$OC(O)NR^{11}R^{11}$, —$OP(O)(OH)_2$, —$OP(O)(OR^{11})_2$, —$NO_2$, —$NH_2$, —$NHR^{11}$, —$NR^{11}R^{11}$, —$N^+(O)R^{11}R^{11}$, —$NHC(O)H$, —$NHC(O)R^{11}$, —$NR^{11}C(O)R^{11}$, —$NHC(O)NH_2$, —$NHC(O)NR^{11}R^{11}$, —$NR^{11}C(O)NHR^{11}$, —SH, —$SR^1$, —$S(O)H$, —$S(O)R^{11}$, —$SO_2R^{11}$, —$SO_2NH_2$, —$SO_2NHR^{11}$, —$SO_2NR^{11}R^{11}$, —$CF_3$, —$CHF_2$, —$CH_2F$, —$OCF_3$, —$OCHF_2$, —CN, —$CO_2H$, —$CO_2R^{11}$, —CHO, —$C(O)R^{11}$, —$C(O)NH_2$, —$C(O)NHR^{11}$, —$C(O)NR^{11}R^{11}$, —$CONHSO_2H$, —$C(O)NHSO_2R^{11}$, and —$C(O)NR^{11}SO_2R^{11}$; wherein each $R^{11}$ is independently selected from a $C_{1-6}$ alkyl group, a $C_{2-6}$ alkenyl group, a $C_{2-6}$ alkynyl group and a $C_{3-7}$ cyclic alkyl group.

(4). A compound as defined in any one of paragraphs (1) to (3), wherein Z is N or N-oxide, such as N, W is $CR^1$, X is $CR^2$ and Y is $CR^3$.

(5). A compound as defined in any one of paragraphs (1) to (3), wherein X is N or N-oxide, such as N, W is $CR^1$, Y is $CR^3$ and Z is $CR^4$.

(6). A compound as defined in any one of paragraphs (1) to (3), wherein X and Z are both N or N-oxide, such as N, W is $CR^1$ and Y is $CR^3$.

(7). A compound as defined in any one of paragraphs (1) to (6), wherein $R^1$, $R^2$, $R^3$ and $R^4$, where present, are each independently selected from the group consisting of H, halo, optionally substituted $C_1$-$C_6$ alkyl, —O—R wherein R is optionally substituted $C_1$-$C_6$ alkyl, an optionally substituted aryl, such as substituted phenyl, and an optionally substituted heteroaryl group having up to 12 carbon atoms and having one or more heteroatoms in its ring system which are each independently selected from O, N and S.

(8). A compound as defined in any one of paragraphs (1) to (6), wherein $R^1$, $R^2$, $R^3$ and $R^4$, where present, are each independently selected from the group consisting of H, halo, optionally substituted $C_1$-$C_6$ alkyl, —O—R wherein R is selected from optionally substituted $C_1$-$C_6$ alkyl and optionally substituted aryl (such as phenyl), —NHR wherein R is optionally substituted aryl, an optionally substituted aryl, and an optionally substituted heteroaryl group having up to 12 carbon atoms and having one or more heteroatoms in its ring system which are each independently selected from O, N and S.

(9). A compound as defined in paragraph (8), wherein $R^1$, $R^2$, $R^3$ and $R^4$, where present, are each independently selected from the group consisting of H, halogen, —$CF_3$, —$CHF_2$, —$OCF_3$, —$OCHF_2$, $C_{1-6}$ alkyl, such as methyl, substituted aryl, substituted heteroaryl, —OR wherein R is optionally substituted aryl, and —NHR wherein R is optionally substituted aryl.

(10). A compound as defined in paragraph (8), wherein one or two of $R^1$, $R^2$, $R^3$ and $R^4$, where present, is H, and the others of $R^1$, $R^2$ $R^3$ and $R^4$ that are not H are independently selected from the group consisting of halogen, —$CF_3$, —$CHF_2$, —$OCF_3$, —$OCHF_2$, $C_{1-6}$ alkyl, such as methyl, substituted aryl, substituted heteroaryl, —OR wherein R is optionally substituted aryl, and —NHR wherein R is optionally substituted aryl.

(11). A compound as defined in any one of paragraphs (8) to (10), wherein $R^3$ is present and selected from the group consisting of halogen, —OR wherein R is optionally substituted aryl, and —NHR wherein R is optionally substituted aryl.

(12). A compound as defined in paragraph (4), wherein Z is N or N-oxide, such as N, W is $CR^1$, X is $CR^2$ and Y is $CR^3$, and $R^3$ is selected from the group consisting of halogen, —O—R wherein R is optionally substituted aryl, and —NHR wherein R is optionally substituted aryl.

(13). A compound as defined in paragraph (4), wherein Z is N or N-oxide, such as N, W is $CR^1$, X is $CR^2$ and Y is $CR^3$, $R^1$ is H, and one or both of $R^2$ and $R^3$ are other than H, for example, both $R^2$ and $R^3$ are other than H, or $R^2$ is H and $R^3$ is other than H, or $R^3$ is H and $R^2$ is other than H.

(14). A compound as defined in paragraph (13), wherein each of $R^2$ and $R^3$ that is other than H is independently selected from the group consisting of halogen, optionally substituted $C_1$-$C_6$ alkyl, —OR wherein R is selected from optionally substituted $C_1$-$C_6$ alkyl and optionally substituted aryl, —NHR wherein R is optionally substituted aryl; an optionally substituted aryl, such as substituted phenyl, and an optionally substituted heteroaryl group.

(15). A compound as defined in paragraph (14), wherein each of $R^2$ and $R^3$ that is other than H is independently selected from the group consisting of halogen, —$CF_3$, —$CHF_2$, —$OCF_3$, —$OCHF_2$, $C_{1-6}$ alkyl such as methyl, substituted aryl, substituted heteroaryl, —OR wherein R is optionally substituted aryl, and —NHR wherein R is optionally substituted aryl.

(16). A compound as defined in any one of paragraphs (1) to (6), wherein $R^1$ and $R^2$ taken together, or $R^2$ and $R^3$ taken together, or $R^3$ and $R^4$ taken together form a saturated or a partially saturated or a fully unsaturated 5- or 6-membered ring of carbon atoms optionally including 1 to 3 heteroatoms selected from O, N or S and the ring is optionally substituted with 1 to 4 substituents independently selected from R, and those of $R^1$, $R^2$, $R^3$ and $R^4$ that are not part of the ring, are independently selected from: H, halo, optionally substituted $C_1$-$C_6$ alkyl, O—R wherein R is optionally substituted $C_1$-$C_6$ alkyl, an optionally substituted aryl and an optionally substituted heteroaryl group having up to 12 carbon atoms and having one or more heteroatoms in its ring system which are each independently selected from O, N and S.

(17). A compound as defined in any one of paragraphs (1) to (16), wherein $R^9$ and $R^{10}$ are independently selected from H, an optionally substituted $C_{1-6}$ alkyl group, an optionally substituted aryl, such as substituted phenyl, and an optionally substituted heteroaryl group having up to 12 carbon atoms and having one or more heteroatoms in its ring system which are each independently selected from O, N and S.

(18). A compound as defined in any one of paragraphs (1) to (17), wherein $R^9$ and $R^{10}$ are both H.

(19). A compound as defined in paragraph (4), wherein Z is N or N-oxide, such as N, W is $CR^1$, X is $CR^2$ and Y is $CR^3$, and $R^9$ and $R^{10}$ are both H.

(20) A compound as defined in paragraph (19), wherein $R^1$, $R^2$ and $R^3$ are each independently selected from the group consisting of H, halogen, —$CF_3$, —$CHF_2$, —$OCF_3$, —$OCHF_2$, $C_{1-6}$ alkyl, such as methyl, substituted aryl, substituted heteroaryl, —OR wherein R is optionally substituted aryl, and —NHR wherein R is optionally substituted aryl.

(21). A compound as defined in paragraph (19), wherein $R^1$, $R^2$ and $R^3$ are each independently selected from the group consisting of H, halogen, $C_{1-6}$ alkyl, such as methyl, substituted aryl, and substituted heteroaryl.

(22). A compound as defined in paragraph (19), wherein one or two of $R^1$, $R^2$ and $R^3$ is H, and the others of $R^1$, $R^2$ and $R^3$ that are not H are independently selected from the group consisting of halogen, —$CF_3$, —$CHF_2$, —$OCF_3$, —$OCHF_2$, $C_{1-6}$ alkyl, such as methyl, substituted aryl, substituted heteroaryl, —OR wherein R is optionally substituted aryl, and —NHR wherein R is optionally substituted aryl.

(23). A compound as defined in paragraph (19), wherein $R^1$ is H, and one of both of $R^2$ and $R^3$ is other than H, wherein each of $R^2$ and $R^3$ that is not H is independently selected from the group consisting of halogen, —$CF_3$, —$CHF_2$, —$OCF_3$, —$OCHF_2$, $C_{1-6}$ alkyl, such as methyl, substituted aryl, substituted heteroaryl, —OR wherein R is optionally substituted aryl, and —NHR wherein R is optionally substituted aryl.

(24). A compound as defined in any one of paragraphs (19) to (23), wherein $R^3$ is selected from the group consisting of halogen, —OR wherein R is optionally substituted aryl, and —NHR wherein R is optionally substituted aryl.

(25). A compound as defined in paragraph (19), wherein $R^1$ is H, and $R^2$ and $R^3$ form a saturated or a partially saturated or a fully unsaturated 5- or 6-membered ring of carbon atoms optionally including 1 to 3 heteroatoms selected from O, N and S and the ring is optionally substituted with 1 to 4 substituents independently selected from R.

(26). A compound as defined in paragraph (1), selected from the group consisting of:

5-Bromo-4,6-dimethylisoxazolo[5,4-b]pyridin-3-amine (1)
Isoxazolo[5,4-b]pyridin-3-amine (2)
5-Chloro-4,6-dimethylisoxazolo[5,4-b]pyridin-3-amine (3)
4,6-Dimethylisoxazolo[5,4-b]pyridin-3-amine (4)
4,5,6-Trimethylisoxazolo[5,4-b]pyridin-3-amine (5)
5-Bromoisoxazolo[5,4-b]pyridin-3-amine (6)
6-Methylisoxazolo[5,4-b]pyridin-3-amine (7)
5-Chloroisoxazolo[5,4-b]pyridin-3-amine (8)
Isoxazolo[5,4-b]quinolin-3-amine (9)
5,6,7,8-Tetrahydroisoxazolo[5,4-b]quinolin-3-amine (10)
6-Chloroisoxazolo[5,4-b]pyridin-3-amine (11)
Isoxazolo[5,4-d]pyrimidin-3-amine (12)
4-Phenylisoxazolo[5,4-b]pyridin-3-amine (13)
5-Fluoroisoxazolo[5,4-b]pyridin-3-amine (14)
6-Phenylisoxazolo[5,4-b]pyridin-3-amine (15)
5-Iodoisoxazolo[5,4-b]pyridin-3-amine (16)
Isoxazolo[4,5-c]pyridin-3-amine (17)
$N^6,N^6$-Dimethylisoxazolo[5,4-b]pyridine-3,6-diamine (18)
$N^4,N^4$-Dimethylisoxazolo[5,4-b]pyridine-3,4-diamine (19)
5-Chloro-$N^3$,4,6-trimethylisoxazolo[5,4-b]pyridin-3-amine (20)
5-Chloro-$N^3,N^3$,4,6-tetramethylisoxazolo[5,4-b]pyridin-3-amine (21)
5-(3-Methoxyphenyl)isoxazolo[5,4-b]pyridin-3-amine (22)
5-(2-Methoxyphenyl)isoxazolo[5,4-b]pyridin-3-amine (23)
5-Phenylisoxazolo[5,4-b]pyridin-3-amine (24)
5-(3-Fluoro-4-methoxyphenyl)isoxazolo[5,4-b]pyridin-3-amine (25)
5-(Pyridin-3-yl)isoxazolo[5,4-b]pyridin-3-amine (26)
5-(Pyridin-4-yl)isoxazolo[5,4-b]pyridin-3-amine (27)
2-(3-Aminoisoxazolo[5,4-b]pyridin-5-yl)phenol (28)
4-(3-Aminoisoxazolo[5,4-b]pyridin-5-yl)phenol (29)
5-(4-Fluorophenyl)isoxazolo[5,4-b]pyridin-3-amine (30)
5-(3-Fluorophenyl)isoxazolo[5,4-b]pyridin-3-amine (31)
5-(2,4-difluorophenyl)isoxazolo[5,4-b]pyridin-3-amine (32)
5-(3,5-Difluoro-2-methoxyphenyl)isoxazolo[5,4-b]pyridin-3-amine (33)
5-(2,4-Dichlorophenyl)isoxazolo[5,4-b]pyridin-3-amine (34)
5-(2,3,4-Trichlorophenyl)isoxazolo[5,4-b]pyridin-3-amine (35)
5-(4-(Trifluoromethylphenyl)isoxazolo[5,4-b]pyridin-3-amine (36)
5-(3-Aminophenyl)isoxazolo[5,4-b]pyridin-3-amine (37)
Methyl 3-(3-aminoisoxazolo[5,4-b]pyridin-5-yl)benzoate (38)
5-(6-Fluoropyridin-3-yl)isoxazolo[5,4-b]pyridin-3-amine (39)
5-(2-Chloro-4-(trifluoromethyl)phenyl)isoxazolo[5,4-b]pyridin-3-amine (40)
6-Methoxyisoxazolo[5,4-b]pyridin-3-amine (41)
6-Chloro-4-methylisoxazolo[5,4-b]pyridin-3-amine (42)
Isoxazolo[5,4-b]pyridine-3,6-diamine (43)
5-Methylisoxazolo[5,4-b]pyridin-3-amine (44)
5,6-Dimethylisoxazolo[5,4-b]pyridin-3-amine (45)
6-Methyl-4-(trifluoromethyl)isoxazolo[5,4-b]pyridin-3-amine (46)
6-(Trifluoromethyl)isoxazolo[5,4-b]pyridin-3-amine (47)
6-Isopropylisoxazolo[5,4-b]pyridin-3-amine (48)
5-Nitroisoxazolo[5,4-b]pyridin-3-amine (49)
Ethyl 3-amino-6-(trifluoromethyl)isoxazolo[5,4-b]pyridine-5-carboxylate (50)
4-Methoxyisoxazolo[5,4-b]pyridin-3-amine (51)
5-(Difluoromethoxy)-4,6-dimethylisoxazolo[5,4-b]pyridin-3-amine (52)
Ethyl 3-amino-6-methylisoxazolo[5,4-b]pyridine-5-carboxylate (53)
Ethyl 3-amino-6-(difluoromethyl)isoxazolo[5,4-b]pyridine-5-carboxylate (54)
5-Fluoro-6-morpholinoisoxazolo[5,4-b]pyridin-3-amine (55)
N6-Cyclopropyl-5-fluoroisoxazolo[5,4-b]pyridine-3,6-diamine (56)
5-Fluoro-N6,N6-dimethylisoxazolo[5,4-b]pyridine-3,6-diamine (57)
6-(Furan-2-yl)isoxazolo[5,4-b]pyridin-3-amine (58)
6,7-Dihydro-5H-cyclopenta[b]isoxazolo[4,5-e]pyridin-3-amine (59)
6,7,8,9-Tetrahydro-5H-cyclohepta[b]isoxazolo[4,5-e]pyridin-3-amine (60)
6,6-Dimethyl-5,6,7,8-tetrahydroisoxazolo[5,4-b]quinolin-3-amine (61)
7,8-Dihydro-5H-isoxazolo[5,4-b]pyrano[3,4-e]pyridin-3-amine (62)
6-(Methylthio)isoxazolo[5,4-d]pyrimidin-3-amine (63)
6-Methylisoxazolo[5,4-d]pyrimidin-3-amine (64)
4-(Methylthio)-6-phenylisoxazolo[5,4-d]pyrimidin-3-amine (65)
6-Chloro-5-fluoroisoxazolo[5,4-b]pyridin-3-amine (66)
5,6-Dichloroisoxazolo[5,4-b]pyridin-3-amine (67)
6-Chloro-4-(trifluoromethyl)isoxazolo[5,4-b]pyridin-3-amine (68)

5-(3-Methoxyprop-1-yn-1-yl)isoxazolo[5,4-b]pyridin-3-amine (69)
6-(4-Methoxyphenyl)isoxazolo[5,4-b]pyridin-3-amine (70)
6-(4-Fluorophenyl)isoxazolo[5,4-b]pyridin-3-amine (71)
6-(2,4-Dichlorophenyl)isoxazolo[5,4-b]pyridin-3-amine (72)
6-(2,4-Difluorophenyl)isoxazolo[5,4-b]pyridin-3-amine (73)
6-(2-Thienyl)isoxazolo[5,4-b]pyridin-3-amine (74)
6-(1-Methyl-1H-pyrazol-5-yl)isoxazolo[5,4-b]pyridin-3-amine (75)
6-(3-(Dimethylamino)propoxy)isoxazolo[5,4-b]pyridin-3-amine (76)
6-(2-(Dimethylamino)ethoxy)isoxazolo[5,4-b]pyridin-3-amine(77)
6-(2-Morpholinoethoxy)isoxazolo[5,4-b]pyridin-3-amine (78)
6-(Methylthio)isoxazolo[5,4-b]pyridin-3-amine (79)
6-(Methylsulfonyl)isoxazolo[5,4-b]pyridin-3-amine (80)
3-Aminoisoxazolo[5,4-b]pyridine-6-carboxylic acid (81)
Methyl 3-aminoisoxazolo[5,4-b]pyridine-6-carboxylate (82)
6-Phenoxyisoxazolo[5,4-b]pyridin-3-amine (83)
6-(2-Chlorophenoxy)isoxazolo[5,4-b]pyridin-3-amine (84)
6-(3-Chlorophenoxy)isoxazolo[5,4-b]pyridin-3-amine (85)
6-(4-Chlorophenoxy)isoxazolo[5,4-b]pyridin-3-amine (86)
6-(2-(Trifluoromethoxy)phenoxy)isoxazolo[5,4-b]pyridin-3-amine (87)
6-(3-(Trifluoromethoxy)phenoxy)isoxazolo[5,4-b]pyridin-3-amine (88)
6-(4-(Trifluoromethoxy)phenoxy)isoxazolo[5,4-b]pyridin-3-amine (89)
6-(2-Methoxyphenoxy)isoxazolo[5,4-b]pyridin-3-amine (90)
6-(3-Methoxyphenoxy)isoxazolo[5,4-b]pyridin-3-amine (91)
6-(4-Methoxyphenoxy)isoxazolo[5,4-b]pyridin-3-amine (92)
6-(3-(Trifluoromethyl)phenoxy)isoxazolo[5,4-b]pyridin-3-amine (93)
$N^6$-Phenylisoxazolo[5,4-b]pyridine-3,6-diamine (94)
$N^6$-(3-Methoxyphenyl)isoxazolo[5,4-b]pyridine-3,6-diamine (95) and
$N^6$-(4-Methoxyphenyl)isoxazolo[5,4-b]pyridine-3,6-diamine (96),
and pharmaceutically acceptable salts thereof.
(27). A compound as defined in any one of the preceding paragraphs (1) to (26), wherein the compound is not 5-Phenylisoxazolo[5,4-b]pyridin-3-amine.
(28). A compound as defined in any one of the preceding paragraphs (1) to (27), wherein the compound is an IDO1 inhibitor.
(29). A compound as defined in any one of the preceding paragraphs (1) to (27), wherein the compound is a TDO inhibitor.
(30). A compound as defined in any one of the preceding paragraphs (1) to (27), wherein the compound is both an IDO1 inhibitor and a TDO inhibitor.

Certain compounds of the Formula I are novel. Accordingly, such compounds are provided as a further feature of the invention. By way of example, the invention further provides a compound of Formula I selected from the following:
5-Bromo-4,6-dimethylisoxazolo[5,4-b]pyridin-3-amine (1)
4,5,6-Trimethylisoxazolo[5,4-b]pyridin-3-amine (5)
5-Chloroisoxazolo[5,4-b]pyridin-3-amine (8)
4-Phenylisoxazolo[5,4-b]pyridin-3-amine (13)
5-Fluoroisoxazolo[5,4-b]pyridin-3-amine (14)
6-Phenylisoxazolo[5,4-b]pyridin-3-amine (15)
5-Iodoisoxazolo[5,4-b]pyridin-3-amine (16)
$N^6,N^6$-Dimethylisoxazolo[5,4-b]pyridine-3,6-diamine (18)
$N^4,N^4$-Dimethylisoxazolo[5,4-b]pyridine-3,4-diamine (19)
5-Chloro-$N^3$,4,6-trimethylisoxazolo[5,4-b]pyridin-3-amine (20)
5-Chloro-$N^3,N^3$,4,6-tetramethylisoxazolo[5,4-b]pyridin-3-amine (21)
5-(3-Methoxyphenyl)isoxazolo[5,4-b]pyridin-3-amine (22)
5-(2-Methoxyphenyl)isoxazolo[5,4-b]pyridin-3-amine (23)
5-(3-Fluoro-4-methoxyphenyl)isoxazolo[5,4-b]pyridin-3-amine (25)
5-(Pyridin-3-yl)isoxazolo[5,4-b]pyridin-3-amine (26)
5-(Pyridin-4-yl)isoxazolo[5,4-b]pyridin-3-amine (27)
2-(3-Aminoisoxazolo[5,4-b]pyridin-5-yl)phenol (28)
4-(3-Aminoisoxazolo[5,4-b]pyridin-5-yl)phenol (29)
5-(4-Fluorophenyl)isoxazolo[5,4-b]pyridin-3-amine (30)
5-(3-Fluorophenyl)isoxazolo[5,4-b]pyridin-3-amine (31)
5-(2,4-difluorophenyl)isoxazolo[5,4-b]pyridin-3-amine (32)
5-(3,5-Difluoro-2-methoxyphenyl)isoxazolo[5,4-b]pyridin-3-amine (33)
5-(2,4-Dichlorophenyl)isoxazolo[5,4-b]pyridin-3-amine (34)
5-(2,3,4-Trichlorophenyl)isoxazolo[5,4-b]pyridin-3-amine (35)
5-(4-(Trifluoromethylphenyl)isoxazolo[5,4-b]pyridin-3-amine (36)
5-(3-Aminophenyl)isoxazolo[5,4-b]pyridin-3-amine (37)
Methyl 3-(3-aminoisoxazolo[5,4-b]pyridin-5-yl)benzoate (38)
5-(6-Fluoropyridin-3-yl)isoxazolo[5,4-b]pyridin-3-amine (39)
5-(2-Chloro-4-(trifluoromethyl)phenyl)isoxazolo[5,4-b]pyridin-3-amine (40)
6-Chloro-4-methylisoxazolo[5,4-b]pyridin-3-amine (42)
Isoxazolo[5,4-b]pyridine-3,6-diamine (43)
5-Methylisoxazolo[5,4-b]pyridin-3-amine (44)
5,6-Dimethylisoxazolo[5,4-b]pyridin-3-amine (45)
6-Methyl-4-(trifluoromethyl)isoxazolo[5,4-b]pyridin-3-amine (46)
6-Isopropylisoxazolo[5,4-b]pyridin-3-amine (48)
5-Nitroisoxazolo[5,4-b]pyridin-3-amine (49)
Ethyl 3-amino-6-(trifluoromethyl)isoxazolo[5,4-b]pyridine-5-carboxylate (50)
4-Methoxyisoxazolo[5,4-b]pyridin-3-amine (51)
5-(Difluoromethoxy)-4,6-dimethylisoxazolo[5,4-b]pyridin-3-amine (52)
Ethyl 3-amino-6-methylisoxazolo[5,4-b]pyridine-5-carboxylate (53)
Ethyl 3-amino-6-(difluoromethyl)isoxazolo[5,4-b]pyridine-5-carboxylate (54)
5-Fluoro-6-morpholinoisoxazolo[5,4-b]pyridin-3-amine (55)
N6-Cyclopropyl-5-fluoroisoxazolo[5,4-b]pyridine-3,6-diamine (56)
5-Fluoro-N6,N6-dimethylisoxazolo[5,4-b]pyridine-3,6-diamine (57)
6-(Furan-2-yl)isoxazolo[5,4-b]pyridin-3-amine (58)
6,7,8,9-Tetrahydro-5H-cyclohepta[b]isoxazolo[4,5-e]pyridin-3-amine (60)
6,6-Dimethyl-5,6,7,8-tetrahydroisoxazolo[5,4-b]quinolin-3-amine (61)
7,8-Dihydro-5H-isoxazolo[5,4-b]pyrano[3,4-e]pyridin-3-amine (62)
6-(Methylthio)isoxazolo[5,4-d]pyrimidin-3-amine (63)

4-(Methylthio)-6-phenylisoxazolo[5,4-d]pyrimidin-3-amine (65)
6-Chloro-5-fluoroisoxazolo[5,4-b]pyridin-3-amine (66)
5,6-Dichloroisoxazolo[5,4-b]pyridin-3-amine (67)
6-Chloro-4-(trifluoromethyl)isoxazolo[5,4-b]pyridin-3-amine (68)
5-(3-Methoxyprop-1-yn-1-yl)isoxazolo[5,4-b]pyridin-3-amine (69)
6-(4-Methoxyphenyl)isoxazolo[5,4-b]pyridin-3-amine (70)
6-(4-Fluorophenyl)isoxazolo[5,4-b]pyridin-3-amine (71)
6-(2,4-Dichlorophenyl)isoxazolo[5,4-b]pyridin-3-amine (72)
6-(2,4-Difluorophenyl)isoxazolo[5,4-b]pyridin-3-amine (73)
6-(2-Thienyl)isoxazolo[5,4-b]pyridin-3-amine (74)
6-(1-Methyl-1H-pyrazol-5-yl)isoxazolo[5,4-b]pyridin-3-amine (75)
6-(3-(Dimethylamino)propoxy)isoxazolo[5,4-b]pyridin-3-amine (76)
6-(2-(Dimethylamino)ethoxy)isoxazolo[5,4-b]pyridin-3-amine(77)
6-(2-Morpholinoethoxy)isoxazolo[5,4-b]pyridin-3-amine (78)
6-(Methylthio)isoxazolo[5,4-b]pyridin-3-amine (79)
6-(methylsulfonyl)isoxazolo[5,4-b]pyridin-3-amine (80)
3-Aminoisoxazolo[5,4-b]pyridine-6-carboxylic acid (81)
Methyl 3-aminoisoxazolo[5,4-b]pyridine-6-carboxylate (82)
6-Phenoxyisoxazolo[5,4-b]pyridin-3-amine (83)
6-(2-Chlorophenoxy)isoxazolo[5,4-b]pyridin-3-amine (84)
6-(3-Chlorophenoxy)isoxazolo[5,4-b]pyridin-3-amine (85)
6-(4-Chlorophenoxy)isoxazolo[5,4-b]pyridin-3-amine (86)
6-(2-(Trifluoromethoxy)phenoxy)isoxazolo[5,4-b]pyridin-3-amine (87)
6-(3-(Trifluoromethoxy)phenoxy)isoxazolo[5,4-b]pyridin-3-amine (88)
6-(4-(Trifluoromethoxy)phenoxy)isoxazolo[5,4-b]pyridin-3-amine (89)
6-(2-Methoxyphenoxy)isoxazolo[5,4-b]pyridin-3-amine (90)
6-(3-Methoxyphenoxy)isoxazolo[5,4-b]pyridin-3-amine (91)
6-(4-Methoxyphenoxy)isoxazolo[5,4-b]pyridin-3-amine (92)
6-(3-(Trifluoromethyl)phenoxy)isoxazolo[5,4-b]pyridin-3-amine (93)
$N^6$-Phenylisoxazolo[5,4-b]pyridine-3,6-diamine (94)
$N^6$-(3-Methoxyphenyl)isoxazolo[5,4-b]pyridine-3,6-diamine (95)
$N^6$-(4-Methoxyphenyl)isoxazolo[5,4-b]pyridine-3,6-diamine (96),
and pharmaceutically acceptable salts thereof.

Other aspects of the invention may include suitable combinations of embodiments disclosed herein. Also, as will be appreciated by one of skill in the art, features and preferred embodiments of one aspect of the invention will also pertain to other aspects of the invention.

While the invention is broadly as defined above, it is not limited thereto and also includes embodiments of which the following description provides examples. The invention will now be described in more detail.

DETAILED DESCRIPTION OF THE INVENTION

Definitions

Figure 1:
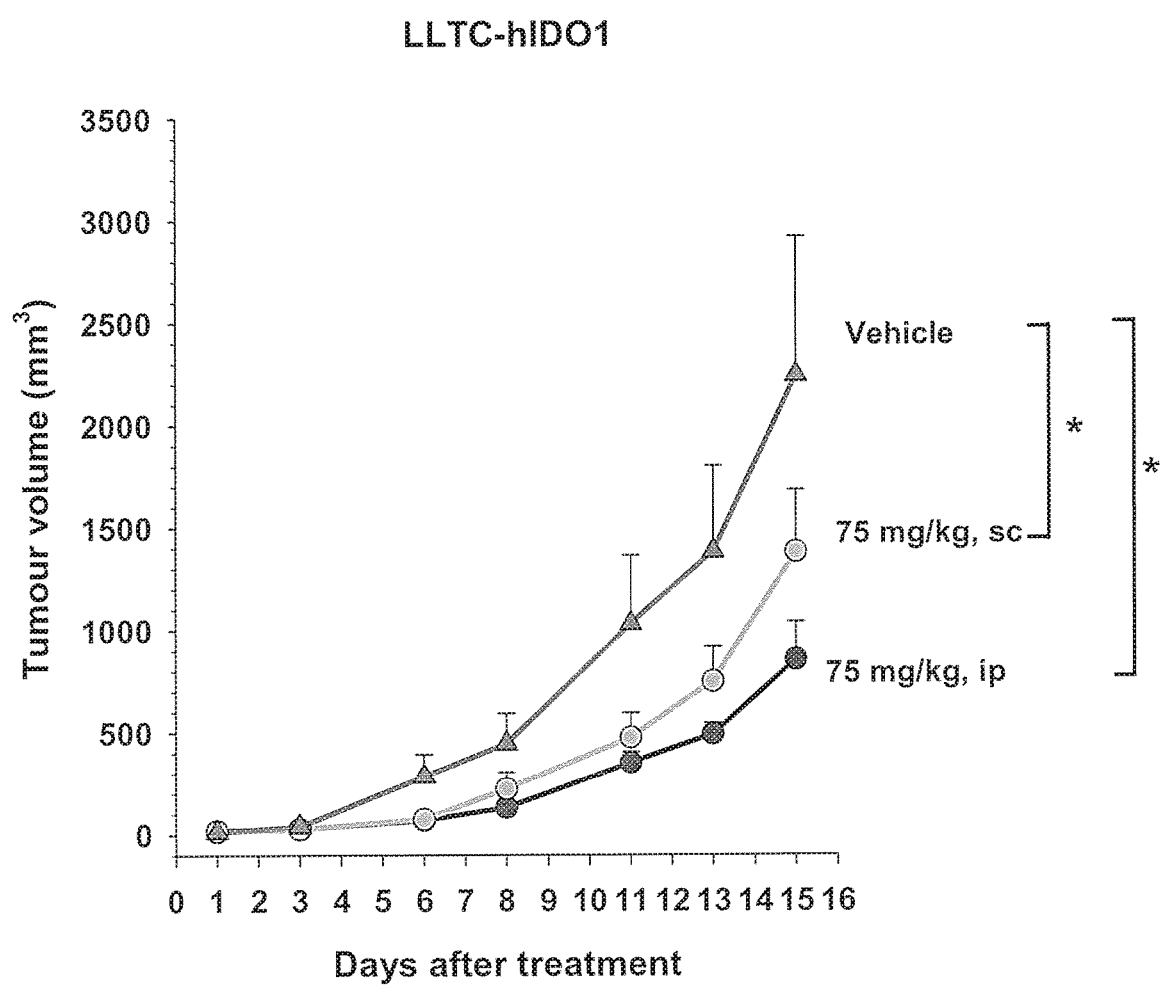
FIG. 1 shows tumour volume from 0 to 16 days after treatment, for C57/Bl mice inoculated sc with Lewis lung carcinoma cells transfected to express hIDO1, followed by treatment, when tumours were palpable, with Compound 3 daily at 75 mg/kg either ip or sc. Tumours were measured every second day until humane ethical endpoint was reached. Tumour volume is in $mm^3$. N=7 per group. *Indicates significance by repeated measures one-way Anova.

As used herein, the term "radiotherapy" means the use of high-energy radiation from x-rays, gamma rays, neutrons, protons, and other sources to kill cancer cells and shrink tumors. Radiation may come from a machine outside the body (external-beam radiation therapy), or it may come from radioactive material placed in the body near cancer cells (internal radiation therapy). Systemic radiotherapy uses a radioactive substance, such as a radiolabeled monoclonal antibody, that travels in the blood to tissues throughout the body. The terms irradiation and radiation therapy have the same meaning.

It is to be recognised that certain compounds of the present invention may exist in one or more different enantiomeric or diastereomeric forms. It is to be understood that the enantiomeric or diastereomeric forms are included in the above aspects of the invention.

The term halo or halogen group used throughout the specification is to be taken as meaning a fluoro, chloro, bromo or iodo group.

It is to be understood that where variables of the Formula I as defined above are optionally substituted by one or more imidazolyl, piperazinyl, morpholinyl, thiomorpholinyl, piperidinyl, azepanyl, pyrrolidinyl and azetidinyl groups that the linkage to the relevant variable may be through either one of the available nitrogen or carbon ring atoms of these groups.

It is to be understood that the term "heteroaryl" includes both monocyclic and bicyclic ring systems, unless the context requires otherwise.

It is to be understood that the term "aryl" means an aromatic hydrocarbon such as phenyl or naphthyl.

It is to be understood that where a group is qualified as being "optionally substituted", this means that the group can be either (a) unsubstituted or (b) substituted by the defined substituents.

It is to be understood that where reference is made throughout the specification to a $C_1$-$C_6$ alkyl or $C_2$-$C_6$ alkenyl group, these groups may be unbranched or branched. For example, it is intended that reference to a $C_1$-$C_6$ alkyl would include a tert-butyl ($Me)_3C-$ group.

The expressions "treating cancer" and 'treatment of cancer" include methods that produce one or more anti-cancer effects which include, but are not limited to, anti-tumor effects, the response rate, the time to disease progression and the overall survival rate. "Anti-tumor" effects include but are not limited to inhibition of tumor growth, tumor growth delay, regression of tumor, shrinkage of tumor, increased time to regrowth of tumor on cessation of treatment and slowing of disease progression.

"Therapeutically effective amount" means an amount of a compound that, when administered to a subject for treating a cancer, is sufficient to effect such treatment for the cancer. The "effective amount" will vary depending on the cancer to be treated, the compound to be administered, the severity of the cancer treated, the age and relative health of the subject, the route and form of administration, whether the treatment is monotherapy or combination therapy, the judgement of the attending clinician, and other factors.

"Pharmaceutically acceptable" means: that which is useful in preparing a pharmaceutical composition that is generally safe, non-toxic, and neither biologically nor otherwise undesirable, and includes that which is acceptable for veterinary as well as human pharmaceutical use.

"Pharmaceutically acceptable salts" of a compound means salts that are pharmaceutically acceptable, as defined herein, and that possess the desired pharmacological activity of the parent compound. Such salts include:
(a) acid addition salts formed with inorganic acids such as hydrochloric acid, hydrobromic acid, sulfuric acid, nitric acid, phosphoric acid and the like; or formed with organic acids such as acetic acid, methanesulfonic acid, maleic acid, tartaric acid, citric acid and the like; and
(b) salts formed when an acidic proton present in the parent compound either is replaced by a metal ion, e.g. an alkali metal ion, an alkaline earth ion, or an aluminium ion; or coordinates with an organic or inorganic base. Acceptable organic bases include ethanolamine, diethanolamine, N-methylglucamine, triethanolamine and the like. Acceptable inorganic bases include aluminium hydroxide, calcium hydroxide, potassium hydroxide, sodium carbonate and sodium hydroxide.

"Warm blooded animal" means any member of the mammalia class including, but not limited to humans, non-human primates such as chimpanzees and other apes and monkey species, farm animals such as cattle, horses, sheep, goats, and swine; domestic animals such as rabbits, dogs and cats; laboratory animals including rodents, such as rats, mice and guinea pigs, and the like.

Compounds of the Invention and Methods of Preparing them

As defined above, in broad terms the invention relates to pharmaceutical compositions containing compounds of the general Formula I, and the use of such compounds in therapy, and in particular cancer therapy. Compounds of Formula I have been found to be inhibitors of indoleamine 2,3-dioxygenase 1 (IDO1) and/or tryptophan2,3-dioxygenase (TDO). As such, the compounds of the present invention are expected to be useful in cancer therapy, either alone or in combination with other agents, such as anti-cancer vaccines, modulators of immune checkpoint proteins, adoptive T cell immunotherapies (for example chimeric antigen receptor T cells (CART cells)), radiation therapy and other chemotherapeutic agents. The compounds of Formula I are also expected to be useful in the treatment of various other conditions besides cancer, as described in more detail in the Therapeutic Methods of the Invention section, below.

Certain methods for preparing compounds and pharmaceutically acceptable salts of the compounds of Formula I are described below, with reference to Methods 1 to 8.

Synthetic Schemes

Certain compounds of Formula I may be prepared by reaction of an appropriately substituted halo-cyano pyridine with acetohydroxamic acid, in the presence of a base such as potassium tert-butoxide, potassium carbonate or cesium carbonate (Method 1). A range of solvents may be used for this reaction, including DMF, p-dioxane and N-methylmorpholine.

Method 1

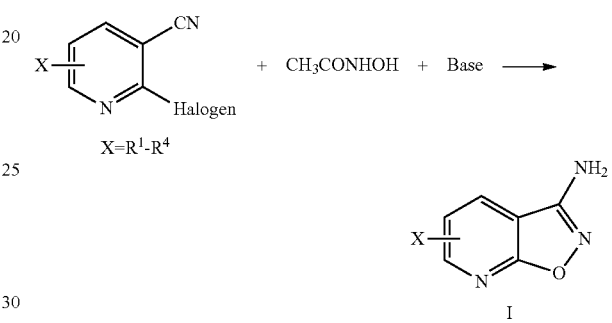

Compounds bearing alkylamino substituents and/or arylamino substituents may be prepared by displacement of an activated halogen atom with amines and/or anilines (Method 2).

Method 2

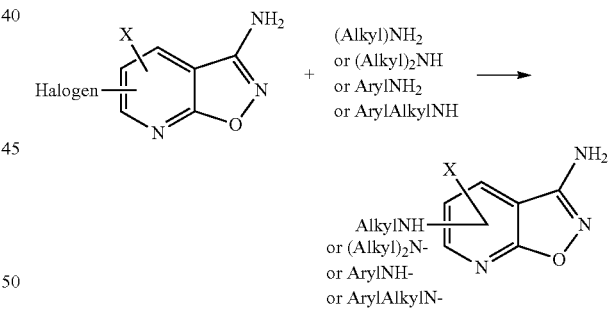

Compounds containing alkyl substitution on the exocyclic amino group may be prepared by reaction of the primary amine with a trialkylorthoformate, followed by reduction with an appropriate reducing agent, such as sodium borohydride (Method 3).

Method 3

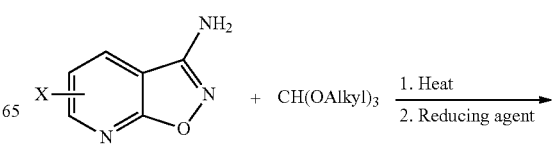

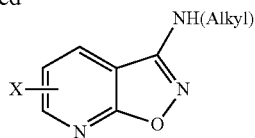

Such compounds may also be prepared by reaction of the primary amine with an alkyl aldehyde, followed by a reducing agent such as sodium cyanoborohydride, in a reductive amination process (Method 4).

Method 4

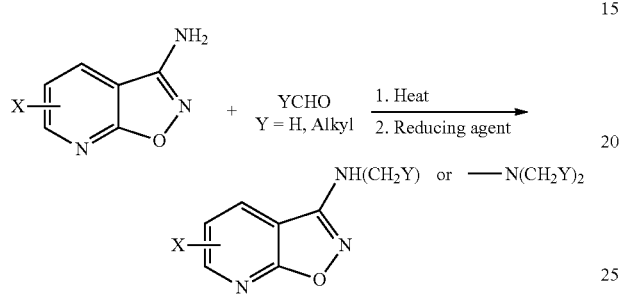

Compounds bearing a pendant aryl or heteroaryl (Het) substituent may be prepared by reaction of an appropriately substituted halogen- or triflate-containing substrate with suitable aryl or heteroaryl boronic acids or esters, under palladium catalysis, in a Suzuki coupling reaction (Method 5).

Method 5

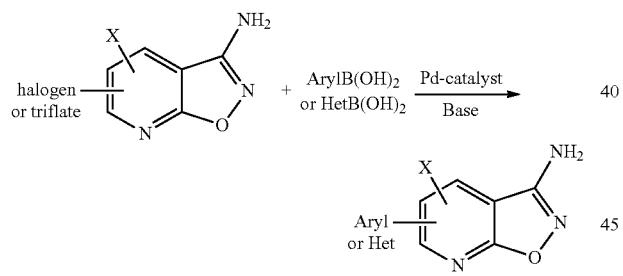

Compounds bearing a pendant aryl or heteroaryl (Het) substituent may also be prepared by performing a palladium-catalysed Suzuki coupling reaction with an appropriately substituted halogen or triflate-containing chemical intermediate, and suitable aryl or heteroaryl boronic acids or esters, followed by elaboration of the resultant aryl- or heteroarylated product to the final product (Method 6).

Method 6

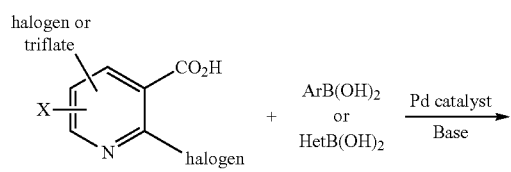

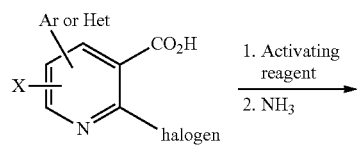

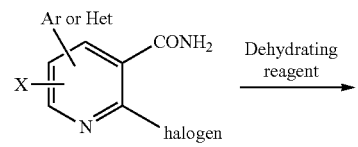

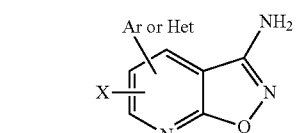

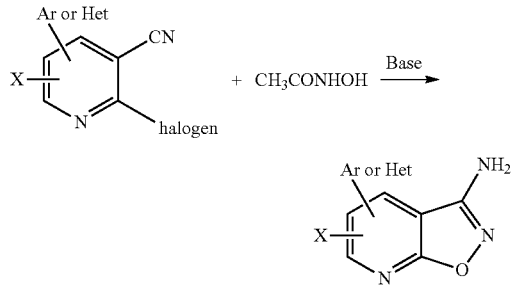

Compounds containing alkyl and/or aryl ether-linked substituents may be prepared by displacement of an activated halogen atom by alcohols and/or phenols, in the presence of a base such as sodium or sodium hydride or cesium carbonate (Method 7).

Method 7

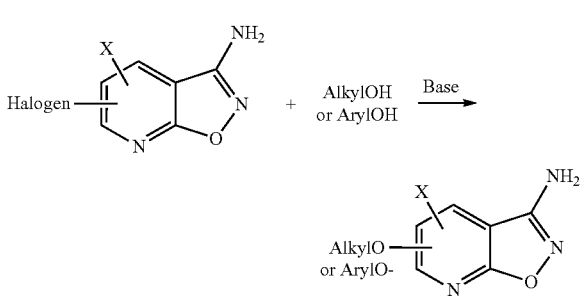

Compounds containing thioalkyl and/or thioaryl ether-linked substituents may be prepared by displacement of an activated halogen atom by thiols and/or thiophenols, in the presence of a base such as sodium or sodium hydride or cesium carbonate, or by direct reaction with the metal salt of a thiol or thiophenol. The resultant thioalkyl or thiophenol derivatives may be oxidised to their corresponding sulfoxide or sulfone derivatives with suitable oxidising reagents such as hydrogen peroxide, peracids, metal complexes and oxaziridines (Method 8).

Method 8

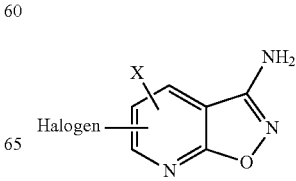

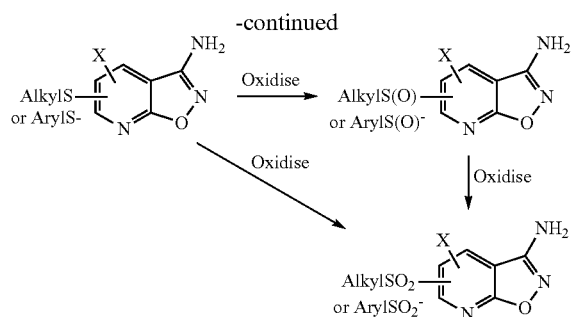

Those persons skilled in the art will understand that by using analogous procedures to those outlined above, other compounds of the Formula I can also be prepared.

Therapeutic Methods of the Invention

The compounds of Formula I of the invention may be inhibitors of IDO1 or TDO, or both IDO1 and TDO. Compounds that are inhibitors of either IDO1 or TDO, and compounds that are dual inhibitors of IDO1 and TDO, are expected to be useful in cancer therapy. Accordingly, in certain embodiments, the present invention provides methods of treating cancer in warm blooded animals, including humans, by administering to a subject in need of such treatment a therapeutically effective amount of a compound of Formula I, or a pharmaceutical composition containing a compound of Formula I.

In particular aspects of the invention, the compounds of formula I are expected to be useful in restoring tumor immunity in cancer patients. The compounds of the invention may be useful either alone, or in combination with other cancer therapies, including chemotherapeutic agents, radiation and/or immune modulating agents.

Immune modulating agents include, without limitation, anti-cancer vaccines, agents that modulate immune checkpoint proteins (such as CTLA4 and the PD1-4s) and adoptive T-cell therapies (such as CARTs). Accordingly, the compound of Formula I can be administered either alone or in combination with one or more other such therapies, either simultaneously or sequentially dependent upon the particular condition to be treated.

In particular embodiments, the compound of Formula I may be administered in combination with one or more immunotherapies selected from Ipilimumab (an inhibitor of CTLA4), Nivolumab and Lambrolizumab (both inhibitors of PD-1).

Additional chemotherapeutic agents that can be administered in combination with a compound of Formula I include but are not limited to compounds listed on the cancer chemotherapy drug regimens in the 14$^{th}$ Edition of the Merck Index (2006), which is hereby incorporated by reference, such as asparaginase, bleomycin, carboplatin, carmustine, chlorambucil, cisplatin, colaspase, cyclophosphamide, cytarabine, dacarbazine, dactinomycin, daunorubicin, doxorubicin (adriamycin), epirubicin, etoposide, 5-fluorouracil, hexamethylmelamine, hydroxyurea, ifosfamide, irinotecan, leucovorin, lomustine, mechlorethamine, 6-mercaptopurine, mesna, methotrexate, mitomycin C, mitoxantrone, prednisolone, prednisone, procarbazine, raloxifen, streptozocin, tamoxifen, thioguanine, topotecan, vinblastine, vincristine, and vindesine.

Additional anti-proliferative agents that can be administered in combination with a compound of Formula I include but are not limited to BCNU, CCNU, DTIC, and actinomycin D. Still further anti-proliferative agents include but are not limited to those compounds acknowledged to be used in the treatment of neoplastic diseases in *Goodman and Gilman's The Pharmacological Basis of Therapeutics* (Eleventh Edition), editor Molinoff et al., publ. by McGraw-Hill, pages 1225-1287 (2006), which is hereby incorporated by reference, such as aminoglutethimide, L-asparaginase, azathioprine, 5-azacytidine cladribine, busulfan, diethylstilbestrol, 2',2'-difluorodeoxycytidine, docetaxel, erythrohydroxynonyladenine, ethinyl estradiol, 5-fluorodeoxyuridine, 5-fluorodeoxyuridine monophosphate, fludarabine phosphate, fluoxymesterone, flutamide, hydroxyprogesterone caproate, idarubicin, interferon, medroxyprogesterone acetate, megestrol acetate, melphalan, mitotane, paclitaxel, pentostatin, N-phosphonoacetyl-L-aspartate (PALA), plicamycin, semustine, tenipdside, testosterone propionate, thiotepa, trimethylmelamine, uridine, and vinorelbine.

Additional anti-proliferative agents that can be administered in combination with a compound of Formula I include but are not limited to other molecular targeted agents, which block the growth of cancer cells by interfering with specific targeted molecules needed for carcinogenesis and tumour growth. Examples include small molecule protein and lipid kinase inhibitors, monoclonal antibodies, molecularly targeted humanised monoclonal antibodies and monoclonal antibody drug conjugates. Examples of such inhibitors include: Rituximab, Trastuzumab, Alemtuzumab, Tositumomab-I131, Cetuximab, Ibritumomab tiuxetan, Bevacizumab, Panitumumab, Ofatumumab, Ipilimumab, Brentuximab vedotin, Pertuzumab, Ado-Trastuzumab emtansine, Ramucirumab, Obinutuzumab, Nivolumab, Lambrolizumab, Dinutuximab, Imatinib, Gefitinib, Erlotinib, Sorafenib, Dasatinib, Sunitinib, Lapatinib, Nilotinib, Pazopanib, Crizotinib, Ruxolitinib, Vandetanib, Vemurafenib, Axitinib, Bosutinib, Cabozantinib, Ponatinib, Regorafenib, Tofacitinib, Afatinib, Dabrafenib, Ibrutinib and Trametinib.

A wide range of cancers may be treated by the compounds of the present invention. Cancers that may be treated in accordance with the present invention include but are not limited to: colorectal cancer, cancers of the breast, melanoma, reproductive organs, respiratory tract, brain, digestive tract, urinary tract, eye, liver, skin, head and neck, thyroid, parathyroid and their distant metastases. Those disorders also include lymphomas, sarcomas, and leukemias.

Examples of breast cancer include, but are not limited to invasive ductal carcinoma, invasive lobular carcinoma, ductal carcinoma in situ, and lobular carcinoma in situ.

Examples of cancers of the respiratory tract include, but are not limited to small-cell and non-small-cell lung carcinoma, as well as bronchial adenoma and pleuropulmonary blastoma.

Examples of brain cancers include, but are not limited to brain stem and hypophthalmic glioma, cerebellar and cerebral astrocytoma, medulloblastoma, ependymoma, as well as neuroectodermal and pineal tumor.

Tumors of the male reproductive organs include, but are not limited to prostate and testicular cancer.

Tumors of the female reproductive organs include, but are not limited to endometrial, cervical, ovarian, vaginal, and vulvar cancer, as well as sarcoma of the uterus.

Tumors of the digestive tract include, but are not limited to anal, colon, colorectal, esophageal, gallblader, gastric, pancreatic, rectal, small-intestine, and salivary gland cancers.

Tumors of the urinary tract include, but are not limited to bladder, penile, kidney, renal pelvis, ureter, and urethral cancers.

Eye cancers include, but are not limited to intraocular melanoma and retinoblastoma.

Examples of liver cancers include, but are not limited to hepatocellular carcinoma (liver cell carcinomas with or without fibrolamellar variant), cholangiocarcinoma (intrahepatic bile duct carcinoma), and mixed hepatocellular cholangiocarcinoma.

Skin cancers include, but are not limited to squamous cell carcinoma, Kaposi's sarcoma, malignant melanoma, Merkel cell skin cancer, and non-melanoma skin cancer.

Head-and-neck cancers include, but are not limited to laryngeal/hypopharyngeal/nasopharyngeal/oropharyngeal cancer, and lip and oral cavity cancer. Lymphomas include, but are not limited to AIDS-related lymphoma, non-Hodgkin's lymphoma, cutaneous T-cell lymphoma, Hodgkin's disease, and lymphoma of the central nervous system.

Sarcomas include, but are not limited to sarcoma of the soft tissue, osteosarcoma, malignant fibrous histiocytoma, lymphosarcoma, and rhabdomyosarcoma. Leukemias include, but are not limited to acute myeloid leukemia, acute lymphoblastic leukemia, chronic lymphocytic leukemia, chronic myelogenous leukemia, and hairy cell leukemia.

These disorders have been well characterized in man, but also exist with a similar etiology in other warm-blooded animals, and can be treated by the compounds of the present invention.

It will be appreciated by those skilled in the art that a particular method of therapy will employ a selected route of administration which will in turn depend on a variety of factors, all of which are considered routinely when administering therapeutics. It will be further appreciated by one skilled in the art that the optimal course of treatment, i.e., the mode of treatment and the daily number of doses of a compound of this invention given for a defined number of days, can be ascertained by those skilled in the art using conventional treatment tests.

Therapeutic dosages will likely be in the range of 1 mg to 30 g per day. The specific dose level selected for any particular patient will depend upon a variety of factors, including the activity of the specific compound employed, the age, body weight, general health, sex, diet, time of administration, route of administration, and rate of excretion, drug combination and the severity of the condition undergoing therapy.

Certain compounds of Formula I, as well as being inhibitors of IDO1, may also inhibit IDO2. Compounds that are dual inhibitors of IDO1 and IDO2 are also expected to be useful in cancer therapy. Accordingly, in another aspect, the invention provides a method of inhibiting IDO1 and IDO2 in a warm blooded animal in need thereof, including a human, comprising administering to the animal a compound of Formula I or a pharmaceutically acceptable salt thereof, in an amount effective to inhibit IDO1 and IDO2.

It has been reported that compounds that are inhibitors of IDO (IDO1 and IDO2) and/or TDO may have efficacy not only in the treatment of cancer, but also in the treatment of a range of other diseases or conditions, for example as discussed in PCT International Publication WO 2015/082499 and the references to scientific literature referred to therein, all of which are incorporated herein by reference. For example, such compounds may be useful in the treatment of inflammatory conditions, infectious diseases, central nervous system diseases or disorders, coronary heart disease, chronic renal failure, post anaesthesia cognitive dysfunction, disease conditions or disorders relating to female reproductive health, and cataracts. Accordingly, compounds of Formula I of the present invention may also be useful in the treatment of such diseases or conditions.

Examples of inflammatory conditions that may be treated by compounds of Formula I include conditions relating to immune B cell, T cell, dendritic cell, natural killer cell, macrophage, and/or neutrophil dysregulation.

Examples of infectious diseases that may be treated by compounds of Formula I include bacterial infections, viral infections such as gut infections, hepatitis C, sepsis, and sepsis induced hypotension.

Examples of central nervous system diseases or disorders that may be treated by compounds of Formula I include amyotrophic lateral sclerosis (AML), Huntington's disease, Alzheimer's disease, pain, psychiatric disorders including affective disorders such as depression, multiple sclerosis, Parkinson's disease, and HIV related neurocognitive decline.

An example of diseases or disorders relating to female reproductive health that may be treated by compounds of Formula I is endometriosis, and conditions relating to female reproductive health include contraception and abortion.

Pharmaceutical Compositions of the Invention

The invention includes pharmaceutical compositions including one or more compounds of Formula I of this invention, and a pharmaceutically acceptable carrier.

The pharmaceutically acceptable excipient, adjuvant, carrier, buffer or stabiliser should be nontoxic and should not interfere with the efficacy of the active ingredient. The precise nature of the carrier or other material will depend on the route of administration.

The compounds may be administered orally, topically, parenterally, by inhalation or spray or rectally in dosage unit formulations. The term 'administration by injection' includes intravenous, intramuscular, subcutaneous and parenteral injections, as well as use of infusion techniques. One or more compounds may be present in association with one or more non-toxic pharmaceutically acceptable carriers and if desired other active ingredients.

Compositions intended for oral use may be prepared according to any suitable method known to the art for the manufacture of pharmaceutical compositions. Such compositions may contain one or more agents selected from the group consisting of diluents, sweetening agents, flavoring agents, coloring agents and preserving agents in order to provide palatable preparations. Tablets contain the active ingredient in admixture with non-toxic pharmaceutically acceptable excipients which are suitable for the manufacture of tablets. These excipients may be, for example, inert diluents, such as calcium carbonate, sodium carbonate, lactose, calcium phosphate or sodium phosphate; granulating and disintegrating agents, for example, corn starch, or alginic acid; and binding agents, for example magnesium stearate, stearic acid or talc. The tablets may be uncoated or they may be coated by known techniques to delay disintegration and adsorption in the gastrointestinal tract and thereby provide a sustained action over a longer period. For example, a time delay material such as glyceryl monostearate or glyceryl distearate may be employed. These compounds may also be prepared in solid, rapidly released form.

Formulations for oral use may also be presented as hard gelatin capsules wherein the active ingredient is mixed with an inert solid diluent, for example, calcium carbonate, calcium phosphate or kaolin, or as soft gelatin capsules wherein the active ingredient is mixed with water or an oil medium, for example peanut oil, liquid paraffin or olive oil.

Aqueous suspensions contain the active materials in admixture with excipients suitable for the manufacture of aqueous suspensions. Such excipients are suspending agents, for example sodium carboxymethylcellulose, methylcellulose, hydroxypropyl methylcellulose, sodium alginate, polyvinylpyrrolidone, gum tragacanth and gum acacia; dispersing or wetting agents may be a naturally occurring phosphatide, for example, lecithin, or condensation products or an alkylene oxide with fatty acids, for example polyoxyethylene stearate, or condensation products of ethylene oxide with long chain aliphatic alcohols, for example heptadecaethylene oxycetanol, or condensation products of ethylene oxide with partial esters derived from fatty acids and hexitol such as polyoxyethylene sorbitol monooleate, or condensation products of ethylene oxide with partial esters derived from fatty acids and hexitol anhydrides, for example polyethylene sorbitan monooleate. The aqueous suspensions may also contain one or more preservatives, for example ethyl, or n-propyl p-hydroxybenzoate, one or more coloring agents, one or more flavoring agents, and one or more sweetening agents, such as sucrose or saccharin.

Dispersible powders and granules suitable for preparation of an aqueous suspension by the addition of water provide the active ingredient in admixture with a dispersing or wetting agent, suspending agent and one or more preservatives. Suitable dispersing or wetting agents and suspending agents are exemplified by those already mentioned above. Additional excipients, for example, sweetening, flavoring and coloring agents, may also be present.

The compounds may also be in the form of non-aqueous liquid formulations, e.g., oily suspensions which may be formulated by suspending the active ingredients in a vegetable oil, for example arachis oil, olive oil, sesame oil or peanut oil, or in a mineral oil such as liquid paraffin. The oily suspensions may contain a thickening agent, for example beeswax, hard paraffin or cetyl alcohol. Sweetening agents such as those set forth above, and flavoring agents may be added to provide palatable oral preparations. These compositions may be preserved by the addition of an anti-oxidant such as ascorbic acid.

Pharmaceutical compositions of the invention may also be in the form of oil-in-water emulsions. The oily phase may be a vegetable oil, for example olive oil or arachis oil, or a mineral oil, for example liquid paraffin or mixtures of these. Suitable emulsifying agents may be naturally-occurring gums, for example gum acacia or gum tragacanth, naturally-occurring phosphatides, for example soy bean, lecithin, and esters or partial esters derived from fatty acids and hexitol anhydrides, for example sorbitan monooleate, and condensation products of the said partial esters with ethylene oxide, for example polyoxyethylene sorbitan monooleate. The emulsions may also contain sweetening and flavoring agents.

Syrups and elixirs may be formulated with sweetening agents, for example glycerol, propylene glycol, sorbitol or sucrose. Such formulations may also contain a demulcent, a preservative, and flavoring and coloring agents.

The compounds may also be administered in the form of suppositories for rectal administration of the drug. These compositions can be prepared by mixing the drug with a suitable non-irritating excipient which is solid at ordinary temperatures but liquid at the rectal temperature and will therefore melt in the rectum to release the drug. Such materials include cocoa butter and polyethylene glycols.

EXAMPLES

The following examples are representative of the compounds of the invention and methods for preparing them. However, the scope of the invention is not to be taken as being limited to these examples.

Synthetic Procedures

Starting materials not described explicitly were either available commercially or their synthesis has been described in the chemistry literature or the materials can be prepared by methods known to a person skilled in the art. Exemplar compounds were characterised by $^1$H NMR spectroscopy, APCI ionisation mass spectrometry, melting point, and combustion or HRMS analysis. Purity of the exemplar compounds was determined by HPLC analysis and found to be >95% for all compounds.

Silica gel 60 ($SiO_2$) (0.040-0.063 mm) was used for all column chromatography.

ABBREVIATIONS

NMR nuclear magnetic resonance
ESI electrospray ionisation
APCI atmospheric pressure chemical ionisation
HPLC high performance liquid chromatography
LCMS liquid chromatography-mass spectrometry
HRMS high resolution mass spectrometry
mp melting point
DMF dimethylformamide
EtOAc ethyl acetate
DCM dichloromethane
MeOH methanol
THF tetrahydrofuran
HOAc acetic acid
dppf 2-(diphenylphosphino)ferrocene
EDCI 1-Ethyl-(3-dimethylaminopropyl)carbodiimide hydrochloride
TEA Triethylamine Method 1. Representative Example 5-Bromo-4,6-dimethylisoxazolo[5,4-b]pyridin-3-amine (1)

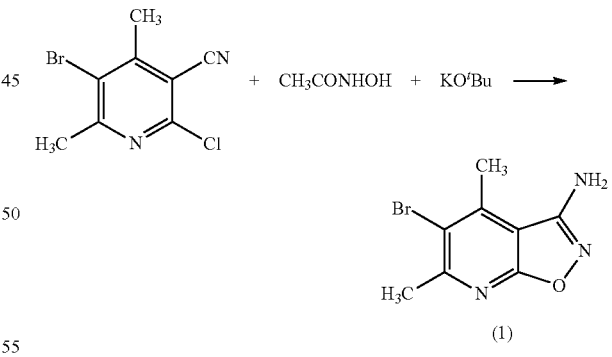

To a solution of acetohydroxamic acid (0.61 g, 8.13 mmol) in dry DMF (10 mL) under nitrogen was added potassium tert-butoxide (0.91 g, 8.14 mmol). The reaction mixture was stirred at 20° C. for 2 hr. 5-Bromo-2-chloro-4,6-dimethylnicotinonitrile (1.00 g, 4.07 mmol) was then added and the resulting mixture was stirred at 20° C. for 24 hr, then diluted with $H_2O$ (150 ml) and stirred for 1 hr. The resulting white precipitate was filtered and washed with water. The filtrate was extracted with EtOAc (30 mL×3). Combined organic fractions were dried ($Na_2SO_4$), and the solvent evaporated under vacuum to give further material.

Both the isolated solid and the extracted material were combined and chromatographed on SiO$_2$ eluting with a 0-50% gradient of petroleum ether/EtOAc. The column purified product was recrystallized from DCM/petroleum ether to give 5-bromo-4,6-dimethylisoxazolo[5,4-b]pyridin-3-amine (1) (0.68 g, 69%) as a white solid, mp (DCM/petroleum ether) 208-211° C., $^1$H NMR [(CD$_3$)$_2$SO] δ 6.24 (s, 2H, NH$_2$), 2.66 (6H, 2×CH$_3$), LCMS [M+H]=242 and 244. Calc. for C$_8$H$_8$BrN$_3$O: C, 36.7; H, 3.3; N, 17.4; found C, 36.9; H, 3.2, N, 17.4%.

Similarly were prepared:

Isoxazolo[5,4-b]pyridin-3-amine (2)

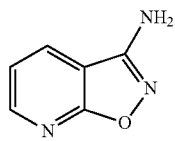

(2)

From 2-chloronicotinonitrile in 1,2-dimethoxyethane in 48% yield;

5-Chloro-4,6-dimethylisoxazolo[5,4-b]pyridin-3-amine (3)

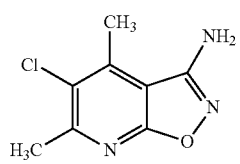

(3)

From 2,5-dichloro-4,6-dimethylnicotinonitrile in 75% yield; mp (DCM/petroleum ether) 214-216° C. $^1$H NMR [(CD$_3$)$_2$SO] δ 6.25 (bs, 2H, NH$_2$), 2.64 (s, 3H, CH$_3$), 2.61 (s, 3H, CH$_3$); LCMS [M+H]=198; HPLC 99.8%; Anal calcd. for C$_8$H$_8$ClN$_3$O: C, 48.6; H, 4.1; N, 21.4; found C, 48.8; H, 3.9, N, 21.4%.

4,6-Dimethylisoxazolo[5,4-b]pyridin-3-amine (4)

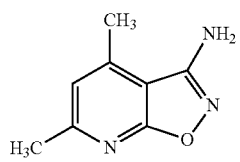

(4)

From 2-chloro-4,6-dimethylnicotinonitrile in 40% yield; mp (DCM/petroleum ether) 156-158° C.; $^1$H NMR [(CD$_3$)$_2$SO] δ 6.98 (s, 1H), 6.09 (bs, 2H, NH$_2$), 2.57 (d, J=0.6 Hz, 3H, CH$_3$), 2.48 (s, 3H, CH$_3$); HPLC 99.9%; Anal. calcd. for C$_8$H$_9$N$_3$O: C, 58.9; H, 5.6; N, 25.5; found C, 59.0; H, 5.6; N, 25.9%.

4,5,6-Trimethylisoxazolo[5,4-b]pyridin-3-amine (5)

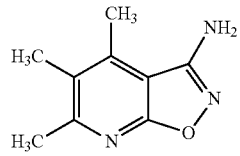

(5)

From 2-chloro-4,5,6-trimethylnicotinonitrile in 39% yield; mp (DCM/petroleum ether) 204-207° C.; $^1$H NMR [(CD$_3$)$_2$SO] δ 6.04 (bs, 2H, NH$_2$), 2.44 (s, 6H, 2×CH$_3$), 2.14 (s, 3H, CH$_3$); HPLC 99.9%; Anal. calcd. for C$_9$H$_{11}$N$_3$O: C, 61.0; H, 6.3; N, 23.7; found C, 61.0; H, 6.3; N, 23.7%.

5-Bromoisoxazolo[5,4-b]pyridin-3-amine (6)

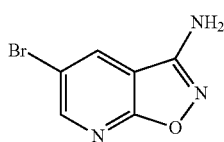

(6)

From 5-bromo-2-chloronicotinonitrile in 60% yield; mp (DCM/petroleum ether) 231-234° C.; $^1$H NMR [(CD$_3$)$_2$SO] δ 8.63 ((d, J=2.3 Hz, 1H), 8.55 (d, J=2.3 Hz, 1H), 6.71 (bs, 2H, NH$_2$); HPLC 99.6%; LCMS [M+H] 214 and 216; Anal. calcd. for C$_6$H$_4$BrN$_3$O: C, 33.7; H, 1.9; N, 19.6; found C, 33.9; H, 1.7; N, 19.5%.

6-Methylisoxazolo[5,4-b]pyridin-3-amine (7)

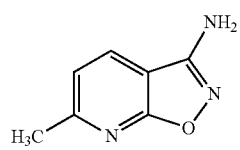

(7)

From 2-chloro-6-methylnicotinonitrile in 40% yield; mp (DCM/petroleum ether) 224-226° C.; HPLC 100%; LCMS [M+H]=150; Anal. calcd. for C$_7$H$_7$N$_3$O: C, 56.4; H, 4.7; N, 28.2; found C; 56.6; H, 4.5; N, 28.2%.

5-Chloroisoxazolo[5,4-b]pyridin-3-amine (8)

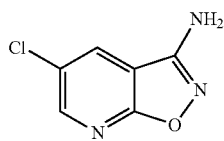

(8)

From 2,5-dichloronicotinonitrile in 79% yield; mp (DCM/petroleum ether) 257-260° C.; $^1$H NMR [(CD$_3$)$_2$SO] δ 8.57 (d, J=2.4 Hz, 1H), 8.42 (d, J=2.5 Hz, 1H), 6.72 (s, 2H, NH$_2$), HPLC 99.9%; LCMS [M+H]=170; Anal. calcd. for C$_6$H$_4$ClN$_3$O; C, 42.5; H, 2.4; N, 24.8; found C, 42.6; H, 2.2; N, 24.6%.

Isoxazolo[5,4-b]quinolin-3-amine (9)

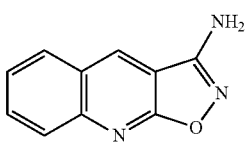
(9)

From 2-chloroquinoline-3-carbonitrile in 72% yield; mp (DCM/petroleum ether) 261-263° C.; $^1$H NMR [(CD$_3$)$_2$SO] δ 8.93 (s, 1H), 8.16 (dd, J=8.3, 1.0 Hz, 1H), 7.99 (d, J=8.6 Hz, 1H), 7.87 (ddd, J=8.5, 6.8, 1.4 Hz, 1H), 7.59 (ddd, J=8.1, 6.8, 1.1 Hz, 1H), 6.89 (s, 2H, NH$_2$). HPLC 99.6%; Anal. calcd. for C$_{10}$H$_7$N$_3$O; C, 64.9; H, 3.8; N, 22.7; C, 65.0; H, 3.7; N, 22.7%.

5,6,7,8-Tetrahydroisoxazolo[5,4-b]quinolin-3-amine (10)

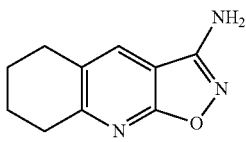
(10)

From 2-chloro-5,6,7,8-tetrahydroquinoline-3-carbonitrile in 61% yield; mp (DCM/MeOH) 236-239° C.; $^1$H NMR [(CD$_3$)$_2$SO] δ 7.92 (s, 1H), 6.46 (bs, 2H, NH$_2$), 2.88 (t, J=6.4 Hz, 2H), 2.83 (t, J=6.2 Hz, 2H), 1.87-1.74 (m, 4H); HPLC 100%; LCMS [M+H]=190; Anal. calcd. for C$_{10}$H$_{11}$N$_3$O: C, 63.5; H, 5.9; N, 22.2; found C, 63.6; H, 5.9, N, 22.2%.

6-Chloroisoxazolo[5,4-b]pyridin-3-amine (11)

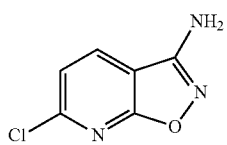
(11)

From 2,6-dichloronicotinonitrile in 2% yield; mp (DCM/MeOH) 238-241° C.; $^1$H NMR [(CD$_3$)$_2$SO] δ 8.33 (d, J=8.1 Hz, 1H), 7.48 (d, J=8.1 Hz, 1H), 6.76 (bs, 2H, NH$_2$); LCMS [M+H]=170; HPLC 99.9%, Anal. calcd. for C$_6$H$_4$ClNO$_3$: C, 42.5; H, 2.4; N, 24.8; found C, 42.7; H, 2.3; N, 24.7%.

Isoxazolo[5,4-d]pyrimidin-3-amine (12)

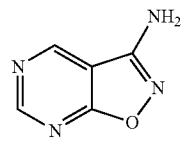
(12)

From 4-chloropyrimidine-5-carbonitrile in 1,4-dioxane in 15% yield; mp (DCM/petroleum ether)>295° C.; $^1$H NMR [(CD$_3$)$_2$SO] δ 9.29 (s, 1H), 9.08 (s, 1H), 7.00 (bs, 2H, NH$_2$); LCMS [M+H]=137; HPLC 96.0%; Anal. calcd. for C$_5$H$_4$N$_4$O; C, 44.1; H, 3.0; N, 41.2; found C, 44.3; H, 2.9; N, 40.9%.

4-Phenylisoxazolo[5,4-b]pyridin-3-amine (13)

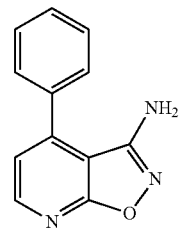
(13)

From 2-chloro-4-phenylnicotinonitrile in 1,2-dimethoxyethane in 26.6% yield; mp (DCM/petroleum ether) 196-199° C.; LCMS [M+H]=212; HPLC 99.7%; Anal. calcd. for C$_{12}$H$_9$N$_3$O: C, 68.2; H, 4.3; N, 19.9; found C, 68.4; H, 4.2; N, 20.0%.

5-Fluoroisoxazolo[5,4-b]pyridin-3-amine (14)

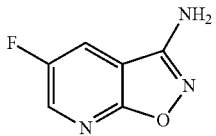
(14)

From 2-chloro-5-fluoronicotinonitrile in 1,2-dimethoxyethane in 45% yield; mp (DCM/petroleum ether) 223-226° C.; LCMS [M+H]=154; HPLC 99.8%; Anal. calcd. for C$_6$H$_4$FN$_3$O: C, 47.1; H, 2.6; N, 27.4 found C, 47.3; H, 2.5 N, 27.7%.

6-Phenylisoxazolo[5,4-b]pyridin-3-amine (15)

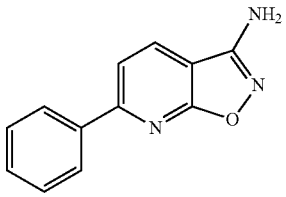
(15)

From 2-chloro-6-phenylnicotinonitrile in 48% yield; mp (DCM/petroleum ether) 236-238° C.; LCMS [M+H]=212; $^1$H NMR [(CD$_3$)$_2$SO] δ 8.36 (d, J=8.1 Hz, 1H), 8.17-8.14 (m, 2H), 7.97 (d, J=8.27 Hz, 1H); 7.56-7.48 9 (m, 3H), 6.65 (s, 2H, NH$_2$); HPLC 100%; Anal. calcd. for C$_{12}$H$_9$N$_3$O: C, 68.2; H, 4.3; N, 19.9; found C, 68.3; H, 4.2; N, 19.8%.

5-Iodoisoxazolo[5,4-b]pyridin-3-amine (16)

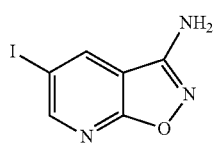
(16)

From 2-chloro-5-iodonicotinonitrile in 35% yield; mp (DCM/MeOH) 243-246° C.; LCMS [M+H]=262; 1H NMR [(CD$_3$)$_2$SO] δ 8.69 (2×d, J=2.1 Hz, 2H), 6.68 (bs, 2H, NH$_2$); HPLC 99.9%; Anal. calcd. for C$_6$H$_4$IN$_3$O: C, 27.6; H, 1.5; N; 16.1; found C, 27.7; H, 1.6; N, 160.0%.

Isoxazolo[4,5-c]pyridin-3-amine (17)

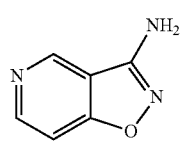
(17)

From 4-chloronicotinonitrile in 11% yield; mp (DCM/MeOH) 189-192° C.; LCMS [M+H]=136; HPLC 99.7%. HRMS (ESI$^+$) calcd. for C$_6$H$_6$N$_3$O 136.0505; found 136.0502.

6-Chloro-4-methylisoxazolo[5,4-b]pyridin-3-amine (42)

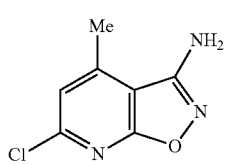
(42)

From 2,6-dichloro-4-methylnicotinonitrile, mp 225-228° C.; $^1$H NMR [(CD$_3$)$_2$SO] δ 7.28 (s, 1H), 6.33 (br s, 2H, NH$_2$), 2.63 (s, 3H, CH$_3$); HPLC 99.3%; LCMS found: [M+H]=184, 186.

Isoxazolo[5,4-b]pyridine-3,6-diamine (43)

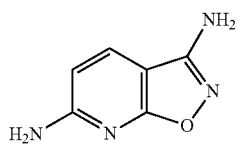
(43)

From 6-amino-2-chloronicotinonitrile, mp 205-208° C.; $^1$H NMR [(CD$_3$)$_2$SO] δ 7.71 (d, J=8.8 Hz, 1H), 6.70 (br s, 2H, NH$_2$), 6.31 (d, J=8.8 Hz, 1H), 6.08 (br s, 2H, NH$_2$); HPLC 99.0%; LCMS found: [M+H]=151.

5-Methylisoxazolo[5,4-b]pyridin-3-amine (44)

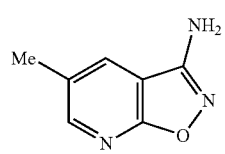
(44)

From 5-methyl-2-chloronicotinate, mp 232-234° C.; $^1$H NMR [(CD$_3$)$_2$SO] δ 8.35 (d, J=1.2 Hz, 1H), 8.07 (d, J=1.2 Hz, 1H), 6.57 (br s, 2H, NH$_2$), 2.39 (s, 3H, CH$_3$); HPLC 96.4%. LCMS found: [M+H]=150.

5,6-Dimethylisoxazolo[5,4-b]pyridin-3-amine (45)

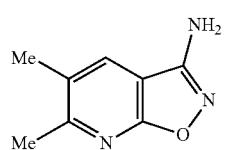
(45)

From 2-chloro-5,6-dimethylnicotinonitrile, mp 263-266° C.; $^1$H NMR [(CD$_3$)$_2$SO] δ 7.95 (s, 1H), 6.47 (br s, 2H, NH$_2$), 2.49 (s, 3H, CH$_3$), 2.31 (s, 3H, CH$_3$); HPLC 99.1%; LCMS found: [M+H]=164.

6-Methyl-4-(trifluoromethyl)isoxazolo[5,4-b]pyridin-3-amine (46)

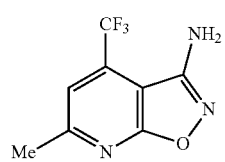
(46)

From 2-chloro-6-methyl-4-(trifluoromethyl)nicotinonitrile, mp 112-114° C.; ¹H NMR [(CD₃)₂SO] δ 7.70 (s, 1H), 6.07 (br s, 2H, NH₂), 2.68 (s, 3H, CH₃); HPLC 97.7%. LCMS found: [M+H]=218.

6-(Trifluoromethyl)isoxazolo[5,4-b]pyridin-3-amine (47)

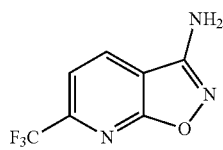

(47)

From 2-chloro-6-(trifluoromethyl)nicotinonitrile in 31% yield, mp (DCM/MeOH) 226-228° C.; ¹H NMR [(CD₃)₂SO] δ 8.60 (d, J=7.90 Hz, 1H), 7.90 (d, J=7.90 Hz, 1H), 6.93 (brs 2H); Anal. calcd. for $C_7H_4F_3N_3O$: C, 41.4, H, 2.0; N, 20.7; found C, 41.4, H, 1.8; N, 20.5%.

6-Isopropylisoxazolo[5,4-b]pyridin-3-amine (48)

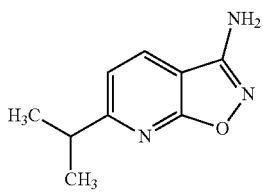

(48)

From 2-chloro-6-isopropylnicotinonitrile in 79% yield, mp (DCM/pet. ether) 165-168°; ¹H NMR [(CD₃)₂SO] δ 8.18 (d, J=8.0 Hz, 1H), 7.26 (d, J=8.0 Hz, 1H), 6.53 (brs, 2H), 3.11 (sp, J=6.9 Hz, 1H), 1.25 (d, J=6.9 Hz, 6H); Anal. calcd. for $C_9H_{11}N_3O$: C, 61.0; H, 6.3 N, 23.7; found C, 61.2; H, 6.4; N, 23.5%.

5-Nitroisoxazolo[5,4-b]pyridin-3-amine (49)

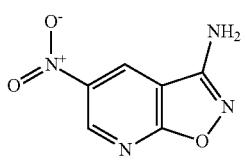

(49)

From 5-nitro-2-chloronicotinonitrile, mp>290° C.; ¹H NMR [(CD₃)₂SO] δ 9.37 (d, J=2.8 Hz, 1H), 9.27 (d, J=2.8 Hz, 1H), 7.06 (br s, 2H, NH₂); HPLC 99.8%. LCMS found: [M+H]=181.

Ethyl 3-amino-6-(trifluoromethyl)isoxazolo[5,4-b]pyridine-5-carboxylate (50)

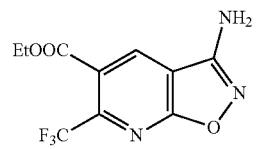

(50)

From ethyl 6-chloro-5-cyano-2-(trifluoromethyl)nicotinate, mp 177-180° C.; ¹H NMR [(CD₃)₂SO] δ 8.95 (s, 1H), 7.08 (br s, 2H, NH₂), 4.40 (q, J=8.0 Hz, 2H, OCH₂). 1.34 (t, J=8.0 Hz, 3H, CH₃); HPLC 99.1%. LCMS found: [M+H]=276.

4-Methoxyisoxazolo[5,4-b]pyridin-3-amine (51)

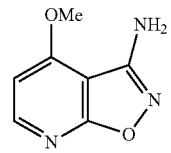

(51)

From 2-chloro-4-methoxynicotinonitrile, mp 241-243° C.; ¹H NMR [(CD₃)₂SO] δ 8.35 (d, J=5.9 Hz, 1H), 6.91 (d, J=5.9 Hz, 1H), 6.17 (br s, 2H, NH₂), 3.99 (s, 3H); HPLC 97.6%. LCMS found: [M+H]=166.

5-(Difluoromethoxy)-4,6-dimethylisoxazolo[5,4-b]pyridin-3-amine (52)

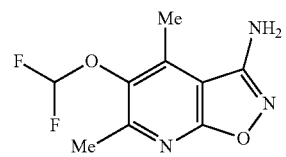

(52)

From 2-chloro-5-(difluoromethoxy)-4,6-dimethylnicotinonitrile, mp 151-153° C.; ¹H NMR [(CD₃)₂SO] δ 7.05 (t, J=74 Hz, 1H), 6.23 (br s, 2H, NH₂), 2.54 (s, 3H), 2.51 (s, 3H); HPLC 99.7%. LCMS found: [M+H]=230.

Ethyl 3-amino-6-methylisoxazolo[5,4-b]pyridine-5-carboxylate (53)

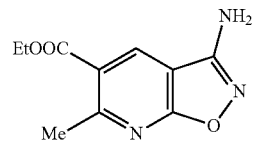

(53)

From ethyl 6-chloro-5-cyano-2-methylnicotinate, mp 178-180° C.; ¹H NMR [(CD₃)₂SO] δ 8.86 (s, 1H), 6.81 (br s, 2H, NH$_2$), 4.35 (q, J=7.2 Hz, 2H, OCH$_2$), 2.80 (s, 3H, CH$_3$), 1.36 (t, J=7.2 Hz, 3H, CH$_3$); HPLC 99.6%. LCMS found: [M+H]=222.

Ethyl 3-amino-6-(difluoromethyl)isoxazolo[5,4-b]pyridine-5-carboxylate (54)

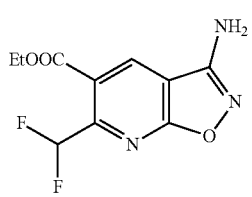

(54)

From ethyl 6-chloro-5-cyano-2-(difluoromethyl)nicotinate, mp 158-160° C.; $^1$H NMR [(CD$_3$)$_2$SO] δ 9.05 (s, 1H), 7.59 (t, J=53 Hz, 1H), 7.04 (br s, 2H, NH$_2$), 4.39 (q, J=6.8 Hz, 2H, OCH$_2$), 1.37 (t, J=6.8 Hz, 3H, CH$_3$); HPLC 99.1%. LCMS found: [M+H]=258.

5-Fluoro-6-morpholinoisoxazolo[5,4-b]pyridin-3-amine (55)

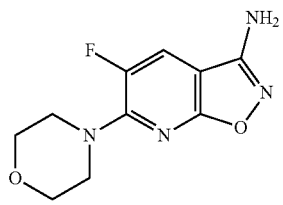

(55)

From 2-chloro-5-fluoro-6-morpholinonicotinonitrile, mp 168-170° C.; $^1$H NMR [(CD$_3$)$_2$SO] δ 7.86 (d, J=12.8 Hz, 1H), 6.33 (br s, 2H, NH$_2$), 3.72 (br s, 4H, CH$_2$O), 3.51 (br s, 4H, CH$_2$N); HPLC 98.0%. LCMS found: [M+H]=239.

N6-Cyclopropyl-5-fluoroisoxazolo[5,4-b]pyridine-3,6-diamine (56)

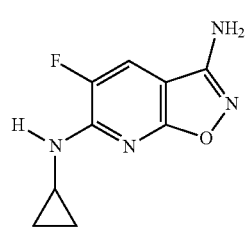

(56)

From 2-chloro-6-(cyclopropylamino)-5-fluoronicotinonitrile, mp 182-184° C.; $^1$H NMR [(CD$_3$)$_2$SO] δ 7.66 (d, J=12.9 Hz, 1H), 7.63 (br s, 1H, NH), 6.14 (br, 2H, NH$_2$), 2.75 (m, 1H, CHN), 0.73 (m, 2H, CH$_2$), 0.56 (m, 2H, CH$_2$); HPLC 99.4%. LCMS found: [M+H]=209.

5-Fluoro-N6,N6-dimethylisoxazolo[5,4-b]pyridine-3,6-diamine (57)

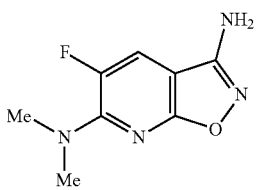

(57)

From 2-chloro-6-(dimethylamino)-5-fluoronicotinonitrile, mp 186-189° C.; $^1$H NMR [(CD$_3$)$_2$SO] δ 7.74 (d, J=13.2 Hz, 1H), 5.76 (br, 2H, NH$_2$), 3.11 (s, 6H, NMe$_2$); HPLC 96.2%. LCMS found: [M+H]=197.

6-(Furan-2-yl)isoxazolo[5,4-b]pyridin-3-amine (58)

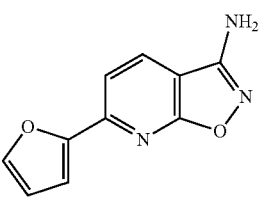

(58)

From 2-chloro-6-(furan-2-yl)nicotinonitrile, mp 269-272° C.; $^1$H NMR [(CD$_3$)$_2$SO] δ 8.31 (d, J=8.4 Hz, 1H), 7.93 (d, J=1.2 Hz, 1H), 7.72 (d, J=8.4 Hz, 1H), 7.28 (d, J=3.2 Hz, 1H), 6.72 (dd, J=3.2, 1.2 Hz, 1H), 6.64 (br s, 2H, NH$_2$). HPLC 98.7%. LCMS found: [M+H]=202.

6,7-Dihydro-5H-cyclopenta[b]isoxazolo[4,5-e]pyridin-3-amine (59)

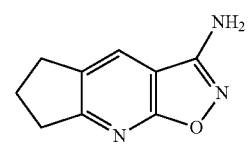

(59)

From 2-chloro-6,7-dihydro-5H-cyclopenta[b]pyridine-3-carbonitrile, mp 217-220° C.; $^1$H NMR [(CD$_3$)$_2$SO] δ 7.99 (s, 1H), 6.47 (br s, 2H, NH$_2$), 2.94 (m, 4H), 2.13 (m, 2H); HPLC 99.4%. LCMS found: [M+H]=176.

6,7,8,9-Tetrahydro-5H-cyclohepta[b]isoxazolo[4,5-e]pyridin-3-amine (60)

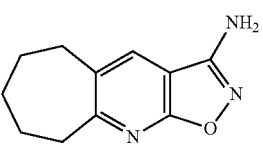

(60)

From 2-chloro-6,7,8,9-tetrahydro-5H-cyclohepta[b]pyridine-3-carbonitrile, mp 210-212° C.; ¹H NMR [(CD₃)₂SO] δ 7.94 (s, 1H), 6.47 (br s, 2H, NH₂), 3.02 (d, J=4.0 Hz, 2H), 2.87 (d, J=4.1 Hz, 2H), 1.83 (m, 2H), 1.61 (m, 4H); HPLC 96.6%. LCMS found: [M+H]=204.

6,6-Dimethyl-5,6,7,8-tetrahydroisoxazolo[5,4-b]quinolin-3-amine (61)

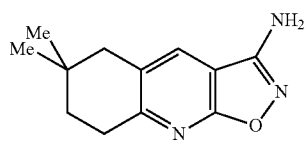

From 2-chloro-6,6-dimethyl-5,6,7,8-tetrahydroquinoline-3-carbonitrile, mp 203-205° C.; ¹H NMR [(CD₃)₂SO] δ 7.90 (s, 1H), 6.49 (br s, 2H, NH₂), 2.62 (s, 2H), 2.06 (t, J=6.9 Hz, 2H), 1.65 (t, J=6.9 Hz, 2H), 0.97 (s, 6H); HPLC 99.1%. LCMS found: [M+H]=218.

7,8-Dihydro-5H-isoxazolo[5,4-b]pyrano[3,4-e]pyridin-3-amine (62)

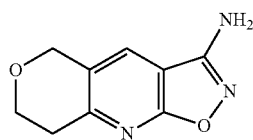

From 2-chloro-7,8-dihydro-5H-pyrano[4,3-b]pyridine-3-carbonitrile, mp 248-250° C.; ¹H NMR [(CD₃)₂SO] δ 7.94 (s, 1H), 6.57 (br s, 2H, NH₂), 4.81 (s, 2H), 4.00 (m, 2H), 2.97 (m, 2H); HPLC 97.8%. LCMS found: [M+H]=192.

6-(Methylthio)isoxazolo[5,4-d]pyrimidin-3-amine (63)

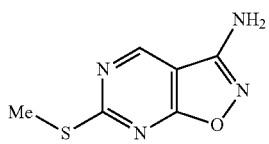

From 4-chloro-2-(methylthio)pyrimidine-5-carbonitrile, mp>310° C.; ¹H NMR [(CD₃)₂SO] δ 9.05 (s, 1H), 6.92 (br s, 2H, NH₂), 2.56 (s, 3H, SCH₃); HPLC 99.9%. LCMS found: [M+H]=183.

6-Methylisoxazolo[5,4-d]pyrimidin-3-amine (64)

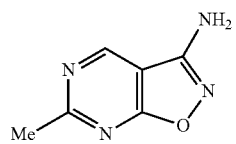

From 4-chloro 2-methylpyrimidine-5-carbonitrile, mp 180-182° C.; ¹H NMR (CD₃OD) δ 9.10 (s, 1H), 2.78 (s, 3H, CH₃); HPLC 97.9%. LCMS found: [M+H]=151.

4-(Methylthio)-6-phenylisoxazolo[5,4-d]pyrimidin-3-amine (65)

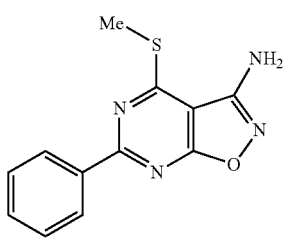

From 4-chloro-6-(methylthio)-2-phenylpyrimidine-5-carbonitrile, mp 230-233° C.; ¹H NMR [(CD₃)₂SO] δ 8.48 (m, 2H), 7.57 (m, 3H), 6.37 (br s, 2H, NH₂), 2.84 (s, 3H, SCH₃); HPLC 98.3%. LCMS found: [M+H]=259.

6-Chloro-5-fluoroisoxazolo[5,4-b]pyridin-3-amine (66)

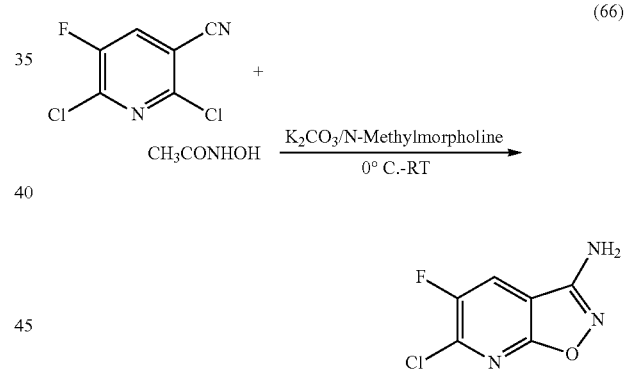

To a solution of acetohydroxamic acid (589 mg, 7.85 mmol) in N-methylmorpholine (10 mL) at 20° C. was added dry K₂CO₃ (1.08 g, 7.83 mmol) and the mixture was stirred for 1 hr at this temperature. This mixture was cooled in ice and 2,6-dichloro-5-fluoronicotinonitrile (1.00 g, 5.24 mmol) was added and the reaction mixture was allowed to warm up slowly to 20° C. and stirred at this temperature for 3 days. The reaction mixture was then diluted with H₂O and basified with K₂CO₃, extracted into EtOAc and dried (Na₂SO₄). Evaporation of the solvents gave a semisolid, which was chromatographed (SiO₂/X4/EtOAc, 0-20%). The fractions with the correct mass were combined and the solvents were evaporated. The resulting residue was triturated with DCM and MeOH to give (66) (2.0 mg, 0.2% yield), mp 243-245° C.; ¹H NMR [(CD₃)₂SO] δ 8.32 (d, J=7.6 Hz, 1H), 6.77 (brs, 2H); HPLC 99.4%; Anal. calcd. for C₆H₃ClFN₃O.0.25 MeOH: C, 38.38, H, 2.06; N, 21.49; found C, 38.32; H, 1.85, N, 21.54%.

5,6-Dichloroisoxazolo[5,4-b]pyridin-3-amine (67)

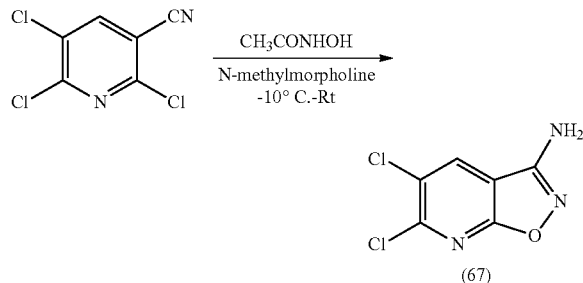

From 2,5,6-trichloronicotinonitrile and acetohydroxamic acid in N-methylmorpholine at room temperature for 3 days to give 67 (3% yield). $^1$H NMR [(CD$_3$)$_2$SO] δ 8.58 (s, 1H), 6.82 (brs, 2H), HPLC 96.5%, LCMS [M+H]=204/206.

6-Chloro-4-(trifluoromethyl)isoxazolo[5,4-b]pyridin-3-amine (68)

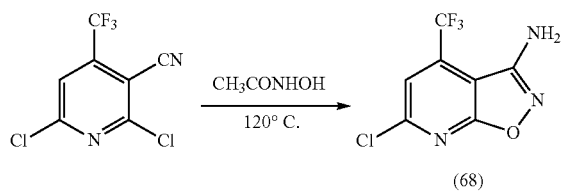

A neat mixture of 2,6-dichloro-4-(trifluoromethyl)nicotinonitrile (102 mg, 0.42 mmol) and acetohydroxamic acid (315 mg 4.2 mmol) was heated to 120° C. for 20 hr. The cooled reaction mixture was then diluted with H$_2$O, basified with K$_2$CO$_3$, extracted into EtOAc, and the solution dried (Na$_2$SO$_4$). Evaporation of the solvents and the chromatography of the residue (SiO$_2$/pet. ether/EtOAc 0-20%) gave 68 (4.0 mg, 4% yield), $^1$H NMR [(CD$_3$)$_2$SO] δ 7.95 (d, J=0.6 Hz, 1H), 6.24 (brs, 2H), HPLC 99.5%, LCMS [M+H]=238.

5-(3-Methoxyprop-1-yn-1-yl)isoxazolo[5,4-b]pyridin-3-amine (69)

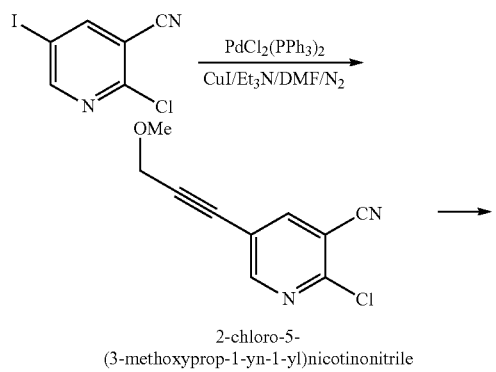

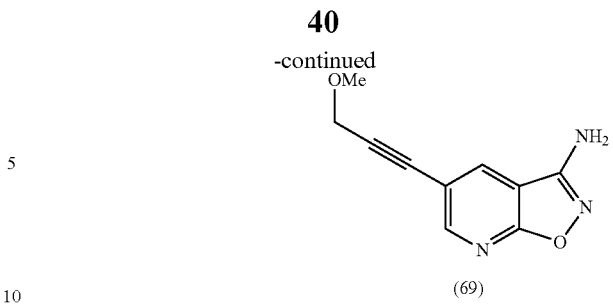

2-Chloro-5-iodonicotinonitrile (277 mg, 1.05 mmol), CuI (19.8 mg, 0.104 mmol) and PdCl$_2$(PPh$_3$)$_2$ (44 mg, 0.022 mmol) in DMF (6.0 ml) and Et$_3$N (6.0 ml) was degassed with N$_2$ in a sealed tube, then methylpropargyl ether (1.1 ml, 910 mg, 13 mmol) was added and the reaction mixture was stirred at 20° C. for 2 hr. The reaction mixture was diluted with H$_2$O, extracted into EtOAc and dried (Na$_2$SO$_4$). Evaporation of the solvents and chromatography of the residue on SiO$_2$/pet. ether/EtOAc (0-10%) gave 2-chloro-5-(3-methoxyprop-1-yn-1-yl)nicotinonitrile (103 mg, 47.4%); $^1$H NMR [(CD$_3$)$_2$SO] δ 8.80 (d, J=2.3 Hz, 1H), 8.67 (d, J=2.3 Hz, 1H), 4.39 (s, 2H), 3.59 (s, 3H), LCMS [M+H]=207. Further elution with 20% pet. ether/EtOAc gave the bis-addition product 2,5-bis((3-methoxyprop-1-yn-1-yl)oxy)nicotinonitrile (100 mg, 40%). $^1$H NMR [(CD$_3$)$_2$SO] δ 8.90 (d, J=2.1 Hz, 1H), 8.56 (d, J=2.1 Hz, 1H), 4.49 (s, 2H), 4.40 (s, 2H), 3.39 (s, 3H), 3.35 (s, 3H), LCMS [M+H]=241.

Similar ring closure of 2-chloro-5-(3-methoxyprop-1-yn-1-yl)nicotinonitrile in DMF with acetohydroxamic acid and KO$^t$Bu gave 69 in 24% yield, mp (DCM/pet. ether) 183-186° C.; 1H NMR [(CD$_3$)$_2$SO] δ 8.61 (d, J=2.1 Hz, 1H), 8.42 (d, J=2.1 Hz, 1H), 6.70 (brs, 2H), 4.37 (s, 2H), 3.37 (s, 3H); HPLC 99.9%; LCMS [M+H]=204, Anal. calcd for C$_9$H$_9$N$_3$O$_2$: C, 59.1, H, 4.5, N, 20.7; found C, 59.2, H, 4.3; N, 20.7%.

Method 2. Representative Example

N$^6$,N$^6$-Dimethylisoxazolo[5,4-b]pyridine-3,6-diamine (18)

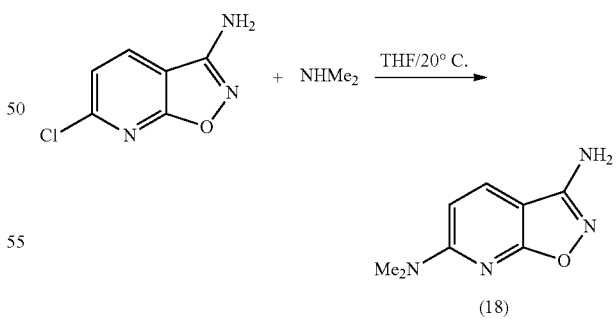

To a solution of 6-chloroisoxazolo[5,4-b]pyridin-3-amine in THF (15 ml) was added a 40% aqueous solution of dimethylamine (2 mL). The reaction mixture was stirred for 4 days at 20° C. The excess solvent was removed under vacuum and the resulting precipitate was filtered and the solid was collected. Extraction of the filtrate with EtOAc (20 mL×3) gave further material. The combined product was chromatographed on SiO$_2$ eluting with a 0-75% gradient of petroleum ether/EtOAc to give $N^6,N^6$-dimethylisoxazolo[5,4-b]pyridine-3,6-diamine (18) (81 mg; 77%) as a white solid; mp (DCM/petroleum ether) 238-241° C.; $^1$H NMR [(CD$_3$)$_2$SO] δ 7.85 (d, J=8.8 Hz, 1H), 6.57 (d, J=8.8 Hz, 1H), 1.13 (s, 2H, NH$_2$); 3.09 [s, 6H, N(CH$_3$)$_2$]. LCMS [M+H]=179; HPLC 99.7%; Anal. calcd. for $C_8H_{10}N_4O$: C, 53.9; H, 5.7; N, 31.4; found C, 54.1; H, 5.6; N, 31.5%.

Similarly was prepared $N^4,N^4$-Dimethylisoxazolo[5,4-b]pyridine-3,4-diamine (19)

(19)

From 4-chloroisoxazolo[5,4-b]pyridin-3-amine in 74% yield, mp (DCM/MeOH) 218-220° C.; LCMS [M+H]=179; HPLC 99.9%. HRMS (ESI$^+$) calcd. for $C_7H_{11}N_4O$ 179.0927; found 179.0926.

Method 2. Further Examples

General Experimental Procedure

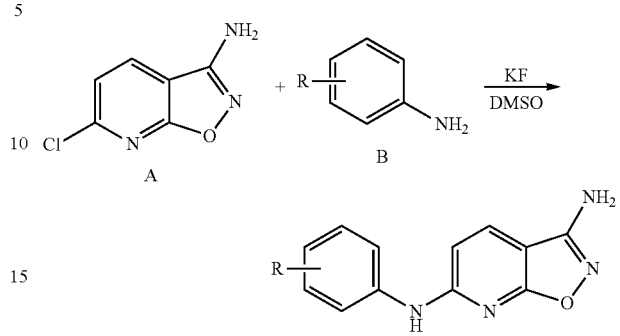

To a solution of A (1.0 eq) in DMSO was added B (2.0 eq) and KF (3.0 eq) and the resulting mixture was heated in a microwave reactor at 150° C. for 2 h. The reaction mixture was diluted with ethyl acetate, washed with water and brine, dried over anhydrous Na$_2$SO$_4$, filtered and concentrated. The residue was purified by prep. TLC (CH$_2$Cl$_2$/MeOH=20/1) to give the desired product.

The following compounds were prepared using the method described above:

| Compound Number | Structure | [M + H]$^+$ | $^1$H NMR spectrum |
|---|---|---|---|
| 94 | 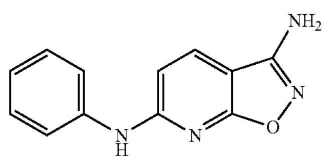 | 227.1 | 1H NMR (400 MHz, DMSO) δ 9.62 (s, 1H), 7.91 (d, J = 8.6 Hz, 1H), 7.72 (d, J = 7.6 Hz, 2H), 7.32 (t, J = 7.6 Hz, 2H), 6.98 (t, J = 7.6 Hz, 1H), 6.72 (d, J = 8.6 Hz, 1H), 6.24 (s, 2H). |
| 95 | 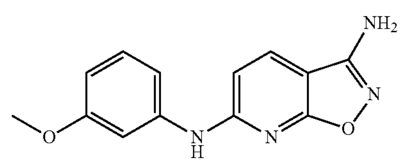 | 257.1 | 1H NMR (400 MHz, DMSO) δ 9.61 (s, 1H), 7.91 (d, J = 8.6 Hz, 1H), 7.45 (s, 1H), 7.26 (t, J = 8.0 Hz, 1H), 7.22 (t, J = 8.0 Hz, 1H), 6.71 (d, J = 8.6 Hz, 1H), 6.57 (dd, J$_1$ = 8.0 Hz, J$_2$ = 1.2 Hz, 1H), 6.25 (s, 2H), 3.76 (s, 3H). |
| 96 | 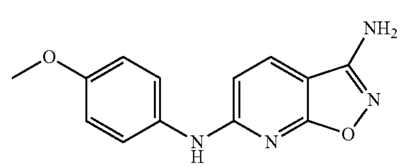 | 257.1 | 1H NMR (400 MHz, DMSO) δ 9.42 (s, 1H), 7.85 (d, J = 8.6 Hz, 1H), 7.59 (d, J = 9.0 Hz, 2H), 6.92 (d, J = 9.0 Hz, 2H), 6.62 (d, J = 8.6 Hz, 1H), 6.19 (s, 2H), 3.74 (s, 3H). |

Method 3. Representative Example

5-Chloro-$N^3$,4,6-trimethylisoxazolo[5,4-b]pyridin-3-amine (20)

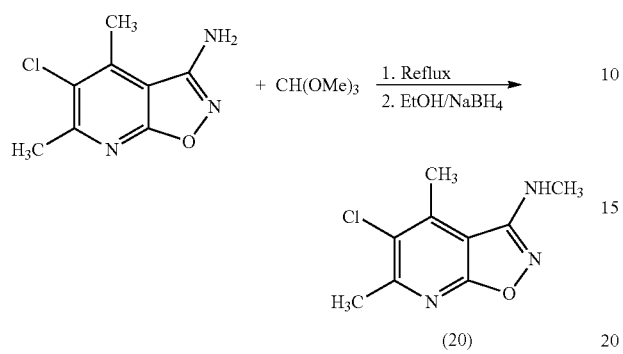

A mixture of 5-chloro-4,6-dimethylisoxazolo[5,4-b]pyridin-3-amine (0.21 mg, 1.05 mmol) in trimethylorthoformate (3 mL) was refluxed for 20 hr. The excess trimethylorthoformate was removed under vacuum and the residue was dissolved in ethanol (10 mL) and treated with $NaBH_4$ (284 mg, 7.7 mmol) and the mixture stirred at 20° C. for 3 hr, then at 50° C. for 20 hr. The reaction mixture was concentrated and the residue was stirred in $H_2O$ (50 mL). The resulting precipitate was filtered and washed with more water. The collected solid was purified by column chromatography on $SiO_2$, eluting with a gradient of 0-40% of petroleum ether/EtOAc. Recrystallizations from DCM/petroleum ether, then petroleum ether/EtOAc and finally $MeOH/H_2O$ gave the product, 5-chloro-$N^3$,4,6-trimethylisoxazolo[5,4-b]pyridin-3-amine (20) (50 mg, 22.5%); mp 167-170° C.; $^1H$ NMR [$(CD_3)_2SO$] δ 6.53 [(q, J=4.4 Hz 1H, NH($CH_3$)], 2.82 (d, J=4.9 Hz, 3H, $NCH_3$); 2.62 (s, 3H, $CH_3$), 2.60 (s, 3H, $CH_3$); LCMS [M+H]=212.5; HPLC 97.5%; Anal. calcd. for $C_9H_{10}ClN_3O$: C, 51.1; H, 4.8; N, 19.8; found C, 51.0; H, 4.5; N, 19.9%.

Method 4. Representative Example

5-Chloro-$N^3$,$N^3$,4,6-tetramethylisoxazolo[5,4-b]pyridin-3-amine (21)

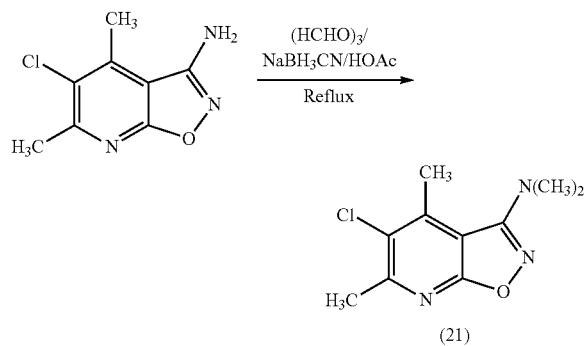

To a suspension of 5-chloro-4,6-dimethylisoxazolo[5,4-b]pyridin-3-amine (0.10 g, 0.506 mmol) in HOAc (5 mL) was added paraformaldehyde (0.65 g, 7.2 mmol) and $NaBH_3CN$ (0.45 g, 7.2 mmol). The reaction mixture was heated to 100° C. for 2 hr, cooled and. basified with aq $K_2CO_3$. The resulting precipitate was filtered, washed with $H_2O$ and chromatographed on $SiO_2$ eluting with a gradient of 0-75% petroleum ether/DCM to give 5-chloro-$N^3$,$N^3$,4,6-tetramethylisoxazolo[5,4-b]pyridin-3-amine (21) (45 mg; 39%); mp (DCM/petroleum ether) 112-113° C.; $^1H$ NMR [$(CD_3)_2SO$] δ 2.90 [s, 6H, N($CH_3$)$_2$], 2.65 (s, 3H, $CH_3$), 2.63 (s, 3H, $CH_3$); LCMS [M+H]=226.5; HPLC 98.3%; Anal. calcd. for $C_{10}H_{12}ClN_3O$: C, 53.2; H, 5.4; N, 18.6; found C, 53.1; H, 5.3; N, 18.5%.

Method 5. Representative Example 5-(3-Methoxyphenyl)isoxazolo[5,4-b]pyridin-3-amine (22)

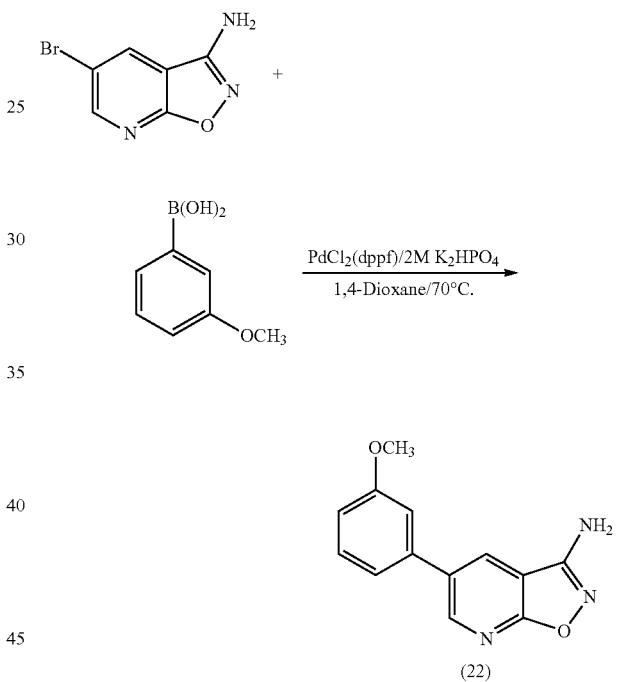

A mixture of 5-bromoisoxazolo[5,4-b]pyridin-3-amine (0.16 g, 0.76 mmol), (3-methoxyphenyl)boronic acid (0.23 g, 152 mmol) and 2M $K_2HPO_4$ (3 mL), in 1,4-dioxane (6 mL) was degassed with $N_2$. $PdCl_2$(dppf) (50 mg, 9% mol) was added and the reaction mixture was stirred and heated at 70° C. overnight. Dioxane was evaporated under vacuum and the residue was partitioned between water and EtOAc. The combined organic extracts were dried ($Na_2SO_4$) and the solvent evaporated. The residue was chromatographed on silica, eluting with a gradient of 0-30% of petroleum ether/EtOAc to give 5-(3-methoxyphenyl)isoxazolo[5,4-b]pyridin-3-amine (22) (66 mg, 36%), mp (EtOAc/petroleum ether) 200-202° C., $^1H$ NMR [$(CD_3)_2SO$] δ 8.83 (d, J=2.3 Hz, 1H), 8.59 (d, J=2.3 Hz, 1H), 7.45 (t, J=8.1 Hz, 1H), 7.28-7.26 (m, 2H), 7.02-7.03 (m, 1H), 7.00-6.99 (m, 1H), 6.68 (s, 2H, $NH_2$), 3.85 (s, 3H, $OCH_3$), LCMS [M+H]=242, HPLC: 98.2%, Anal. calcd. for $C_{13}H_{11}N_3O_2$: C, 64.7; H, 4.6; N, 17.4; found C, 64.7; H, 4.6, N, 17.4%.

Similarly were prepared:

5-(2-Methoxyphenyl)isoxazolo[5,4-b]pyridin-3-amine (23)

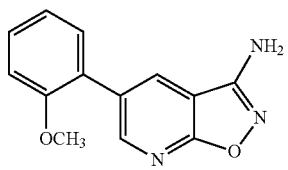
(23)

From (2-methoxyphenyl)boronic acid in 19% yield; mp (DCM/petroleum ether) 191-193° C.; HPLC 98.6%: HRMS (ESI$^+$) calcd. for $C_{13}H_{12}N_3O_2$ 242.0924; found 242.0928.

5-Phenylisoxazolo[5,4-b]pyridin-3-amine (24)

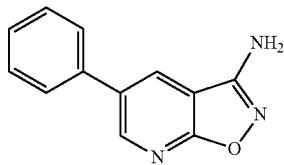
(24)

From 5-bromoisoxazolo[5,4-b]pyridin-3-amine and phenylboronic acid in 13% yield; mp (DCM/MeOH) 249-252° C.; LCMS [M+H]=212; HPLC 99.3%. Anal. calcd. for $C_7H_9N_3O.1/4\ H_2O$; C, 67.5; H, 4.4; N, 19.7; found; C, 67.4; H, 4.2; N, 19.8%.

5-(3-Fluoro-4-methoxyphenyl)isoxazolo[5,4-b]pyridin-3-amine (25)

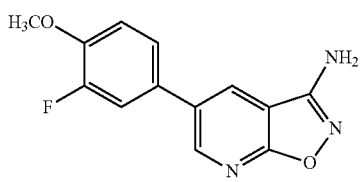
(25)

From (3-fluoro-4-methoxyphenyl)boronic acid in 18% yield; mp (DCM/MeOH) 258-261° C.; LCMS [M+H]=260; HPLC 99.6%; Anal. calc. for $C_{13}H_{10}FN_3O$: C, 60.2; H, 4.0; N, 16.2; found C, 60.1; H, 3.8; N, 16.2%.

5-(Pyridin-3-yl)isoxazolo[5,4-b]pyridin-3-amine (26)

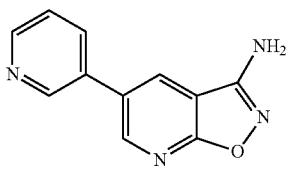
(26)

From 3-pyridylboronic acid in 6% yield; mp (MeOH) 239-242° C.; HPLC 98.8%; HRMS (ESI$^+$) calcd. for $C_{11}H_9N_4O$ 213.0771; found 213.0779.

5-(Pyridin-4-yl)isoxazolo[5,4-b]pyridin-3-amine (27)

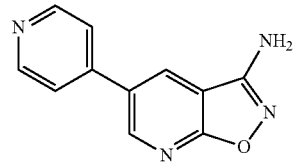
(27)

From 4-pyridylboronic acid in 6% yield; mp (DCM/MeOH) 291-294° C.; HPLC 98.6%; HRMS (ESI$^+$); calcd. for $C_{11}H_9N_4O$ 213.0771; found 213.0774.

2-(3-Aminoisoxazolo[5,4-b]pyridin-5-yl)phenol (28)

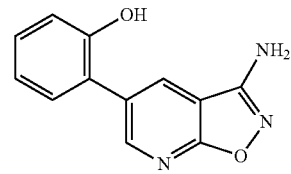
(28)

From (2-hydroxyphenyl)boronic acid in 4% yield; mp (MeOH/H$_2$O) 208-211° C.; HPLC 95.7%; HRMS (ESI$^+$) calcd. for $C_{12}H_{10}N_3O_2$ 228.0768; found 228.0771.

4-(3-Aminoisoxazolo[5,4-b]pyridin-5-yl)phenol (29)

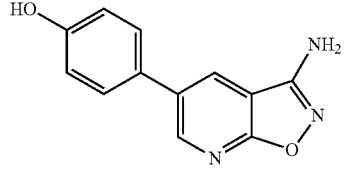
(29)

From (4-hydroxyphenyl)boronic acid in 4% yield; mp (MeOH) 272-275° C.; HPLC 99.6%. HRMS (ESI$^+$) calcd. for $C_{12}H_{10}N_3O_2$ 228.0768; found 228.0763.

5-(4-Fluorophenyl)isoxazolo[5,4-b]pyridin-3-amine (30)

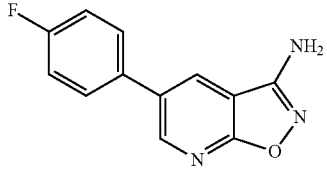
(30)

From (4-fluorophenyl)boronic acid in 16% yield; mp (MeOH) 235-238° C.; HPLC 99.6%; Anal. calcd. for C$_{12}$H$_8$FN$_3$O: C, 62.9; H, 3.5; N, 18.3; found C, 62.3; H, 3.4; N, 18.3%.

5-(3-Fluorophenyl)isoxazolo[5,4-b]pyridin-3-amine (31)

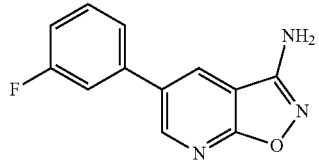

(31)

From (3-fluorophenyl)boronic acid in 38% yield; mp (MeOH) 233-236° C.; HPLC 98.4%; Anal. calcd. for C$_{12}$H$_8$FN$_3$O: C, 62.9; H, 3.5; N, 18.3; found C, 62.5; H, 3.5; N, 18.1%.

5-(2,4-difluorophenyl)isoxazolo[5,4-b]pyridin-3-amine (32)

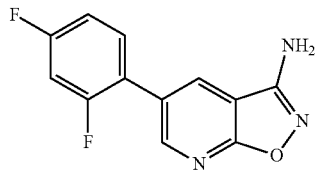

(32)

From (2,4-difluorophenyl)boronic acid in 18% yield; mp (MeOH) 258-261° C.; HPLC 99.5%; Anal. calcd. for C$_{12}$H$_7$F$_2$N$_3$O: C, 58.3; H, 2.8; N, 17.0; found C, 58.2; H, 2.7; N, 16.9%.

5-(3,5-Difluoro-2-methoxyphenyl)isoxazolo[5,4-b]pyridin-3-amine (33)

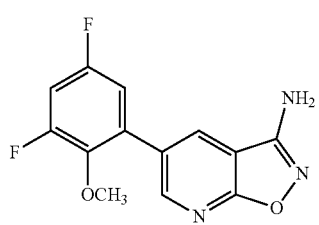

(33)

From (3,5-difluoro-2-methoxyphenyl)boronic acid in 5% yield; mp (MeOH) 210-211° C.; HPLC 99%; HRMS (ESI$^+$) calcd. for C$_{13}$H$_{10}$F$_2$N$_3$O$_2$ 278.0737; found 278.0736.

5-(2,4-Dichlorophenyl)isoxazolo[5,4-b]pyridin-3-amine (34)

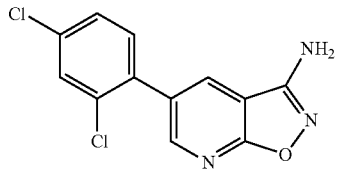

(34)

From (2,4-dichlorophenyl)boronic acid in 5% yield; mp (petroleum ether/EtOAc) 233-236° C.; HPLC 97%; Anal. calcd. for C$_{12}$H$_7$Cl$_2$N$_3$O; C, 51.4; H, 2.5; N, 15.0; found C, 51.3; H, 2.6; N, 14.8%.

5-(2,3,4-Trichlorophenyl)isoxazolo[5,4-b]pyridin-3-amine (35)

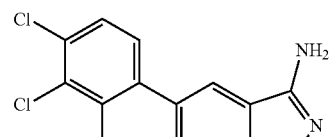

(35)

From (2,3,4-trichlorophenyl)boronic acid in 3% yield; mp (DCM/MeOH) 250-153° C.; HPLC 97.5% LCMS [M+H] 314 and 316. HRMS (ESI$^+$) calcd. for C$_{12}$H$_7$Cl$_3$N$_3$O 313.9648; found 313.9649.

5-(4-(Trifluoromethylphenyl)isoxazolo[5,4-b]pyridin-3-amine (36)

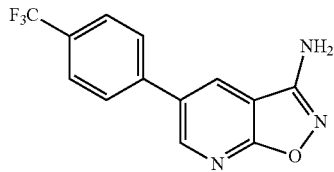

(36)

From (4-trifluoromethylphenyl)boronic acid in 17% yield; mp (MeOH) 267-270° C.; HPLC 99.9%; LCMS (M+H) 281; Anal. calcd. for C$_{13}$H$_8$F$_3$N$_3$O: C, 55.9; H, 3.0; N, 15.0; found C, 55.8; H, 2.8; N, 15.0%.

5-(3-Aminophenyl)isoxazolo[5,4-b]pyridin-3-amine (37)

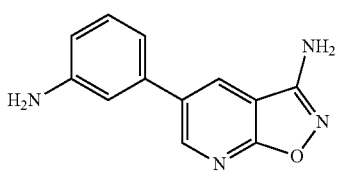

(37)

From (3-aminophenyl)boronic acid in 83% yield; mp (MeOH/H$_2$O) 220-221° C.; HPLC 96.0%; LCMS (M+H) 227; Anal. calcd. for C$_{12}$H$_{10}$N$_4$O: C, 63.7; H, 4.5; N, 24.8; C, 64, H, 4.5; N, 24.5%.

Methyl 3-(3-aminoisoxazolo[5,4-b]pyridin-5-yl)benzoate (38)

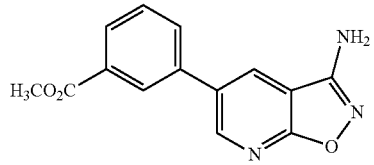

(38)

From (3-(methoxycarbonyl)phenyl)boronic acid in 28% yield; mp (MeOH) 221-223° C.; HPLC 98.2%; LCMS (M+H) 270; Anal. calcd. for C$_{14}$H$_{11}$N$_3$O$_3$: C, 62.4; H, 4.1; N, 15.6; found C, 62.1; H, 4.1; N, 15.6%.

5-(6-Fluoropyridin-3-yl)isoxazolo[5,4-b]pyridin-3-amine (39)

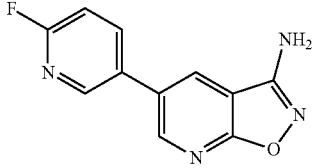

(39)

From (6-fluoropyridin-3-yl)boronic acid in 37% yield; mp (MeOH) 278-281° C.; HPLC 99.4%; HRMS (ESI$^+$) calcd. for C$_{11}$H$_8$FN$_4$O 231.0677; found 231.0680.

5-(2-Chloro-4-(trifluoromethyl)phenyl)isoxazolo[5,4-b]pyridin-3-amine (40)

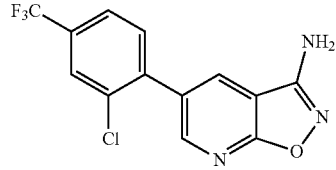

(40)

From (2-chloro-4-(trifluoromethyl)phenyl)boronic acid in 8.2% yield; mp (MeOH) 195-198° C.; LCMS [M+H]=314; HPLC 98.5%; Anal. calcd. for C$_{13}$H$_7$ClF$_3$N$_3$O: C, 49.2; H, 2.2; N, 13.4; found C, 49.7; H, 2.1; N, 13.3%.

Method 6. Representative Procedure and Further Examples 6-(4-Methoxyphenyl)isoxazolo[5,4-b]pyridin-3-amine (70)

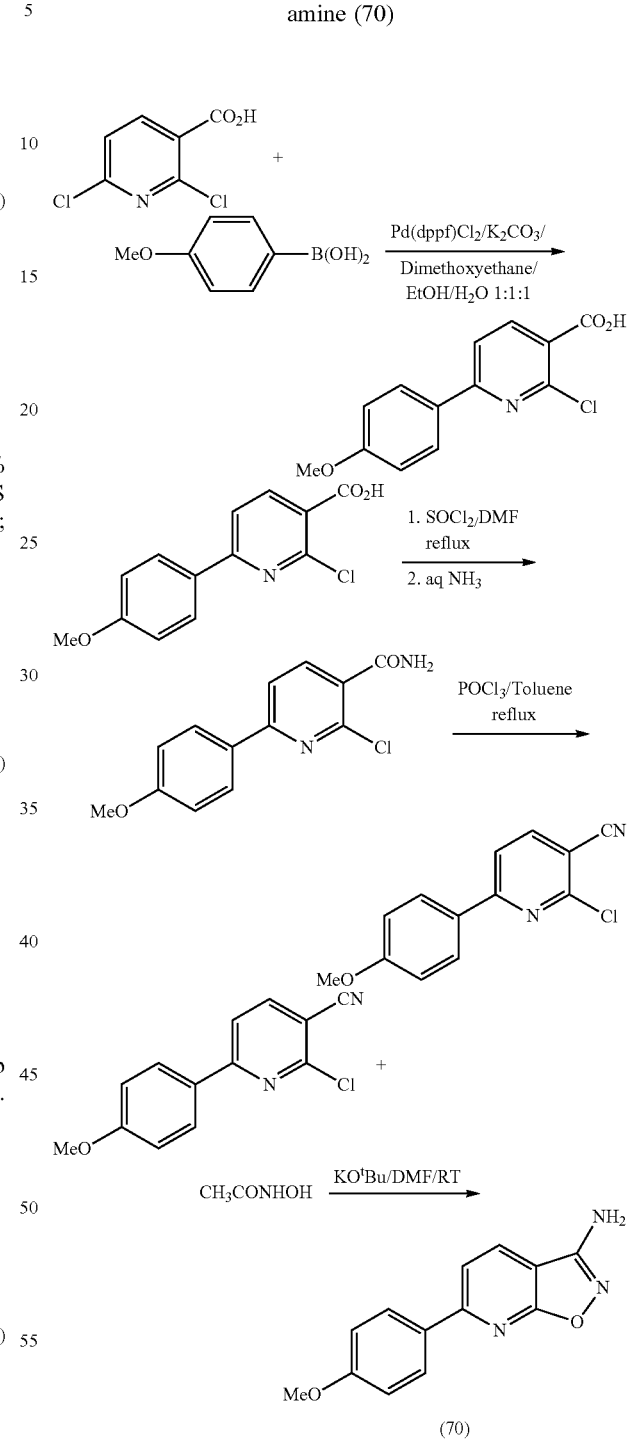

A mixture of 2,6-dichloronicotinic acid (1.0 g, 5.21 mmol), 4-methoxyphenylboronic acid (0.96 g, 1.15 mmol, 1.2 eq) K$_2$CO3 (2.5 g, 3.5 eq) in dimethoxyethane (6 ml), EtOH (6 ml) and H$_2$O (6 ml) was degassed with N$_2$, then Pd(dppf)Cl$_2$ (180 mg) was added and the reaction mixture was refluxed 2 hr under N$_2$. The mixture was evaporated to dryness and the resulting solid was stirred in EtOAc and filtered. The collected solid was dissolved in a small amount of water and the solution was carefully acidified with 2M HCl. The resulting precipitate was filtered and the mother liquor was further extracted with EtOAc and dried (Na$_2$SO$_4$). Evaporation of the solvent gave further material. Both solids were combined and recrystallized from MeOH/DCM to give 2-chloro-6-(4-methoxyphenyl)nicotinic acid (196 mg, 16%); $^1$H NMR [(CD$_3$)$_2$SO] δ 13.62 (br, 1H, CO$_2$H), 8.25 (d, J=8.1 Hz, 1H), 8.09 (d, J=8.9 Hz, 2H), 8.03 (s, J=8.1 Hz, 1H), 7.09 (d, J=8.9 Hz, 2H), 3.84 (s, 3H, OCH$_3$). This was used directly without further purification.

A mixture of 2-chloro-6-(4-methoxyphenyl)nicotinic acid (196 mg, 0.74 mmol) and SOCl$_2$ (10 ml) with a trace of DMF was refluxed for 2 h. The excess SOCl$_2$ was removed under vacuum and the resulting residue was dissolved in dry 1,4-dioxane and cooled in ice. Aqueous NH$_3$ (10 ml) was added and the solution was stirred for 20 h at room temperature. The solvent was removed under vacuum and the resulting precipitate was filtered, washed with water and dried to give 2-chloro-6-(4-methoxyphenyl)nicotinamide (153 mg 78%); $^1$H NMR [(CD$_3$)$_2$SO] δ 8.05 (d, J=8.6 Hz, 2H), 8.01 (brs, 1H), 7.98-7.91 (m, 2H), 7.73 (brs, 1H), 7.07 (d, J=8.6 Hz, 2H), 3.83 (s, 3H). This was used directly without further purification.

2-Chloro-6-(4-methoxyphenyl)nicotinamide (153 mg, 0.58 mmol) was refluxed in a mixture of toluene (3 mL) and POCl$_3$ (0.5 ml) for 1 hr. The reaction mixture was cooled to 20° C. and carefully basified with aq. K$_2$CO$_3$ and extracted with EtOAc, then dried (Na$_2$SO$_4$). Evaporation of the solvent and chromatography of the residue (SiO$_2$/0-20% pet. ether/EtOAc) gave 2-chloro-6-(4-methoxyphenyl)nicotinonitrile (120 mg, 84%); $^1$H NMR (CDCl$_3$) δ 8.03 (d, J=9.0 Hz, 2H), 7.96 (d, J=8.2 Hz, 1H), 7.70 (d, J=8.2 Hz, 1H), 7.01 (d, J=9.0 Hz, 2H), 3.89 (s, 3H). This was used without further purification.

Ring closure of 2-chloro-6-(4-methoxyphenyl)nicotinonitrile using acetohydroxamic acid and KO$^t$Bu in DMF, according to general Method 1 gave (70) in 57% yield, mp (DCM/MeOH) 249-252° C., $^1$H NMR [(CD$_3$)$_2$SO] δ 8.29 (d, J=8.2 Hz, 1H), 8.12 (brd, J=9.0 Hz, 2H), 7.90 (d, J=8.2 Hz, 1H), 7.08 (brd, J=9.0 Hz, 2H), 6.60 (s, 2H, NH$_2$), 3.84 (s, 3H, OCH$_3$); HPLC 96.4%; LCMS [M+H]=242.5; Anal. calcd. for C$_{13}$H$_{11}$N$_3$O$_2$: C, 64.7; H, 4.6, N, 17.4; found C, 64.4; H, 4.4; N, 17.4%.

6-(4-Fluorophenyl)isoxazolo[5,4-b]pyridin-3-amine (71)

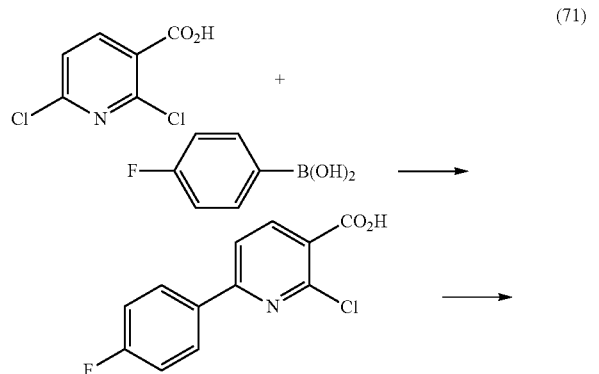

Similar Suzuki coupling of 2,6-dichloronicotinic acid with (4-fluorophenyl)boronic acid gave 2-chloro-6-(4-fluorofluorophenyl)nicotinic acid in 49% yield; $^1$H NMR [(CD$_3$)$_2$SO] δ 13.72 (br s, 1H), 8.31 (d, J=8.1 Hz, 1H), 8.19 (br dd, J=9.0, 5.5 Hz, 1H), 8.10 (d, J=8.1 Hz, 1H), 7.38 (t, J=8.9 Hz, 1H), This was used directly without further purification.

Reaction of 2-chloro-6-(4-fluorophenyl)nicotinic acid with thionyl chloride followed by reaction with aq. NH$_3$ gave 2-chloro-6-(4-fluorophenyl)nicotinamide; 1H NMR [(CD$_3$)$_2$SO] δ 8.17-8.13 (m, 2H), 8.05-8.36 (m, 2H), 7.98 (d, J=7.9 Hz, 1H), 7.67 (br s, 1H), 7.38-7.34 (m, 2H). This was refluxed in POCl$_3$/toluene to give 2-chloro-6-(4-fluorophenyl)nicotinonitrile in 83% yield over two steps; $^1$H NMR [(CD$_3$)$_2$SO] δ 8.55 (d, J=8.2 Hz, 1H), 8.26-8.21 (m, 3H), 7.43-7.37 (m, 2H).

Reaction of 2-chloro-6-(4-fluorophenyl)nicotinonitrile with acetohydroxamic acid and KO$^t$Bu in DMF gave (71) in 21% yield, MP (DCM/pet. ether) 265-268° C.; $^1$H NMR [(CD$_3$)$_2$SO] δ 8.35 (d, J=8.2 Hz, 1H), 8.22 (dd, J=9.0, 5.5 Hz, 2H), 7.96 (d, J=8.2 Hz, 1H), 7.37 (t, J=8.0 Hz, 2H), 6.65 (s, 2H); HPLC 99.8%; Anal calc. for C$_{12}$H$_8$FN$_3$O; C, 61.7; H, 3.7; N, 18.0; found C, 61.8; H, 3.6; N, 18.1%.

6-(2,4-Dichlorophenyl)isoxazolo[5,4-b]pyridin-3-amine (72)

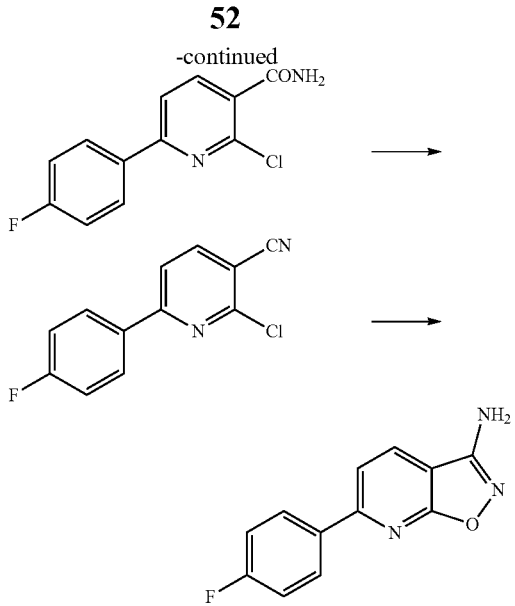

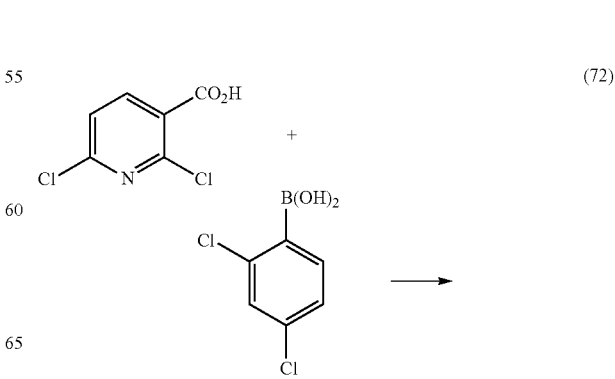

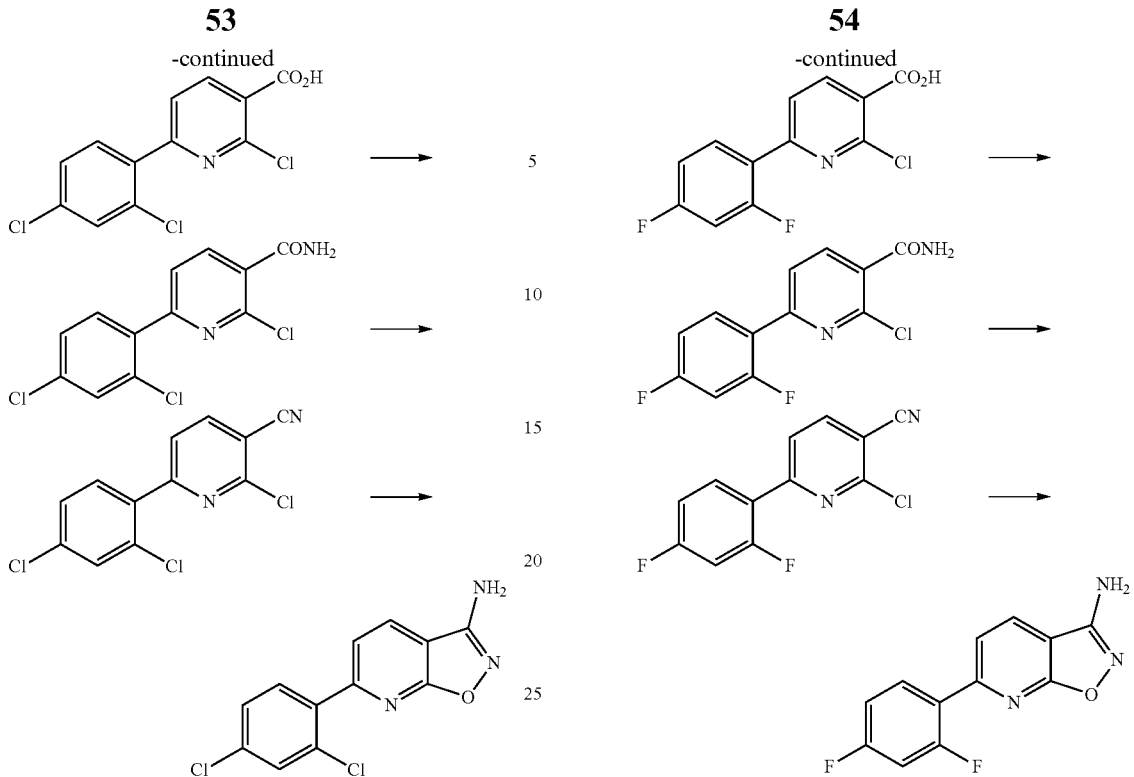

Similar Suzuki coupling of 2,6-dichloronicotinic acid and (2,4-dichlorophenyl)boronic acid followed by treatment with thionyl chloride and aqueous NH₃ gave 2-chloro-6-(2,4-dichlorophenyl)nicotinamide. Reaction of this with POCl₃/toluene under reflux gave 2-chloro-6-(2,4-dichlorophenyl)nicotinonitrile in 15% overall yield; ¹H NMR [(CD₃)₂SO δ 8.61 (d, J=8.0 Hz, 1H), 7.98 (d, J=8.1 Hz, 1H), 7.85 (d, J=2.0 Hz, 1H), 7.69 (d, J=8.4 Hz, 1H), 7.62 (dd, J=8.4, 2.0 Hz, 1H); LCMS [M+H]=279.

Reaction of 2-chloro-6-(2,4-dichlorophenyl)nicotinonitrile with acetohydroxamic acid and KO$^t$Bu in DMF gave (72) in 41% yield, mp (DCM/pet. ether) 231-233° C.; ¹H NMR [(CD₃)₂SO δ 8.40 (d, J=8.0 Hz, 1H), 7.80 (d, J=2.0 Hz, 1H), 7.66 (d, J=8.3 Hz, 1H), 7.63 (d, J=8.0 Hz, 1H), 7.59 (dd, J=8.4, 2.1 Hz, 1H), 6.73 (s, 2H); HPLC 99.3%; Anal. calcd. for C₁₂H₇Cl₂N₃O: C, 51.5; H, 2.5; N, 15.0; found: C, 51.6; H, 2.4; N, 15.1%.

6-(2,4-Difluorophenyl)isoxazolo[5,4-b]pyridin-3-amine (73)

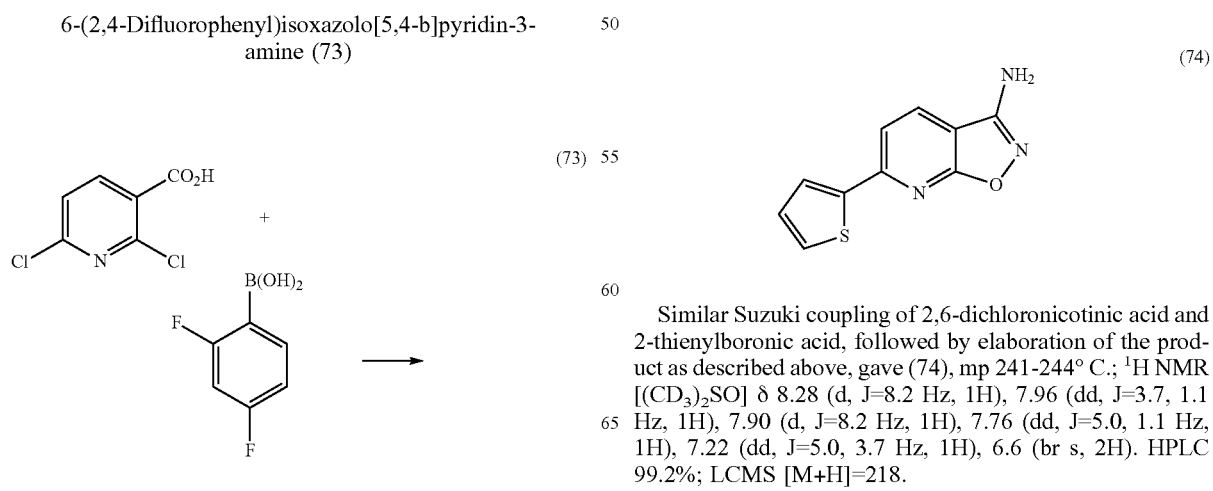

Similar Suzuki coupling of 2,6-dichloronicotinic acid and (2,4-difluorophenyl)boronic acid followed by thionyl chloride/aqueous NH₃ gave 2-chloro-6-(2,4-difluorophenyl)nicotinamide and treatment of this material with POCl₃/toluene under reflux gave 2-chloro-6-(2,4-difluorophenyl)nicotinonitrile in 19% yield; ¹H NMR [(CD₃)₂SO] δ 8.57 (d, J=8.1 Hz, 1H), 8.08-7.99 (m, 2H), 7.50 (ddd, J=11.8, 9.2, 2.5 Hz, 1H), 7.34-7.29 (m, 1H).

Reaction of 2-chloro-6-(2,4-difluorophenyl)nicotinonitrile with acetohydroxamic acid and KO$^t$Bu in DMF gave (73) in 74% yield, mp (DCM/pet. ether) 235-238° C.; ¹H NMR [(CD₃)₂SO δ 8.39 (d, J=8.1 Hz, 1H), 8.04 (dt, J=8.9, 6.7 Hz, 1H), 7.76 (dd, J=8.1, 2.0 Hz, 1H), 7.45 (ddd, J=11.7, 9.3, 2.5 Hz, 1H), 7.31-7.26 (m, 1H), 6.71 (s, 2H); HPLC 97.8%.

6-(2-Thienyl)isoxazolo[5,4-b]pyridin-3-amine (74)

(74)

Similar Suzuki coupling of 2,6-dichloronicotinic acid and 2-thienylboronic acid, followed by elaboration of the product as described above, gave (74), mp 241-244° C.; ¹H NMR [(CD₃)₂SO] δ 8.28 (d, J=8.2 Hz, 1H), 7.96 (dd, J=3.7, 1.1 Hz, 1H), 7.90 (d, J=8.2 Hz, 1H), 7.76 (dd, J=5.0, 1.1 Hz, 1H), 7.22 (dd, J=5.0, 3.7 Hz, 1H), 6.6 (br s, 2H). HPLC 99.2%; LCMS [M+H]=218.

6-(1-Methyl-1H-pyrazol-5-yl)isoxazolo[5,4-b]pyridin-3-amine (75)

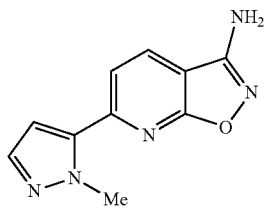
(75)

Similar Suzuki coupling of 2,6-dichloronicotinic acid and (1-methyl-1H-pyrazol-5-yl)boronic acid, followed by elaboration of the product as described above gave (75); $^1$H NMR [CD$_3$OD] δ 8.29 (d, J=8.2 Hz, 1H), 7.72 (d, J=8.2 Hz, 1H), 7.54 (d, J=2.1 Hz, 1H), 6.89 (d, J=2.1 Hz, 1H), 4.27 (s, 3H); HPLC 97%; ESI$^+$ Found 216.0872, C$_{10}$H$_9$N$_5$O requires 216.0880.

Method 7. Representative Example

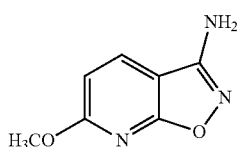
(41)

To a solution formed by adding sodium (129 mg, 5.6 mmol) to dry MeOH (3 mL) at 20° C. was added 6-chloroisoxazolo[5,4-b]pyridin-3-amine (16 mg, 0.09 mmol) and the solution was stirred at 20° C. for 20 hr. The reaction mixture was then evaporated to dryness, and the resulting residue was stirred in H$_2$O (10 mL) to give a white precipitate, which was filtered, washed with H$_2$O and dried at 100° C. to give 6-methoxyisoxazolo[5,4-b]pyridin-3-amine (41) (7 mg, 46%), mp (H$_2$O), 213-215° C.; $^1$H NMR [(CD$_3$)$_2$SO] δ 8.10 (d, J=8.5 Hz, 1H), 6.75 (d, J=8.5 Hz, 1H), 6.42 (bs, 2H, NH$_2$), 3.91, (s, 3H, OCH$_3$), HPLC 99.8%; HRMS (ESI$^{+)}$ calcd. for C$_7$H$_8$N$_3$O$_2$ 166.0611; found 166.0606.

Method 7 Further Examples

6-(3-(Dimethylamino)propoxy)isoxazolo[5,4-b]pyridin-3-amine (76)

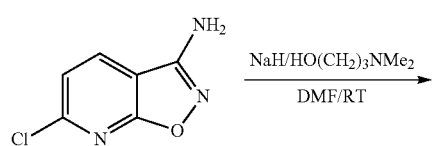

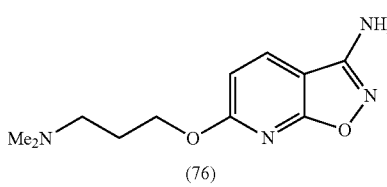
(76)

Similarly from 6-chloroisoxazolo[5,4-b]pyridine-3-amine and N,N-dimethylaminopropanol in 33% yield, mp (DCM/pet. ether) 164-166° C.; $^1$H NMR [(CD$_3$)$_2$SO] δ 8.09 (d, J=8.5 Hz, 1H), 6.73 (d, J=8.5 Hz, 1H), 6.41 (brs, 2H), 4.32 (t, J=6.6 Hz, 2H), 2.35 (t, J=7.1 Hz, 2H), 2.14 (s, 6H), 1.86 (p, J=6.8 Hz, 1H); HPLC 99.7%; HRMS (ESI$^+$) calcd. for C$_{11}$H$_{17}$N$_4$O$_2$ [M+H] 237.1346, found 237.1346.

6-(2-(Dimethylamino)ethoxy)isoxazolo[5,4-b]pyridin-3-amine(77)

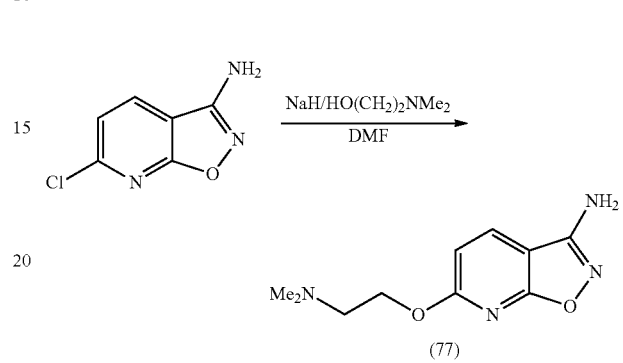
(77)

Similarly from 6-chloroisoxazolo[5,4-b]pyridine-3-amine and N,N-dimethylaminoethanol in 43% yield, mp DCM/pet. ether) 168-170° C.; $^1$H NMR [(CD$_3$)$_2$SO] δ 8.09 (d, J=8.5 Hz, 1H), 6.73 (d, J=8.5 Hz, 1H), 6.42 (brs, 2H), 4.38 (t, J=5.8 Hz, 2H), 2.63 (t, J=5.8 Hz, 2H), 2.20 (s, 6H); HPLC 99.9%; HRMS (ESI$^+$) calcd. for C$_{10}$H$_{15}$N$_4$O$_2$[M+H] 223.1190, found 223.1197.

6-(2-Morpholinoethoxy)isoxazolo[5,4-b]pyridin-3-amine (78)

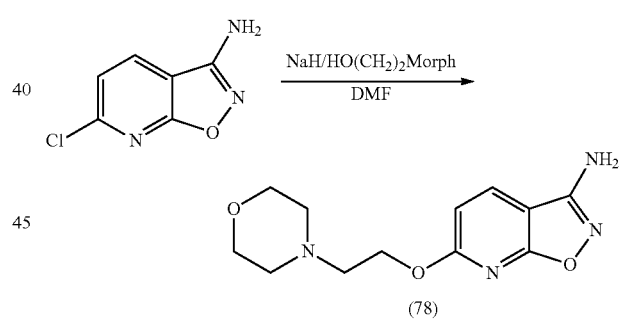
(78)

Similarly from 6-chloroisoxazolo[5,4-b]pyridine-3-amine and 2-morpholinoethanol in 24% yield, mp (DCM/pet. ether) 151-153° C.; $^1$H NMR [CD$_3$)$_2$SO] δ 8.10 (d, J=8.5 Hz, 1H), 6.75 (d, J=8.5 Hz, 1H), 6.42 (brs 2H), 4.42 (brm, 2H), 3.56 (brm, 4H), 2.70 (brm, 2H), 2.40 (brm, 4H); HPLC 99.9%; HRMS (ESI$^+$) calcd. for C$_{12}$H$_{17}$N$_4$O$_3$ [M+H] 265.1295, found 265.1295.

General Method:

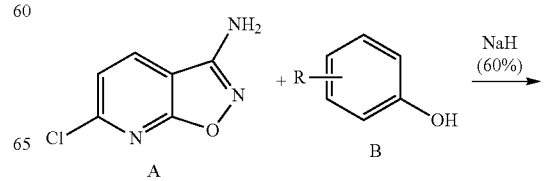

-continued

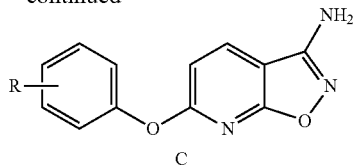

C

To a solution of B (2.0 eq) in DMF at 0° C. was added NaH (60% dispersion in mineral oil, 1.9 eq) and the reaction mixture was stirred at room temperature for 30 min. Then A (1.0 eq) was added and the resulting mixture was stirred at 90° C. for 6-16 h (monitored by TLC). The reaction mixture was diluted with ethyl acetate and washed with water and brine. The organic layer was dried over anhydrous $Na_2SO_4$, filtered and concentrated to give the crude product, which was purified by column chromatography on silica gel (pet. ether/ethyl acetate=3/1) to give the desired product.

The following compounds C were prepared by this general method:

| Compound Number | Structure | $[M + H]^+$ | $^1H$ NMR |
|---|---|---|---|
| 83 | 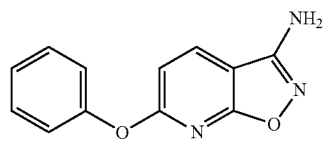 [SMILES: Nc1noc2nc(Oc3ccccc3)ccc12] | 227.9 | $^1$H NMR (400 MHz, DMSO-d6) δ 8.26 (d, J = 8.4 Hz, 1H), 7.47 (t, J = 7.9 Hz, 2H), 7.28 (t, J = 7.2 Hz, 1H), 7.21 (d, J = 7.6 Hz, 2H), 6.97 (d, J = 8.4 Hz, 1H), 6.52 (s, 2H). |
| 84 | 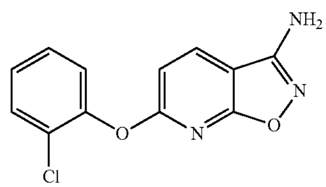 [SMILES: Nc1noc2nc(Oc3ccccc3Cl)ccc12] | 262.0<br>264.0 | $^1$H NMR (400 MHz, DMSO-d6) δ 8.30 (d, J = 8.4 Hz, 1H), 7.62 (dd, $J_1$ = 8.0 Hz, $J_2$ = 1.2 Hz, 1H), 7.49-7.32 (m, 3H), 7.07 (d, J = 8.4 Hz, 1H), 6.54 (s, 2H). |
| 85 | 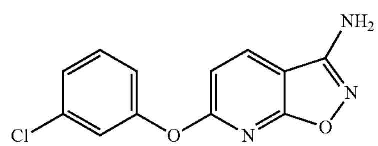 [SMILES: Nc1noc2nc(Oc3cccc(Cl)c3)ccc12] | 262.0<br>264.0 | $^1$H NMR (400 MHz, DMSO-d6) δ 8.29 (d, J = 8.4 Hz, 1H), 7.49 (t, J = 8.0 Hz, 1H), 7.39-7.35 (m, 2H), 7.21 (dd, $J_1$ = 8.0 Hz, $J_2$ = 1.2 Hz, 1H), 7.02 (d, J = 8.4 Hz, 1H), 6.55 (s, 2H). |
| 86 | 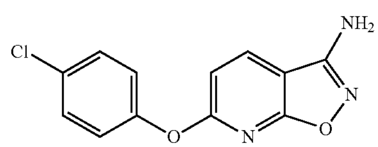 [SMILES: Nc1noc2nc(Oc3ccc(Cl)cc3)ccc12] | 262.0<br>264.0 | 1H NMR (400 MHz, DMSO-d6) δ 8.27 (d, J = 8.8 Hz, 1H), 7.51 (d, J = 8.8 Hz, 2H), 7.27 (d, J = 8.8 Hz, 2H), 7.01 (d, J = 8.4 Hz, 1H), 6.54 (s, 2H). |
| 87 | 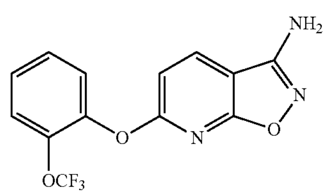 [SMILES: Nc1noc2nc(Oc3ccccc3OC(F)(F)F)ccc12] | 312.1 | $^1$H NMR (400 MHz, DMSO-d6) δ 8.32 (d, J = 8.4 Hz, 1H), 7.57-7.41 (m, 4H), 7.09 (d, J = 8.4 Hz), 6.57 (s, 2H) |
| 88 | 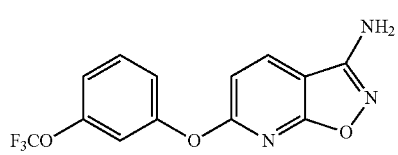 [SMILES: Nc1noc2nc(Oc3cccc(OC(F)(F)F)c3)ccc12] | 312.1 | 1H NMR (400 MHz, DMSO-d6) δ 8.30 (d, J = 8.4 Hz, 1H), 7.59 (t, J = 8.0 Hz, 1H), 7.28-7.33 (m, 3H), 7.04 (d, J = 8.4 Hz, 1H), 6.55 (s, 2H). |
| 89 | 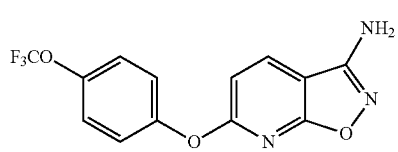 [SMILES: Nc1noc2nc(Oc3ccc(OC(F)(F)F)cc3)ccc12] | 312.0 | 1H NMR (400 MHz, DMSO-d6) δ 8.29 (d, J = 8.4 Hz, 1H), 7.47 (d, J = 8.4 Hz), 7.39-7.35 (m, 2H), 7.04 (d, J = 8.4 Hz, 1H), 6.55 (s, 2H). |

-continued

| Compound Number | Structure | [M + H]+ | 1H NMR |
|---|---|---|---|
| 90 | (structure: 2-methoxyphenoxy-isoxazolo[5,4-b]pyridin-3-amine) | 258.1 | 1H NMR (400 MHz, DMSO-d6) δ 8.23 (d, J = 8.4 Hz, 1H), 7.32-7.24 (m, 1H), 7.18 (ddd, $J_1$ = 8.1 Hz, $J_2$ = 4.3 Hz, $J_3$ = 1.4 Hz, 2H), 7.01 (td, $J_1$ = 7.7 Hz, $J_2$ = 1.3 Hz, 1H), 6.94 (d, J = 8.4 Hz, 1H), 6.50 (s, 2H), 3.69 (s, 3H). |
| 91 | (structure: 3-methoxyphenoxy-isoxazolo[5,4-b]pyridin-3-amine) | 258.1 | 1H NMR (400 MHz, DMSO-d6) δ 8.26 (d, J = 8.4 Hz, 1H), 7.36 (t, J = 8.2 Hz, 1H), 6.95 (d, J = 8.4 Hz, 1H), 6.86 (dd, J1 = 8.3 Hz, J2 = 1.9 Hz, 1H), 6.82-6.75 (m, 2H), 6.52 (s, 2H), 3.76 (s, 3H) |
| 92 | (structure: 4-methoxyphenoxy-isoxazolo[5,4-b]pyridin-3-amine) | 258.1 | 1H NMR (400 MHz, DMSO-d6) δ 8.23 (d, J = 8.4 Hz, 1H), 7.13 (d, J = 9.2 Hz, 2H), 7.00 (d, J = 9.2 Hz, 2H), 6.92 (d, J = 8.4 Hz, 1H), 6.50 (s, 2H), 3.78 (s, 3H). |
| 93 | (structure: 3-trifluoromethylphenoxy-isoxazolo[5,4-b]pyridin-3-amine) | 296.0 | 1H NMR (400 MHz, DMSO-d6) δ 8.31 (d, J = 8.4 Hz, 1H), 7.73-7.64 (m, 3H), 7.57 (d, J = 8.0 Hz, 1H), 7.06 (d, J = 8.4 Hz, 1H), 6.55 (s, 2H). |

Method 8. Representative Procedure 6-(Methylthio)isoxazolo[5,4-b]pyridin-3-amine (79) and 6-(methylsulfonyl)isoxazolo[5,4-b]pyridin-3-amine (80)

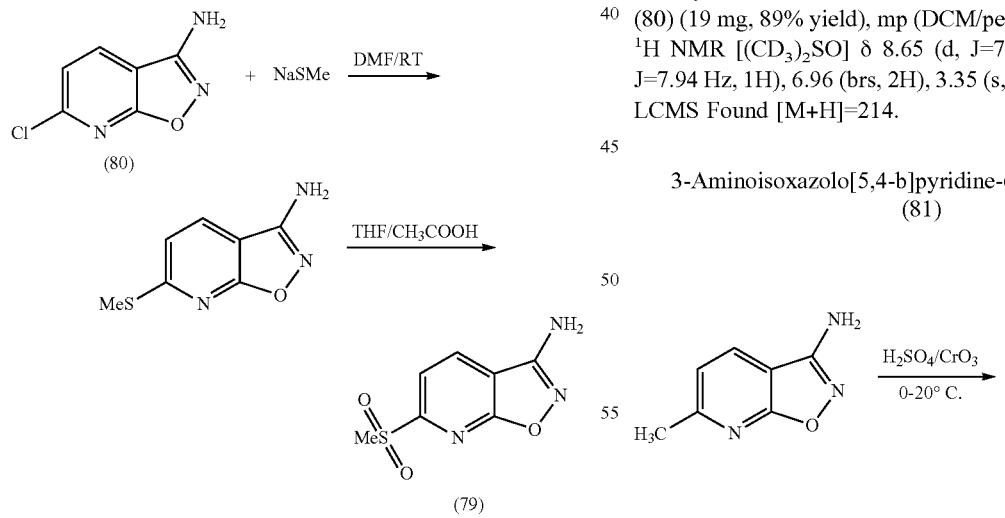

Reaction of 6-chloroisoxazolo[5,4-b]pyridine-3-amine and 3 equivalents of sodium thiomethoxide in DMF at room temperature for 18 h gave (79) in 68% yield, mp (DCM/MeOH) 230-233° C.; 1H NMR [(CD$_3$)$_2$SO] δ 8.07 (d, J=8.2 Hz, 1H), 7.24 (d, J=8.2 Hz, 1H), 6.53 (brs, 2H), 2.56 (s, CH$_3$); HPLC 99.3%; HRMS (ESI+) calcd. for C$_7$H$_8$N$_3$OS [M+H] 182.0383; found 182.0380.

To a solution of (79) (18 mg, 0.1 mmol) in THF (3.0 mL) was added peracetic acid (0.5 mL of a 32% solution in acetic acid) and the reaction mixture was stirred at 20° C. for 30 hr. The solvents were evaporated at 20° C. and the residue was diluted with H$_2$O, basified with K$_2$CO$_3$, extracted into EtOAc and dried over Na$_2$SO$_4$. Evaporation of the solvents and crystallization of the residue from DCM/pet. ether gave (80) (19 mg, 89% yield), mp (DCM/pet. ether) 231-234° C.; 1H NMR [(CD$_3$)$_2$SO] δ 8.65 (d, J=7.9 Hz, 1H), 8.04 (d, J=7.94 Hz, 1H), 6.96 (brs, 2H), 3.35 (s, CH$_3$); HPLC 98.5%; LCMS Found [M+H]=214.

3-Aminoisoxazolo[5,4-b]pyridine-6-carboxylic acid (81)

-continued

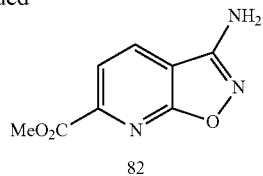

82

6-Methylisoxazolo[5,4-b]pyridin-3-amine (48 mg, 0.32 mmol) was dissolved in concentrated $H_2SO_4$ (5 mL) at 0° C., then $CrO_3$ (160 mg, 1.6 mmol) was added and stirring was continued for 20 hr at 20° C. The mixture was then stirred in ice, and the resulting precipitate was filtered, washed with $H_2O$, and a 1:1 mixture of pet. ether/DCM, then dried in the oven to give 81 (8.0 mg, 14%); $^1$H NMR [$(CD_3)_2SO$] δ 12.78 (br, 1H), 8.45 (d, J=7.9 Hz, 1H), 8.02 (d, J=7.9 Hz, 1H), 6.81 (brs, 2H). HPLC 96%. LCMS found [M+H]=178.

Methyl 3-aminoisoxazolo[5,4-b]pyridine-6-carboxylate (82)

6-Methylisoxazolo[5,4-b]pyridin-3-amine (248 mg, 1.66 mmol) was dissolved in cooled concentrated $H_2SO_4$ (10 ml) at 0° C. then $CrO_3$ (350 mg, 3.5 mmol) was added and the mixture was stirred at 20° C. for 3 days. After cooling to 0° C. MeOH (1 ml) was added and stirring was continued at 20° C. for 20 hr. The mixture was diluted with water and extracted into EtOAc. Combined extracts were dried ($Na_2SO_4$) and evaporation of the solvents followed by HPLC separation of the residue gave 82 (44 mg), $^1$H NMR [$(CD_3)_2SO$] δ 8.48 (d, J=8.0 Hz, 1H), 8.05 (d, J=8.0 Hz, 1H), 6.84 (brs, 2H), 3.92 (s, 3H) Anal. calcd for $C_8H_7N_3O_3$: C, 49.7; H, 3.6; N, 21.7; found C, 49.8; H, 3.5; N, 21.8%. HPLC 99.6%.

Enzymatic Assay for IDO1 Activity

Recombinant human IDO1 (rhIDO1) was expressed and purified from cultures of EC538 strain of *E. coli* transformed with pREP4 and pQE9-IDO plasmid. Reaction mixes were set up in 384-well microplates containing 50 mM phosphate buffer, 10 mM ascorbic, 10 μM methylene blue, 100 μg/mL catalase, 80 μM TRP, 0.01% Tween 20 (v/v) mixed with rhIDO1 (15 μL) at a final concentration of 9 nM in a total volume of 30 μL assay medium. The plates were incubated at 37° C. for 30 min, and the enzymatic reaction was terminated by adding piperidine (200 mM) and heated at 65° C. for 20 min. Fluorescence intensity was read at $\lambda_{ex}$ 400 nm and $\lambda_{em}$ 500 nm. Test compounds were dissolved in 100% DMSO and pre-diluted in assay medium prior to adding rhIDO1. IDO1 inhibition (%) was calculated as $$\left(\frac{(|\text{uninhibited enzyme assay signal}| - |\text{inhibited enzyme signal}|)}{(|\text{uninhibited enzyme assay signal}| - |\text{assay medium signal}|)} \times 100\right)$$

All experiments were carried out in triplicates, and statistical Analyses were conducted in Prism v5 (Graphpad Software, Inc., La Jolla, Calif., USA).

Cell-Based Assay for IDO1 Inhibition

For the assay of inhibition of cellular IDO1 activity, Lewis Lung carcinoma cells transfected to express human IDO1 (LLTC-hIDO1) or murine (LLTC-mIDO1) were cultured with test compounds at 37° C., 5% $CO_2$ for 24 h. Culture supernatant from each well was then transferred into a fresh, flat-bottomed 96-well plate, mixed with trichloroacetic acid (10% final concentration) and incubated for 20 min at 60° C. Plates were then centrifuged (10 min at 2500 g) and the supernatants were then transferred and mixed 1:1 with 4-(dimethylamino)benzaldehyde (20 mg/mL in acetic acid) in a new plate. The absorbance of each well was read at 480 nm, and the concentration that inhibited 50% cellular enzyme activity was calculated.

The viability of the cells in each well in the same experiment was determined using the 3-(4,5-dimethylthiazolyl-2-yl)-2,5-diphenyltetrazolium bromide (MTT) colourimetric assay. After the removal of the supernatant for determination of IDO1 inhibition, the cells were incubated with MTT (500 μg/mL) until crystal formation was observed. Plates were centrifuged for 15 min at 2500 g, and then all the supernatant in then wells was discarded. DMSO (100 μL/well) was added to dissolve the crystals and then the absorbance in each well was measured at 570 nm. Cell viability in each well was expressed as a percentage of untreated controls. Triplicate cultures were used for all experiments unless stated otherwise.

Results of the assays are shown in the table below.

Compound Activity

| Compound No | Enzymatic IC$_{50}$ (μM) | Cellular IC$_{50}$ (μM) | Cell Viability IC$_{50}$ (μM) |
|---|---|---|---|
| 1 | B | A | D |
| 2 | D | C | D |
| 3 | B | A | D |
| 4 | C | B | D |
| 5 | C | — | — |
| 6 | C | A | D |
| 7 | D | — | — |
| 8 | C | A | D |
| 9 | C | B | D |
| 10 | D | B | D |
| 11 | B | A | D |
| 12 | D | B | D |
| 13 | D | D | D |
| 14 | D | — | — |
| 15 | D | B | D |
| 16 | B | A | D |
| 17 | D | — | — |
| 18 | D | — | — |
| 19 | D | — | — |
| 20 | D | C | D |
| 28 | D | — | — |
| 30 | D | — | — |
| 33 | D | — | — |
| 42 | A | A | D |
| 43 | D | — | — |
| 44 | D | C | D |
| 45 | D | C | D |
| 46 | D | C | D |
| 47 | A | B | D |
| 48 | D | C | D |
| 49 | B | A | D |
| 50 | C | C | D |
| 51 | D | — | — |
| 52 | D | C | D |
| 53 | D | — | — |
| 54 | D | C | D |
| 55 | D | — | — |
| 56 | D | D | D |
| 57 | D | D | D |
| 58 | D | B | D |
| 59 | D | D | D |
| 60 | D | — | — |
| 61 | D | — | — |
| 62 | D | — | — |
| 63 | D | C | D |
| 64 | D | C | D |
| 65 | D | D | D |
| 66 | A | A | D |
| 67 | A | B | D |
| 68 | D | C | D |

-continued

| Compound No | Enzymatic IC$_{50}$ (µM) | Cellular IC$_{50}$ (µM) | Cell Viability IC$_{50}$ (µM) |
|---|---|---|---|
| 69 | D | C | D |
| 70 | D | D | D |
| 71 | D | C | D |
| 72 | D | D | D |
| 73 | D | C | D |
| 74 | D | B | D |
| 75 | D | D | D |
| 76 | D | D | D |
| 77 | D | D | D |
| 78 | D | D | D |
| 79 | C | B | D |
| 80 | D | C | D |
| 81 | D | D | D |
| 82 | D | C | D |
| 83 | D | — | — |
| 84 | C | C | D |
| 85 | D | — | — |
| 86 | D | — | — |
| 87 | D | C | D |
| 88 | D | C | D |
| 89 | D | C | D |
| 90 | D | C | D |
| 91 | D | — | — |
| 92 | D | — | — |
| 93 | D | C | D |
| 94 | D | B | D |
| 95 | D | B | D |
| 96 | D | D | D |

Activity IC$_{50}$ ranges: A; <1 µM, B; 1-10 µM, C; 10-100 µM, D; >100 µM

Cell-Based Assay for TDO Inhibition

For the assay of inhibition of cellular TDO, GL261 cells transfected to over-express full length human TDO were cultured with test compounds at 37° C., 5% CO$_2$ for 24 h. Culture supernatant from each well was then transferred into a fresh, flat-bottomed 96-well plate, and kynurenine content was determined as described above for the IDO1 assay, and the concentration that inhibited 50% cellular enzyme activity was calculated.

The viability of the cells in each well in the same experiment was determined using the 3-(4,5-dimethylthiazolyl-2-yl)-2,5-diphenyltetrazolium bromide (MTT) colourimetric assay.

Results of the assay are shown in the table below.

Compound Activity

| Compound No | Cellular IC$_{50}$ (uM) | Cell Viability IC$_{50}$ (uM) |
|---|---|---|
| 3 | B | D |
| 11 | A | D |
| 66 | A | D |
| 89 | C | D |

Activity IC$_{50}$ ranges: A; <1 µM, B; 1-10 µM, C; 10-100 µM, D; >100 µM

Determination of Tumor Growth Inhibition

Tumours were implanted subcutaneously into syngeneic C57Bl/6 mice and allocated into different treatment groups when tumours had reached approximately 3×3 mm in size. Compounds were dissolved in DMSO and the dose in a volume of 50 ml was administered by daily injection either ip or sc. Tumours were measured every second day and mice were monitored until humane ethical endpoint was reached.

The results of the study are shown in FIG. 1 for Compound 3, using the Lewis Lung TC carcinoma line which has been transfected to produce human IDO1. Tumour volume is in mm$^3$. N=7 per group. *Indicates significance by repeated measures one-way Anova.

Determination of Changes in Kynurenine to Tryptophan Ratios (K:T).

K:T ratios in plasma and tumours from mice with 16 day subcutaneous GL-261-hIDO1 tumours (tumour size 15-20 mm), were determined by analytical HPLC 0.25 h, 1 h, 2 h, 4 h, 6 h and 24 h following treatment with 150 mg/kg Compound 3, n=3 per time point. DMSO vehicle control group (n=21) pooled from 3 mice, 0.25 h, 1 h, 2 h, 4 h, 6 h and 24 h following treatment with DMSO. * and ** denotes significance (p<0.05, p<0.01, respectively) by one-way ANOVA and Sidak's multiple comparisons compared to DMSO controls.

Figure 2:
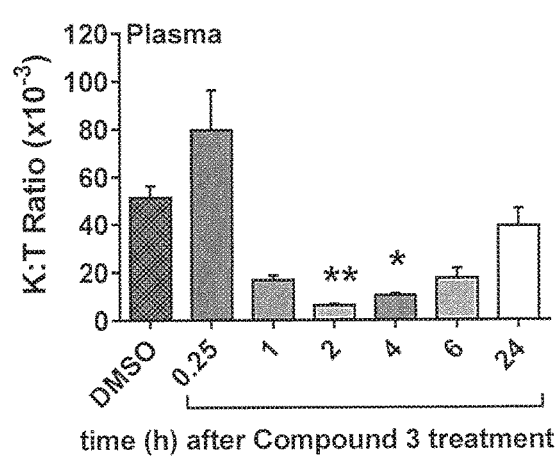
FIG. 2 shows K:T ratios in plasma and tumours from mice with 16 day subcutaneous GL-261-hIDO1 tumours (tumour size 15-20 mm), determined by analytical HPLC 0.25 h, 1 h, 2 h, 4 h, 6 h and 24 h following treatment with 150 mg/kg Compound 3, n=3 per time point. DMSO vehicle control group (black, n=21) pooled from 3 mice, 0.25 h, 1 h, 2 h, 4 h, 6 h and 24 h following treatment with DMSO. * and ** denotes significance ($p<0.05$, $p<0.01$, respectively) by one-way ANOVA and Sidak's multiple comparisons compared to DMSO controls.
Figure 2:
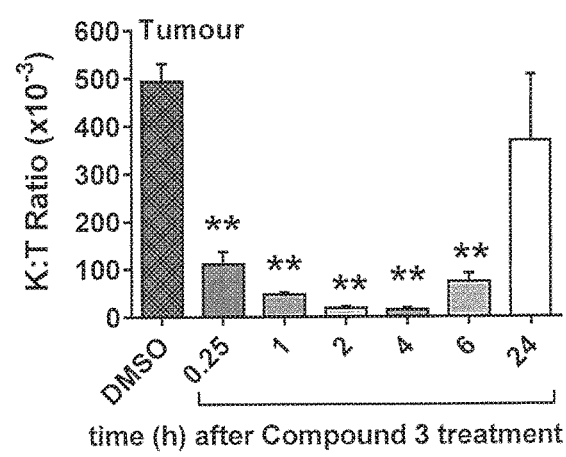

Results of this study are shown in FIG. 2.

Determination of Synergy in Combination with Immune Checkpoint Blockades.

Figure 3:
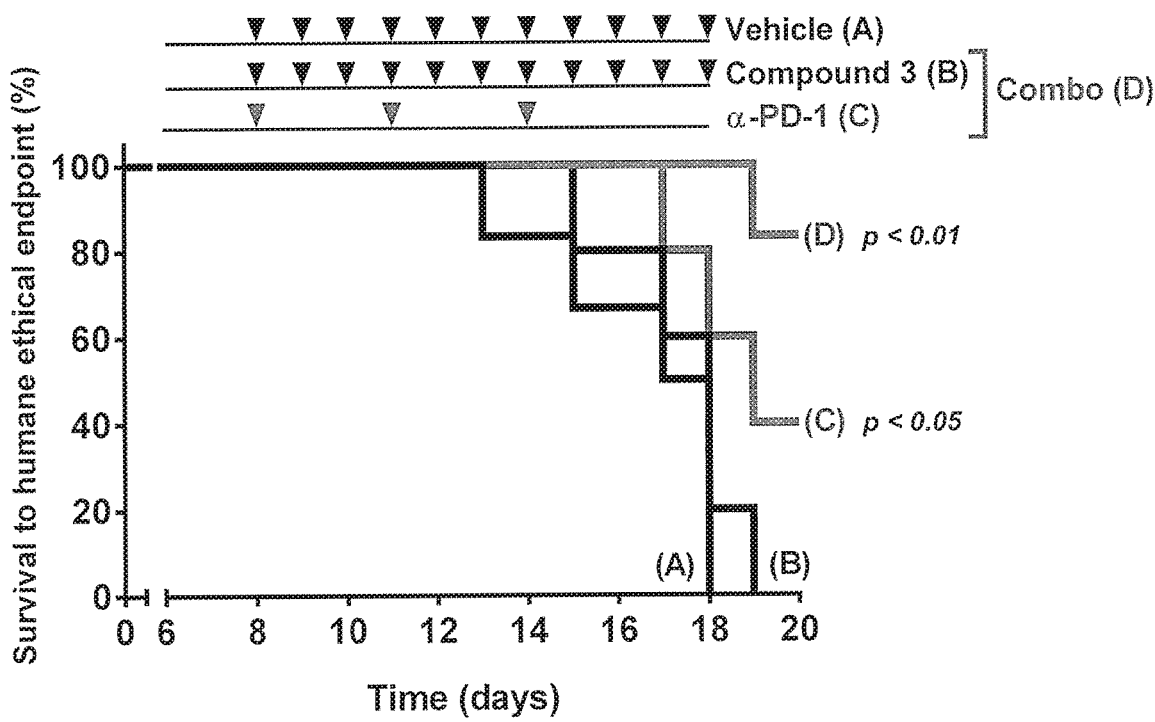
FIG. 3 shows survival to humane ethical end point of a study with mice with sc GL261-hIDO1 tumours treated with vehicle (A); Compound 3 at 75 mg/kg (B) IP daily, beginning 8 days after tumor implantation; anti-immune checkpoint antibodies (C) against anti-PD1 (Top: 250 µg/mouse IP on days 8, 11 and 14 after tumor implantation) or anti-CTLA4 (Bottom: 1 mg/mouse IP 6 days after tumor implantation); or a combination (D) of Compound 3 plus immune checkpoint antibody. P-values indicate significant difference by Log-rank analysis compared to vehicle survival curves. Coloured arrowheads indicate dosing schedule.
Figure 3:
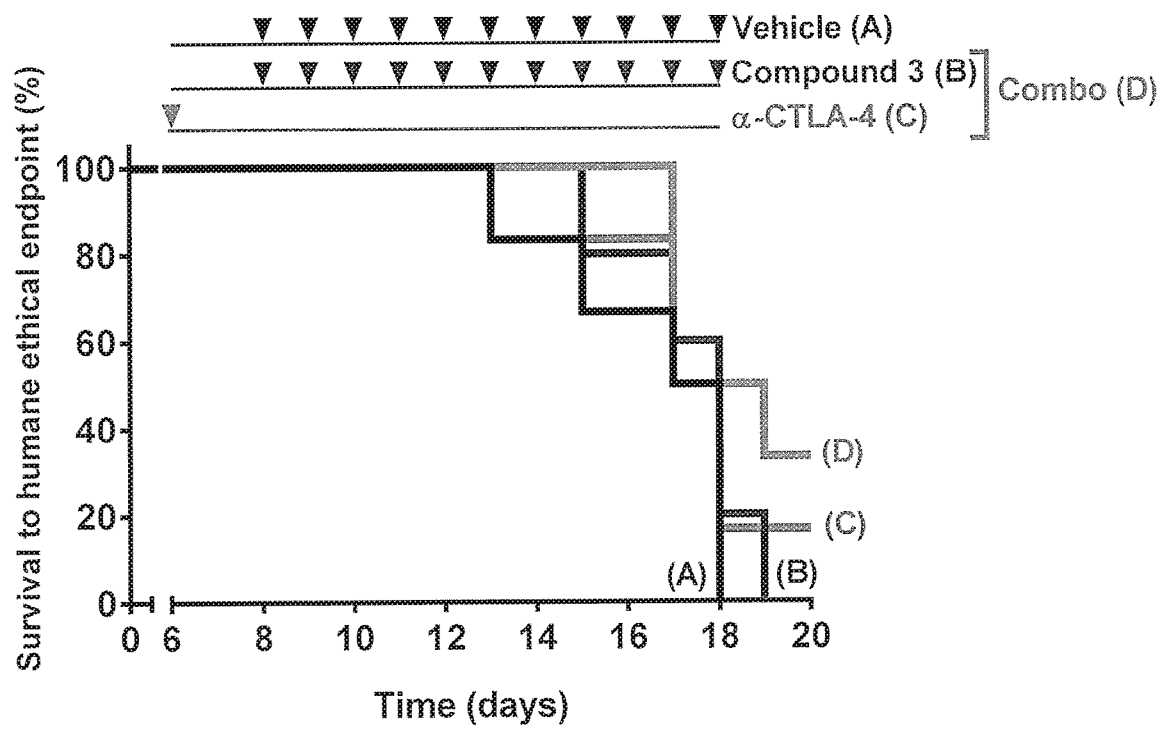

FIG. 3 shows survival to humane ethical end point of a study with mice with sc GL261-hIDO1 tumours treated with vehicle (A); Compound 3 at 75 mg/kg (B) IP daily, beginning 8 days after tumor implantation; anti-immune checkpoint antibodies (C) against anti-PD1 (Top: 250 µg/mouse IP on days 8, 11 and 14 after tumor implantation) or anti-CTLA4 (Bottom: 1 mg/mouse IP 6 days after tumor implantation); or a combination (D) of Compound 3 plus immune checkpoint antibody. P-values indicate significant difference by Log-rank analysis compared to vehicle survival curves. Coloured arrowheads indicate dosing schedule.

Results of this study are shown in FIG. 3.

As used herein, "comprising" is synonymous with "including," "containing," or "characterized by," and is inclusive or open-ended and does not exclude additional, unrecited elements or method steps. As used herein, "consisting of" excludes any element, step, or ingredient not specified in the claim element. As used herein, "consisting essentially of" does not exclude materials or steps that do not materially affect the basic and novel characteristics of the claim. In each instance herein any of the terms "comprising", "consisting essentially of" and "consisting of" may be replaced with either of the other two terms.

When a group of materials, compositions, components or compounds is disclosed herein, it is understood that all individual members of those groups and all subgroups thereof are disclosed separately. When a Markush group or other grouping is used herein, all individual members of the group and all combinations and subcombinations possible of the group are intended to be individually included in the disclosure. Every formulation or combination of components described or exemplified herein can be used to practice the invention, unless otherwise stated. Whenever a range is given in the specification, for example, a temperature range, a time range, or a composition range, all intermediate ranges and subranges, as well as all individual values included in the ranges given are intended to be included in the disclosure. In the disclosure and the claims, "and/or" means additionally or alternatively. Moreover, any use of a term in the singular also encompasses plural forms.

All references cited herein are hereby incorporated by reference in their entirety to the extent that there is no inconsistency with the disclosure of this specification. Some references provided herein are incorporated by reference to provide details concerning sources of starting materials, additional starting materials, additional reagents, additional methods of synthesis, additional methods of analysis, additional biological materials, additional cells, and additional uses of the invention. All headings used herein are for convenience only. All patents and publications mentioned in the specification are indicative of the levels of skill of those skilled in the art to which the invention pertains, and are herein incorporated by reference to the same extent as if each individual publication, patent or patent application was specifically and individually indicated to be incorporated by reference. References cited herein are incorporated by reference herein in their entirety to indicate the state of the art as of their publication or filing date and it is intended that this information can be employed herein, if needed, to exclude specific embodiments that are in the prior art.

The invention claimed is:

1. 6-chloro-5-fluoroisoxazolo [5,4-b]pyridin-3-amine or a pharmaceutically acceptable salt thereof.

2. A compound selected from the following:
5-Bromo-4,6-dimethylisoxazolo[5,4-b]pyridin-3-amine;
4,5,6-Trimethylisoxazolo[5,4-b]pyridin-3-amine;
5-Chloroisoxazolo[5,4-b]pyridin-3-amine;
6-Phenylisoxazolo[5,4-b]pyridin-3-amine;
5-Iodoisoxazolo[5,4-b]pyridin-3-amine;
5-Chloro-N³,4,6-trimethylisoxazolo[5,4-b]pyridin-3-amine;
5-Chloro-N³,N³,4,6-tetramethylisoxazolo[5,4-b]pyridin-3-amine;
5-(3-Methoxyphenyl)isoxazolo[5,4-b]pyridin-3-amine;
5-(2-Methoxyphenyl)isoxazolo[5,4-b]pyridin-3-amine;
5-(3-Fluoro-4-methoxyphenyl)isoxazolo[5,4-b]pyridin-3-amine;
5-(Pyridin-3-yl)isoxazolo[5,4-b]pyridin-3-amine;
5-(Pyridin-4-yl)isoxazolo[5,4-b]pyridin-3-amine;
4-(3-Aminoisoxazolo[5,4-b]pyridin-5-yl)phenol;
5-(3-Fluorophenyl)isoxazolo[5,4-b]pyridin-3-amine;
5-(2,4-difluorophenyl)isoxazolo[5,4-b]pyridin-3-amine;
5-(2,4-Dichlorophenyl)isoxazolo[5,4-b]pyridin-3-amine;
5-(2,3,4-Trichlorophenyl)isoxazolo[5,4-b]pyridin-3-amine;
5-(4-(Trifluoromethylphenyl)isoxazolo[5,4-b]pyridin-3-amine;
5-(3-Aminophenyl)isoxazolo[5,4-b]pyridin-3-amine;
Methyl 3-(3-aminoisoxazolo[5,4-b]pyridin-5-yl)benzoate;
5-(6-Fluoropyridin-3-yl)isoxazolo[5,4-b]pyridin-3-amine;
5-(2-Chloro-4-(trifluoromethyl)phenyl)isoxazolo[5,4-b]pyridin-3-amine;
6-Chloro-4-methylisoxazolo[5,4-b]pyridin-3-amine;
5,6-Dimethylisoxazolo[5,4-b]pyridin-3-amine;
6-Methyl-4-(trifluoromethyl)isoxazolo[5,4-b]pyridin-3-amine;
6-Isopropylisoxazolo[5,4-b]pyridin-3-amine;
5-Nitroisoxazolo[5,4-b]pyridin-3-amine;
Ethyl 3-amino-6-(trifluoromethyl)isoxazolo[5,4-b]pyridine-5-carboxylate;
5-(Difluoromethoxy)-4,6-dimethylisoxazolo[5,4-b]pyridin-3-amine;
Ethyl 3-amino-6-(difluoromethyl)isoxazolo[5,4-b]pyridine-5-carboxylate;
6-(Furan-2-yl)isoxazolo[5,4-b]pyridin-3-amine;
6-(Methylthio)isoxazolo[5,4-d]pyrimidin-3-amine;
6-Chloro-5-fluoroisoxazolo[5,4-b]pyridin-3-amine;
5,6-Dichloroisoxazolo[5,4-b]pyridin-3-amine;
6-Chloro-4-(trifluoromethyl)isoxazolo[5,4-b]pyridin-3-amine;
5-(3-Methoxyprop-1-yn-1-yl)isoxazolo[5,4-b]pyridin-3-amine;
6-(4-Fluorophenyl)isoxazolo[5,4-b]pyridin-3-amine;
6-(2,4-Difluorophenyl)isoxazolo[5,4-b]pyridin-3-amine;
6-(2-Thienyl)isoxazolo[5,4-b]pyridin-3-amine;
6-(Methylthio)isoxazolo[5,4-b]pyridin-3-amine;
6-(methylsulfonyl)isoxazolo[5,4-b]pyridin-3-amine;
Methyl 3-aminoisoxazolo[5,4-b]pyridine-6-carboxylate;
6-(2-Chlorophenoxy)isoxazolo[5,4-b]pyridin-3-amine;
6-(2-(Trifluoromethoxy)phenoxy)isoxazolo[5,4-b]pyridin-3-amine;
6-(3-(Trifluoromethoxy)phenoxy)isoxazolo[5,4-b]pyridin-3-amine;
6-(4-(Trifluoromethoxy)phenoxy)isoxazolo[5,4-b]pyridin-3-amine;
6-(2-Methoxyphenoxy)isoxazolo[5,4-b]pyridin-3-amine;
6-(3-(Trifluoromethyl)phenoxy)isoxazolo[5,4-b]pyridin-3-amine;
N⁶-Phenylisoxazolo[5,4-b]pyridine-3,6-diamine; and
N⁶-(3-Methoxyphenyl)isoxazolo[5,4-b]pyridine-3,6-diamine;
or a pharmaceutically acceptable salt thereof.

3. A compound selected from the following:
5-Bromo-4,6-dimethylisoxazolo[5,4-b]pyridin-3-amine;
5-Chloroisoxazolo[5,4-b]pyridin-3-amine;
6-Phenylisoxazolo[5,4-b]pyridin-3-amine;
5-Iodoisoxazolo[5,4-b]pyridin-3-amine;
5-Chloro-N³,4,6-trimethylisoxazolo[5,4-b]pyridin-3-amine;
5-Chloro-N³,N³,4,6-tetramethylisoxazolo[5,4-b]pyridin-3-amine;
5-(3-Methoxyphenyl)isoxazolo[5,4-b]pyridin-3-amine;
5-(2-Methoxyphenyl)isoxazolo[5,4-b]pyridin-3-amine;
5-(3-Fluoro-4-methoxyphenyl)isoxazolo[5,4-b]pyridin-3-amine;
5-(Pyridin-3-yl)isoxazolo[5,4-b]pyridin-3-amine;
5-(Pyridin-4-yl)isoxazolo[5,4-b]pyridin-3-amine;
4-(3-Aminoisoxazolo[5,4-b]pyridin-5-yl)phenol;
5-(3-Fluorophenyl)isoxazolo[5,4-b]pyridin-3-amine;
5-(2,4-difluorophenyl)isoxazolo[5,4-b]pyridin-3-amine;
5-(2,4-Dichlorophenyl)isoxazolo[5,4-b]pyridin-3-amine;
5-(2,3,4-Trichlorophenyl)isoxazolo[5,4-b]pyridin-3-amine;
5-(4-(Trifluoromethylphenyl)isoxazolo[5,4-b]pyridin-3-amine;
5-(3-Aminophenyl)isoxazolo[5,4-b]pyridin-3-amine;
Methyl 3-(3-aminoisoxazolo[5,4-b]pyridin-5-yl)benzoate;
5-(6-Fluoropyridin-3-yl)isoxazolo[5,4-b]pyridin-3-amine;
5-(2-Chloro-4-(trifluoromethyl)phenyl)isoxazolo[5,4-b]pyridin-3-amine;
6-Chloro-4-methylisoxazolo[5,4-b]pyridin-3-amine;
6-Methyl-4-(trifluoromethyl)isoxazolo[5,4-b]pyridin-3-amine;
6-Isopropylisoxazolo[5,4-b]pyridin-3-amine;
5-Nitroisoxazolo[5,4-b]pyridin-3-amine;
Ethyl 3-amino-6-(trifluoromethyl)isoxazolo[5,4-b]pyridine-5-carboxylate;
5-(Difluoromethoxy)-4,6-dimethylisoxazolo[5,4-b]pyridin-3-amine;
Ethyl 3-amino-6-(difluoromethyl)isoxazolo[5,4-b]pyridine-5-carboxylate;
6-(Furan-2-yl)isoxazolo[5,4-b]pyridin-3-amine;
6-(Methylthio)isoxazolo[5,4-d]pyrimidin-3-amine;
6-Chloro-5-fluoroisoxazolo[5,4-b]pyridin-3-amine;
5,6-Dichloroisoxazolo[5,4-b]pyridin-3-amine;
6-Chloro-4-(trifluoromethyl)isoxazolo[5,4-b]pyridin-3-amine;
5-(3-Methoxyprop-1-yn-1-yl)isoxazolo[5,4-b]pyridin-3-amine;
6-(4-Fluorophenyl)isoxazolo[5,4-b]pyridin-3-amine;
6-(2,4-Difluorophenyl)isoxazolo[5,4-b]pyridin-3-amine;
6-(2-Thienyl)isoxazolo[5,4-b]pyridin-3-amine;

6-(Methylthio)isoxazolo[5,4-b]pyridin-3-amine;
6-(methylsulfonyl)isoxazolo[5,4-b]pyridin-3-amine;
Methyl 3-aminoisoxazolo[5,4-b]pyridine-6-carboxylate;
6-(2-Chlorophenoxy)isoxazolo[5,4-b]pyridin-3-amine;
6-(2-(Trifluoromethoxy)phenoxy)isoxazolo[5,4-b]pyridin-3-amine;
6-(3-(Trifluoromethoxy)phenoxy)isoxazolo[5,4-b]pyridin-3-amine;
6-(4-(Trifluoromethoxy)phenoxy)isoxazolo[5,4-b]pyridin-3-amine;
6-(2-Methoxyphenoxy)isoxazolo[5,4-b]pyridin-3-amine;
6-(3-(Trifluoromethyl)phenoxy)isoxazolo[5,4-b]pyridin-3-amine;
$N^6$-Phenylisoxazolo[5,4-b]pyridine-3,6-diamine; and
$N^6$-(3-Methoxyphenyl)isoxazolo[5,4-b]pyridine-3,6-diamine;
or a pharmaceutically acceptable salt thereof.

4. The compound of claim 2, wherein the compound is selected from:
5-chloroisoxazolo[5,4-b]pyridin-3-amine;
5-iodoisoxazolo[5,4-b]pyridin-3-amine; and
5,6-dichloroisoxazolo[5,4-b]pyridin-3-amine; or a pharmaceutically acceptable salt thereof.

\* \* \* \* \*